(12) United States Patent
Mouquet et al.

(10) Patent No.: US 10,392,433 B2
(45) Date of Patent: Aug. 27, 2019

(54) BROADLY NEUTRALIZING ANTIBODY DIRECTED AGAINST HIV-1 GP140

(71) Applicant: The Rockefeller Universtiy, New York, NY (US)

(72) Inventors: Hugo Mouquet, New York, NY (US); Michel Nussenzweig, New York, NY (US); Pamela J. Bjorkman, La Canada Flintridge, CA (US); Louise Scharf, Porter Ranch, CA (US)

(73) Assignees: The Rockefeller University, New York, NY (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 16/006,420

(22) Filed: Jun. 12, 2018

(65) Prior Publication Data
US 2018/0282400 A1    Oct. 4, 2018

Related U.S. Application Data

(62) Division of application No. 14/436,608, filed as application No. PCT/US2013/065696 on Oct. 18, 2013, now Pat. No. 10,047,146.

(60) Provisional application No. 61/715,642, filed on Oct. 18, 2012.

(51) Int. Cl.
C07K 16/10        (2006.01)
A61K 39/00        (2006.01)

(52) U.S. Cl.
CPC ...... C07K 16/1045 (2013.01); C07K 16/1063 (2013.01); A61K 2039/505 (2013.01); C07K 2317/21 (2013.01); C07K 2317/33 (2013.01); C07K 2317/34 (2013.01); C07K 2317/565 (2013.01); C07K 2317/76 (2013.01); C07K 2317/92 (2013.01)

(58) Field of Classification Search
CPC .................................................. C07K 16/1063
See application file for complete search history.

(56) References Cited

U.S. PATENT DOCUMENTS

| 2005/0032042 A1 | 2/2005 | Soldin |
| 2008/0050754 A1 | 2/2008 | Yamada et al. |
| 2008/0279879 A1 | 11/2008 | Zolla-Pazner |
| 2009/0226886 A1 | 9/2009 | Mitsuhashi |
| 2011/0262474 A1 | 10/2011 | Du et al. |

FOREIGN PATENT DOCUMENTS

| WO | 2011092593 A2 | 8/2011 |
| WO | 2012030904 A2 | 3/2012 |
| WO | 2012074863 A2 | 6/2012 |

OTHER PUBLICATIONS

Bansal, G. P., 2007, A summary of the workshop on passive immunization using monoclonal antibodies for HIV/AIDS, held at the National Institute of Allergy and Infectious Diseases, Bethesda, Mar. 10, 2006, Biologicals 35:367-371.*
Trkola, A., et al., 2005, Delay of HIV-1 rebound after cessation of antiretroviral therapy through passive transfer of human neutralizing antibodies, Nat. Med. 11(6):615-622.*
Montefiori, D. C., 2005, Neutralizing antibodies take a swipe at HIV in vivo, Nat. Med. 11(6):593-594.*
Haigwood, N. L., 2004, Predictive value of primate models for AIDS, AIDS Reviews,6:187-198.*
Staprans, S. I., and M. B. Feinberg, 2004, The roles of nonhuman primates in the preclinical evaluation of candidate AIDS vaccines, Expert Rev. Vacc. 3(4), Suppl., 5-32.*
Mouquet et al., "Polyreactivity increases the apparent affinity of anti-HIV antibodies by heteroligation," Nature (Sep. 30, 2010); 467(7315):591-595.
Walker et al., "Broad neutralization coverage of HIV by multiple highly potent antibodies," Nature (Sep. 22, 2011); 477:466-471.
Walker et al., "Supplementary Information—Broad neutralization coverage of HIB by multiple highly otent antibodies," Nature (Aug. 17, 2011); pp. 1-15.
Scanlan et al., "The Broadly Neutralizing Anti-Human Immunodeficiency Virus Type 1 Antibody 2G12 Recognizes a Cluster of α1-2 Mannose Residues on the Outer Face of gp120," Journal of Virology (Jul. 2002); 76(14):7306-7321.
Walker et al, "Rapdi developmetn of glycan-specific, broad, and potent anti-HIV-1 gp120 neutralizing antibodies in an R5 SIV/HIV chimeric virus infected macaque," PNAS (Dec. 13, 2011); 108(50):20125-20129.
Walker et al., "Broad and Potet Neutralizing Antibodies from an African Donor Reveal a New HIV-1 Vaccine Target," Science (Corrected Oct. 9, 2009); 326:285-289.
Walker et al., "Supporting Online Material for—Broad and Potent Neutralizing Antibodies from an African Donor Reveal a New HIV-1 Vaccine Target," Science (published Sep. 3, 2009) pp. 1-27.
Kwong et all., "Human Antibodies that Neutralize HIV-1: Identification, Structures, and B Cell Ontogenies," Immunity (Sep. 21, 2012); 37:412-425.
Pereira et al., "Simian-Human Immunodeficiency Viruses and Their Impact on Non-Human Primate Models for AIDS," Immunodeficiency (2012); Chapter 15, pp. 311-356.
Pegu et al., "Use of broadly neutralizing antibodies for HIV-1 prevention," Immunological Reviews (2017); 275:296-312.
Burton et al., "Broadly Neutralizing Antibodies to HIV an dTheir Role in Vaccine Design," Annu. Rev. Immunol. (2016); 34:635-659.
Kong et al., "Supersite of immune vulnerability on the glycosylated face of HIV-1 envelope glycoprotein gp120," Nat Sruct Mol Biol. (2013); 20(7):796-803.

(Continued)

*Primary Examiner* — Jeffrey S Parkin
(74) *Attorney, Agent, or Firm* — Fox Rothschild LLP

(57) ABSTRACT

The present invention relates to anti-HIV antibodies. Also disclosed are related methods and compositions. HIV causes acquired immunodeficiency syndrome (AIDS), a condition in humans characterized by clinical features including wasting syndromes, central nervous system degeneration and profound immunosuppression that results in life-threatening opportunistic infections and malignancies. Since its discovery in 1981, HIV type 1 (HIV-1) has led to the death of at least 25 million people worldwide.

12 Claims, 27 Drawing Sheets

Specification includes a Sequence Listing.

(56) References Cited

OTHER PUBLICATIONS

Caskey et al., "Antibody 10-1074 suppresses viremia in HIV-1-infected individuals," Nat Med. (2017); 12(2):185-191.
Gautam et al., "A single injection of anti-HIV-1 antibodies protects against repeated SHIV challenges," Nature (2016); 1-12.
Shingai et al., "Passive transfer of modest titers of potent and broadly neutralizing anti-HIV monoclonal antibodies block SHIV infection in macaques," J. Exp. Med. (2014); 10:2061-2074.
Bansal et al., "A summary of the owrkshop on passive immunization using monoclonal antibodies for HIV/AIDS," Biologicals (Mar. 10, 2006); 35:367-371.
Trkola et al., "Delay of HIV-1 rebound after cessation of antiretroviral therapy through passive transfer of human neutralizing antibodies," Nat Med. (2005); 11(6):615-622.
Montefiori, D.C., "Neutralizing antibodies take a swipe at HIV in vivo," Nat. Med. (2005); 11(6):593-594.
Haigwood, N.L., "Predictive value of primate models for AIDS," AIDS Review (2004); 6:187-198.
Staprans et al., "The roles of nonhuman primates in the preclincial evaluation of candidate AIDS vaccines," Expert Rev. Vacc. (2004); 3(4), Suppl., 5-32.
Liu et al., "Fine mapping of the antigen-antibody interaction of scFv215, a recombinant antibody inhibiting RNA polymerase II from *Drosophila melanogaster*," J. Mol. Recog. (1999); 12:103-111.
Li et al., "The I binding specificity of human VH4-34 (VH4-21) encoded antibodies is determined by both VH framework region 1 and complementarity determining region 3," J. Mol. Biol. (1996); 256:577-589.
Xiang et al., "Framework residues 71 and 93 of the chimeric B72.3 antibody are major determinants of the conformation of heavy-chain hypervariable loops," J. Mol. Biol. (1995); 253-385-390.
Kwong et al., "Human Antibodies that Neutralize HIV-1: Identification, Structures, and B Cell Ontogenies," Immunity (Sep. 21, 2012); 37:412-425.
Wu et al., "Focused Evolution of HIV-1 Neutralizing Antibodies Revealed by Structures and Deep Sequencing," Science (Sep. 16, 2011); 333:1593-1602.
Vasudevan et al., "A single amino acid change in the binding pocket altrers specificity of an anti-integrin antibody AP7.4 as revealed by its crystal structure," Blood Cells, Molecules & Diseases (2004); 32:176-181.

* cited by examiner

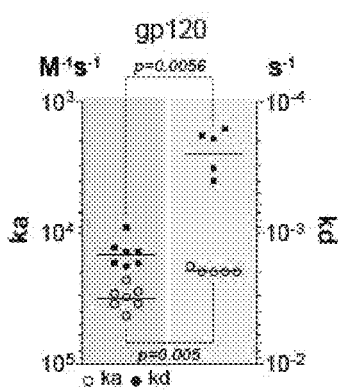
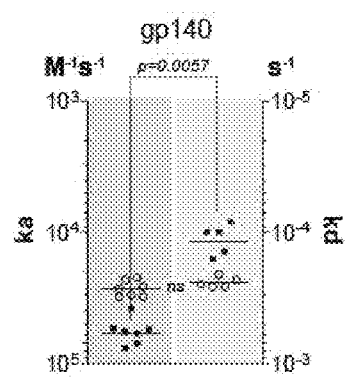
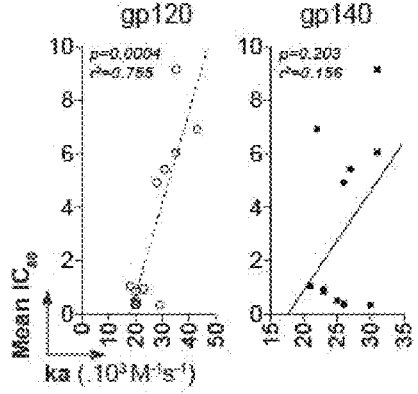
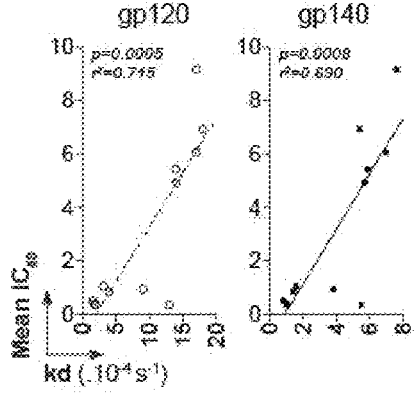
FIG. 4A, 4B and 4C

A

|  | IC50 TZM-bl (µg/ml) |
|---|---|
| VRC01 | 0.94 |
| NIH 45-46 | 0.92 |
| 45-46m2 | 0.29 |
| 45-46 G54W | 0.28 |
| 3BNC117 | 0.14 |
| 12A12 | 6.36 |
| 1NC9 | 2.04 |
| 8ANC195 | 3.38 |
| 10-1074 | 0.15 |
| PGT-121 | 0.10 |
| PGT-126 | 0.09 |

B

|  | IC50 TZM-bl (µg/ml) |
|---|---|
| VRC01 | 2.35 |
| NIH 45-46 | 1.48 |
| 45-46m2 | 0.52 |
| 45-46 G54W | 0.44 |
| 3BNC117 | 0.39 |
| 12A12 | 86.27 |
| 1NC9 | 30.26 |
| 8ANC195 | 3.08 |
| 10-1074 | 0.06 |
| PGT-121 | 0.01 |
| PGT-126 | 0.16 |

FIG. 11A and 11B a

|  | ID$_{50}$ (µg/ml) | |
| --- | --- | --- |
|  | 10-1074 | 3BNC117 |
| X2088_9 | 0.013 | >100 |
| Q769_d22 | >100 | 0.024 | b

| Plasma + mAb | Serum ID$_{50}$ Titer | | Serum ID$_{50}$ Titer converted to respected antibody concentration of 10-1074 and 3BNC117 (µg/ml) | |
| --- | --- | --- | --- | --- |
|  | X2088_9 | Q769_d22 | X2088_9 | Q769_d22 |
| preP_0.01_3BNC117 | <20 | <20 | <0.26 | <0.48 |
| preP_0.1_3BNC117 | <20 | <20 | <0.26 | <0.48 |
| preP_1_3BNC117 | <20 | 27 | <0.26 | 0.65 |
| preP_10_3BNC117 | <20 | 340 | <0.26 | 8.16 |
| preP_100_3BNC117 | <20 |  | <0.26 |  |
| preP_0.01_10-1074 | <20 | <20 | <0.26 | <0.48 |
| preP_0.1_10-1074 | <20 | <20 | <0.26 | <0.48 |
| preP_1_10-1074 | 54 | <20 | 0.70 | <0.48 |
| preP_10_10-1074 | 516 | <20 | 6.71 | <0.48 |
| preP_100_10-1074 |  | <20 |  | <0.48 | preT - pre-treatment plasma of different NHP's (D8Z3, DC99A, DCM8, DCF1, D8KE)

| ID50 Titer | µg/ml |
| --- | --- |
|  |  |
| 1000-5000 | >25-100 |
| 500-999 | >5-25 |
| 50-499 | 0.7-5 |

SEQUENCE LISTING

```
<160> NUMBER OF SEQ ID NOS: 223

<210> SEQ ID NO 1
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid or not present
<220> FEATURE:
<221> NAME/KEY: MOD_RES
<222> LOCATION: (29)..(30)
<223> OTHER INFORMATION: Any amino acid or not present
<220> FEATURE:
<221> NAME/KEY: MOD_RES
<222> LOCATION: (32)..(32)
<223> OTHER INFORMATION: Any amino acid or not present
<220> FEATURE:
<221> NAME/KEY: MOD_RES
<222> LOCATION: (68)..(69)
<223> OTHER INFORMATION: Any amino acid or not present
<220> FEATURE:
<221> NAME/KEY: MOD_RES
<222> LOCATION: (83)..(84)
<223> OTHER INFORMATION: Any amino acid or not present
<220> FEATURE:
<221> NAME/KEY: MOD_RES
<222> LOCATION: (92)..(92)
<223> OTHER INFORMATION: Any amino acid or not present
<220> FEATURE:
<221> NAME/KEY: MOD_RES
<222> LOCATION: (99)..(99)
<223> OTHER INFORMATION: Any amino acid or not present
```

```
<220> FEATURE:
<221> NAME/KEY: MOD_RES
<222> LOCATION: (102)..(102)
<223> OTHER INFORMATION: Any amino acid or not present
<220> FEATURE:
<221> NAME/KEY: MOD_RES
<222> LOCATION: (113)..(113)
<223> OTHER INFORMATION: Any amino acid or not present
<220> FEATURE:
<223> OTHER INFORMATION: See specification as filed for detailed
      description of substitutions and preferred embodiments

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ser Val Ser Gly Xaa Ser Xaa Xaa Asp Xaa
            20                  25                  30

Tyr Trp Ser Trp Ile Arg Gln Ser Pro Gly Lys Gly Leu Glu Trp Ile
        35                  40                  45

Gly Tyr Val His Asp Ser Gly Asp Thr Asn Tyr Asn Pro Ser Leu Lys
    50                  55                  60

Ser Arg Val Xaa Xaa Ser Leu Asp Thr Ser Lys Asn Gln Val Ser Leu
65                  70                  75                  80

Lys Leu Xaa Xaa Val Thr Ala Ala Asp Ser Ala Xaa Tyr Tyr Cys Ala
                85                  90                  95

Arg Ala Xaa His Gly Xaa Arg Ile Tyr Gly Ile Val Ala Phe Gly Glu
            100                 105                 110

Xaa Phe Thr Tyr Phe Tyr Met Asp Val Trp Gly Lys Gly Thr Thr Val
        115                 120                 125

Thr Val Ser Ser
    130

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid or not present
<220> FEATURE:
<221> NAME/KEY: MOD_RES
<222> LOCATION: (21)..(21)
<223> OTHER INFORMATION: Any amino acid or not present
<220> FEATURE:
<221> NAME/KEY: MOD_RES
<222> LOCATION: (25)..(25)
<223> OTHER INFORMATION: Any amino acid or not present
<220> FEATURE:
<221> NAME/KEY: MOD_RES
<222> LOCATION: (67)..(68)
<223> OTHER INFORMATION: Any amino acid or not present
<220> FEATURE:
<221> NAME/KEY: MOD_RES
<222> LOCATION: (79)..(79)
<223> OTHER INFORMATION: Any amino acid or not present
<220> FEATURE:
<221> NAME/KEY: MOD_RES
<222> LOCATION: (97)..(97)
<223> OTHER INFORMATION: Any amino acid or not present
<220> FEATURE:
<221> NAME/KEY: MOD_RES
<222> LOCATION: (100)..(100)
<223> OTHER INFORMATION: Any amino acid or not present
```

```
<220> FEATURE:
<223> OTHER INFORMATION: See specification as filed for detailed
      description of substitutions and preferred embodiments

<400> SEQUENCE: 2

Ser Xaa Val Arg Pro Gln Pro Ser Leu Ser Val Ala Pro Gly Glu
1               5                   10                  15

Thr Ala Arg Ile Xaa Cys Gly Glu Xaa Ser Leu Gly Ser Arg Ala Val
            20                  25                  30

Gln Trp Tyr Gln Gln Arg Pro Gly Gln Ala Pro Ser Leu Ile Ile Tyr
        35                  40                  45

Asn Asn Gln Asp Arg Pro Ser Gly Ile Pro Glu Arg Phe Ser Gly Ser
50                  55                  60

Pro Asp Xaa Xaa Phe Gly Thr Thr Ala Thr Leu Thr Ile Thr Xaa Val
65              70                  75                  80

Glu Ala Gly Asp Glu Ala Asp Tyr Tyr Cys His Ile Trp Asp Ser Arg
                85                  90                  95

Xaa Pro Thr Xaa Trp Val Phe Gly Gly Gly Thr Thr Leu Thr Val Leu
            100                 105                 110

<210> SEQ ID NO 3
<211> LENGTH: 132
<212> TYPE: PRT
<213> ORGANISM: Homo sapiens

<400> SEQUENCE: 3

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Met Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60

Ser Arg Val His Leu Ser Leu Asp Lys Ser Asn Asn Leu Val Ser Leu
65                  70                  75                  80

Arg Leu Thr Ala Val Thr Ala Ala Asp Ser Ala Thr Tyr Tyr Cys Ala
                85                  90                  95

Thr Thr Lys His Gly Arg Arg Ile Tyr Gly Ile Val Ala Phe Asn Glu
            100                 105                 110

Trp Phe Thr Tyr Phe Tyr Met Asp Val Trp Gly Lys Gly Thr Thr Val
        115                 120                 125

Thr Val Ser Ser
    130

<210> SEQ ID NO 4
<211> LENGTH: 105
<212> TYPE: PRT
<213> ORGANISM: Homo sapiens

<400> SEQUENCE: 4

Ser Ser Met Ser Val Ser Pro Gly Glu Thr Ala Lys Ile Ser Cys Gly
1               5                   10                  15

Lys Glu Ser Ile Gly Ser Arg Ala Val Gln Trp Tyr Gln Gln Lys Ser
            20                  25                  30

Gly Gln Pro Pro Ser Leu Ile Ile Tyr Asn Asn Gln Asp Arg Pro Ser
        35                  40                  45
```

Gly Val Pro Glu Arg Phe Ser Ala Thr Pro Asp Phe Gly Ala Gly Thr
            50                  55                  60

Thr Ala Thr Leu Thr Ile Thr Asn Val Glu Ala Asp Asp Glu Ala Asp
 65                  70                  75                  80

Tyr Tyr Cys His Ile Tyr Asp Ala Arg Gly Gly Thr Asn Trp Val Phe
                 85                  90                  95

Asp Arg Gly Ala Thr Leu Thr Val Leu
            100                 105

<210> SEQ ID NO 5
<211> LENGTH: 132
<212> TYPE: PRT
<213> ORGANISM: Homo sapiens

<400> SEQUENCE: 5

Gln Val Gln Leu Gln Glu Ser Gly Pro Gly Leu Val Lys Pro Ser Glu
 1               5                  10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
         35                  40                  45

Gly Tyr Val His Lys Ser Gly Asp Thr Asn Tyr Ser Pro Ser Leu Lys
 50                  55                  60

Ser Arg Val Asn Leu Ser Leu Asp Thr Ser Lys Asn Gln Val Ser Leu
 65                  70                  75                  80

Ser Leu Val Ala Ala Thr Ala Ala Asp Ser Gly Lys Tyr Tyr Cys Ala
                 85                  90                  95

Arg Thr Leu His Gly Arg Arg Ile Tyr Gly Ile Val Ala Phe Asn Glu
             100                 105                 110

Trp Phe Thr Tyr Phe Tyr Met Asp Val Trp Gly Asn Gly Thr Gln Val
         115                 120                 125

Thr Val Ser Ser
     130

<210> SEQ ID NO 6
<211> LENGTH: 105
<212> TYPE: PRT
<213> ORGANISM: Homo sapiens

<400> SEQUENCE: 6

Ser Asp Ile Ser Val Ala Pro Gly Glu Thr Ala Arg Ile Ser Cys Gly
 1               5                  10                  15

Glu Lys Ser Leu Gly Ser Arg Ala Val Gln Trp Tyr Gln His Arg Ala
             20                  25                  30

Gly Gln Ala Pro Ser Leu Ile Ile Tyr Asn Asn Gln Asp Arg Pro Ser
         35                  40                  45

Gly Ile Pro Glu Arg Phe Ser Gly Ser Pro Asp Ser Pro Phe Gly Thr
 50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Val Pro Thr Lys Trp Val Phe
                 85                  90                  95

Gly Gly Gly Thr Thr Leu Thr Val Leu
             100                 105

<210> SEQ ID NO 7
<211> LENGTH: 132

<212> TYPE: PRT
<213> ORGANISM: Homo sapiens

<400> SEQUENCE: 7

Gln Val Gln Leu Gln Glu Ser Gly Pro Gly Leu Val Lys Pro Pro Glu
1               5                   10                  15

Thr Leu Ser Leu Thr Cys Ser Val Ser Gly Ala Ser Val Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Ala Leu Thr Ala Ala Asp Ser Ala Val Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
        115                 120                 125

Thr Val Ser Ser
    130

<210> SEQ ID NO 8
<211> LENGTH: 105
<212> TYPE: PRT
<213> ORGANISM: Homo sapiens

<400> SEQUENCE: 8

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Glu Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 9
<211> LENGTH: 132
<212> TYPE: PRT
<213> ORGANISM: Homo sapiens

<400> SEQUENCE: 9

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Ala Ser Ala Thr Tyr Asn Pro Ser Leu Asn

```
                    50                  55                  60
Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                     85                  90                  95

Thr Ala Arg Arg Gly Gln Arg Ile Tyr Gly Val Val Ser Phe Gly Glu
                100                 105                 110

Phe Phe Tyr Tyr Tyr Ser Met Asp Val Trp Gly Lys Gly Thr Thr Val
                115                 120                 125

Thr Val Ser Ser
            130

<210> SEQ ID NO 10
<211> LENGTH: 108
<212> TYPE: PRT
<213> ORGANISM: Homo sapiens

<400> SEQUENCE: 10

Ser Tyr Val Arg Pro Leu Ser Val Ala Leu Gly Glu Thr Ala Ser Ile
 1               5                  10                  15

Ser Cys Gly Arg Gln Ala Leu Gly Ser Arg Ala Val Gln Trp Tyr Gln
                20                  25                  30

His Arg Pro Gly Gln Ala Pro Ile Leu Leu Ile Tyr Asn Asn Gln Asp
                35                  40                  45

Arg Pro Ser Gly Ile Pro Glu Arg Phe Ser Gly Thr Pro Asp Ile Asn
 50                  55                  60

Phe Gly Thr Arg Ala Thr Leu Thr Ile Ser Gly Val Glu Ala Gly Asp
 65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
                100                 105

<210> SEQ ID NO 11
<211> LENGTH: 132
<212> TYPE: PRT
<213> ORGANISM: Homo sapiens

<400> SEQUENCE: 11

Gln Val Gln Leu Gln Glu Ser Gly Pro Gly Leu Val Lys Pro Ser Glu
 1               5                  10                  15

Thr Leu Ser Leu Thr Cys Ser Val Ser Asn Gly Ser Val Ser Gly Arg
                20                  25                  30

Phe Trp Ser Trp Ile Arg Gln Ser Pro Gly Arg Gly Leu Glu Trp Ile
                35                  40                  45

Gly Tyr Phe Ser Asp Thr Glu Lys Ser Asn Tyr Asn Pro Ser Leu Arg
             50                  55                  60

Ser Arg Leu Thr Leu Ser Val Asp Ala Ser Lys Asn Gln Leu Ser Leu
 65                  70                  75                  80

Lys Leu Asn Ser Val Thr Ala Ala Asp Ser Ala Thr Tyr Tyr Cys Ala
                85                  90                  95

Arg Thr Gln Gln Gly Lys Arg Ile Tyr Gly Val Val Ser Phe Gly Glu
                100                 105                 110

Phe Phe His Tyr Tyr Met Asp Ala Trp Gly Lys Gly Thr Ala Val
                115                 120                 125

Thr Val Ser Ser
```

<210> SEQ ID NO 12
<211> LENGTH: 107
<212> TYPE: PRT
<213> ORGANISM: Homo sapiens

<400> SEQUENCE: 12

Ser Ser Leu Pro Leu Ser Val Ala Pro Gly Ala Thr Ala Lys Ile Ala
1               5                   10                  15

Cys Gly Glu Lys Ser Phe Ala Ser Arg Ala Val Gln Trp Tyr Gln Gln
            20                  25                  30

Lys Pro Gly Gln Ala Pro Val Leu Ile Ile Tyr Asn Asn Gln Asp Arg
        35                  40                  45

Pro Ala Gly Val Ser Glu Arg Phe Ser Gly Thr Pro Asp Val Gly Phe
    50                  55                  60

Gly Ser Thr Ala Thr Leu Thr Ile Ser Arg Val Glu Ala Gly Asp Glu
65                  70                  75                  80

Ala Asp Tyr Tyr Cys His Lys Trp Asp Ser Arg Ser Pro Leu Ser Trp
                85                  90                  95

Val Phe Gly Gly Gly Thr Gln Leu Thr Val Leu
            100                 105

<210> SEQ ID NO 13
<211> LENGTH: 132
<212> TYPE: PRT
<213> ORGANISM: Homo sapiens

<400> SEQUENCE: 13

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
    130

<210> SEQ ID NO 14
<211> LENGTH: 108
<212> TYPE: PRT
<213> ORGANISM: Homo sapiens

<400> SEQUENCE: 14

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
            35                  40                  45

Arg Pro Ser Gly Ile Pro Glu Arg Phe Ser Gly Thr Pro Asp Ile Asn
 50                  55                  60

Phe Gly Thr Arg Ala Thr Leu Thr Ile Ser Gly Val Glu Ala Gly Asp
 65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 15
<211> LENGTH: 132
<212> TYPE: PRT
<213> ORGANISM: Homo sapiens

<400> SEQUENCE: 15

Gln Val Gln Leu Gln Glu Ser Gly Pro Gly Leu Val Lys Pro Glu
 1               5                  10                  15

Thr Leu Ser Leu Thr Cys Ser Val Ser Gly Ala Ser Ile Asn Asp Ala
                20                  25                  30

Tyr Trp Ser Trp Ile Arg Gln Ser Pro Gly Lys Arg Pro Glu Trp Val
            35                  40                  45

Gly Tyr Val His His Ser Gly Asp Thr Asn Tyr Asn Pro Ser Leu Lys
 50                  55                  60

Arg Arg Val Ser Phe Ser Leu Asp Thr Ala Lys Asn Glu Val Ser Leu
 65                  70                  75                  80

Lys Leu Val Asp Leu Thr Ala Ala Asp Ser Ala Ile Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
            115                 120                 125

Thr Val Ser Ser
    130

<210> SEQ ID NO 16
<211> LENGTH: 105
<212> TYPE: PRT
<213> ORGANISM: Homo sapiens

<400> SEQUENCE: 16

Ser Phe Val Ser Val Ala Pro Gly Gln Thr Ala Arg Ile Thr Cys Gly
 1               5                  10                  15

Glu Glu Ser Leu Gly Ser Arg Ser Val Ile Trp Tyr Gln Gln Arg Pro
                20                  25                  30

Gly Gln Ala Pro Ser Leu Ile Met Tyr Asn Asn His Asp Arg Pro Ser
            35                  40                  45

Gly Ile Pro Glu Arg Phe Ser Gly Ser Pro Gly Ser Thr Phe Gly Thr
 50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

```
<210> SEQ ID NO 17
<211> LENGTH: 132
<212> TYPE: PRT
<213> ORGANISM: Homo sapiens

<400> SEQUENCE: 17

Gln Val Gln Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Asp Leu Thr Ala Ala Asp Ser Ala Val Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Thr Val
        115                 120                 125

Thr Val Ser Ser
    130

<210> SEQ ID NO 18
<211> LENGTH: 105
<212> TYPE: PRT
<213> ORGANISM: Homo sapiens

<400> SEQUENCE: 18

Ser Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Glu Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Thr Val Leu
            100                 105

<210> SEQ ID NO 19
<211> LENGTH: 132
<212> TYPE: PRT
<213> ORGANISM: Homo sapiens

<400> SEQUENCE: 19

Gln Val Gln Leu Val Glu Ser Gly Pro Gly Leu Val Thr Pro Ser Glu
1               5                   10                  15

Thr Leu Ser Leu Thr Cys Thr Val Ser Asn Gly Ser Val Ser Gly Arg
            20                  25                  30
```

```
Phe Trp Ser Trp Ile Arg Gln Ser Pro Gly Arg Gly Leu Glu Trp Ile
            35                  40                  45

Gly Tyr Phe Ser Asp Thr Asp Arg Ser Glu Tyr Ser Pro Ser Leu Arg
 50                      55                  60

Ser Arg Leu Thr Leu Ser Leu Asp Ala Ser Arg Asn Gln Leu Ser Leu
 65                  70                  75                  80

Lys Leu Lys Ser Val Thr Ala Ala Asp Ser Ala Thr Tyr Tyr Cys Ala
                 85                  90                  95

Arg Ala Gln Gln Gly Lys Arg Ile Tyr Gly Ile Val Ser Phe Gly Glu
                100                 105                 110

Phe Phe Tyr Tyr Tyr Met Asp Ala Trp Gly Lys Gly Thr Ala Val
            115                 120                 125

Thr Val Ser Ser
        130

<210> SEQ ID NO 20
<211> LENGTH: 107
<212> TYPE: PRT
<213> ORGANISM: Homo sapiens

<400> SEQUENCE: 20

Ser Ser Leu Pro Leu Ser Leu Ala Pro Gly Ala Thr Ala Lys Ile Pro
 1               5                  10                  15

Cys Gly Glu Lys Ser Arg Gly Ser Arg Ala Val Gln Trp Tyr Gln Gln
                20                  25                  30

Lys Pro Gly Gln Ala Pro Thr Leu Ile Ile Tyr Asn Asn Gln Asp Arg
            35                  40                  45

Pro Ala Gly Val Ser Glu Arg Tyr Ser Gly Asn Pro Asp Val Ala Ile
 50                      55                  60

Gly Val Thr Ala Thr Leu Thr Ile Ser Arg Val Glu Ala Gly Asp Glu
 65                  70                  75                  80

Ala Glu Tyr Tyr Cys His Tyr Trp Asp Ser Arg Ser Pro Ile Ser Trp
                 85                  90                  95

Val Phe Gly Gly Trp Thr Gln Leu Thr Val Leu
                100                 105

<210> SEQ ID NO 21
<211> LENGTH: 132
<212> TYPE: PRT
<213> ORGANISM: Homo sapiens

<400> SEQUENCE: 21

Gln Val Gln Leu Gln Glu Ser Gly Pro Gly Leu Val Lys Pro Ser Glu
 1               5                  10                  15

Thr Leu Ser Val Thr Cys Ser Val Ser Gly Asp Ser Met Asn Asn Tyr
                20                  25                  30

Tyr Trp Thr Trp Ile Arg Gln Ser Pro Gly Lys Gly Leu Glu Trp Ile
            35                  40                  45

Gly Tyr Ile Ser Asp Arg Glu Ser Ala Thr Tyr Asn Pro Ser Leu Asn
 50                      55                  60

Ser Arg Val Val Ile Ser Arg Asp Thr Ser Thr Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg Arg Gly Gln Arg Ile Tyr Gly Val Val Ser Phe Gly Glu
                100                 105                 110
```

Phe Phe Tyr Tyr Tyr Ser Met Asp Val Trp Gly Arg Gly Thr Thr Val
            115                 120                 125

Thr Val Ser Ser
        130

<210> SEQ ID NO 22
<211> LENGTH: 108
<212> TYPE: PRT
<213> ORGANISM: Homo sapiens

<400> SEQUENCE: 22

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
    50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 23
<211> LENGTH: 132
<212> TYPE: PRT
<213> ORGANISM: Homo sapiens

<400> SEQUENCE: 23

Gln Val Gln Leu Gln Glu Ser Gly Pro Gly Leu Val Lys Pro Leu Glu
1               5                   10                  15

Thr Leu Ser Leu Thr Cys Asn Val Ser Gly Ala Phe Ile Ala Asp His
            20                  25                  30

Tyr Trp Ser Trp Ile Arg Leu Pro Leu Gly Lys Gly Pro Glu Trp Ile
        35                  40                  45

Gly Tyr Val His Asp Ser Gly Asp Ile Asn Tyr Asn Pro Ser Leu Lys
    50                  55                  60

Asn Arg Val His Leu Ser Leu Asp Lys Ser Thr Asn Gln Val Ser Leu
65                  70                  75                  80

Lys Leu Met Ala Val Thr Ala Gly Asp Ser Ala Leu Tyr Tyr Cys Ala
                85                  90                  95

Thr Thr Lys His Gly Arg Arg Ile Tyr Gly Val Val Ala Phe Gly Glu
            100                 105                 110

Trp Phe Thr Tyr Phe Tyr Met Asp Val Trp Gly Arg Gly Thr Thr Val
        115                 120                 125

Thr Val Ser Ser
    130

<210> SEQ ID NO 24
<211> LENGTH: 105
<212> TYPE: PRT
<213> ORGANISM: Homo sapiens

<400> SEQUENCE: 24

Ser Ser Met Ser Val Ser Pro Gly Glu Thr Ala Lys Ile Thr Cys Gly

```
                1               5                   10                  15
            Glu Lys Ser Ile Gly Ser Arg Ala Val Gln Trp Tyr Gln Lys Lys Pro
                            20                  25                  30
            Gly Gln Pro Pro Ser Leu Ile Ile Tyr Asn Asn Gln Asp Arg Pro Ser
                        35                  40                  45
            Gly Val Pro Glu Arg Phe Ser Ala Ser Pro Asp Ile Glu Phe Gly Thr
                    50                  55                  60
            Thr Ala Thr Leu Thr Ile Thr Asn Val Glu Ala Gly Asp Glu Ala Asp
            65                  70                  75                  80
            Tyr Tyr Cys His Ile Tyr Asp Ala Arg Arg Pro Thr Asn Trp Val Phe
                            85                  90                  95
            Asp Arg Gly Thr Thr Leu Thr Val Leu
                        100                 105

<210> SEQ ID NO 25
<211> LENGTH: 132
<212> TYPE: PRT
<213> ORGANISM: Homo sapiens

<400> SEQUENCE: 25

Gln Val Gln Leu Gln Glu Ser Gly Pro Gly Leu Val Lys Pro Ser Glu
            1               5                   10                  15
            Thr Leu Ser Leu Thr Cys Ser Val Ser Gly Ala Ser Ile Ser Asp Ser
                            20                  25                  30
            Tyr Trp Ser Trp Ile Arg Arg Ser Pro Gly Lys Gly Leu Glu Trp Ile
                        35                  40                  45
            Gly Tyr Val His Lys Ser Gly Asp Thr Asn Tyr Ser Pro Ser Leu Lys
                    50                  55                  60
            Ser Arg Val Asn Leu Ser Leu Asp Thr Ser Lys Asn Gln Val Ser Leu
            65                  70                  75                  80
            Ser Leu Val Ala Ala Thr Ala Ala Asp Ser Gly Lys Tyr Tyr Cys Ala
                            85                  90                  95
            Arg Thr Leu His Gly Arg Arg Ile Tyr Gly Ile Val Ala Phe Asn Glu
                        100                 105                 110
            Trp Phe Thr Tyr Phe Tyr Met Asp Val Trp Gly Asn Gly Thr Gln Val
                    115                 120                 125
            Thr Val Ser Ser
                130

<210> SEQ ID NO 26
<211> LENGTH: 105
<212> TYPE: PRT
<213> ORGANISM: Homo sapiens

<400> SEQUENCE: 26

Ser Asp Ile Ser Val Ala Pro Gly Glu Thr Ala Arg Ile Ser Cys Gly
            1               5                   10                  15
            Glu Lys Ser Leu Gly Ser Arg Ala Val Gln Trp Tyr Gln His Arg Ala
                            20                  25                  30
            Gly Gln Ala Pro Ser Leu Ile Ile Tyr Asn Asn Gln Asp Arg Pro Ser
                        35                  40                  45
            Gly Ile Pro Glu Arg Phe Ser Gly Ser Pro Asp Ser Pro Phe Gly Thr
                    50                  55                  60
            Thr Ala Thr Leu Thr Ile Thr Ser Val Glu Ala Gly Asp Glu Ala Asp
            65                  70                  75                  80
            Tyr Tyr Cys His Ile Trp Asp Ser Arg Val Pro Thr Lys Trp Val Phe
```

```
                    85                  90                  95

Gly Gly Gly Thr Thr Leu Thr Val Leu
            100                 105

<210> SEQ ID NO 27
<211> LENGTH: 132
<212> TYPE: PRT
<213> ORGANISM: Homo sapiens

<400> SEQUENCE: 27

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Ile Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60

Ser Arg Val His Leu Ser Leu Asp Lys Ser Lys Asn Leu Val Ser Leu
65                  70                  75                  80

Arg Leu Thr Gly Val Thr Ala Ala Asp Ser Ala Ile Tyr Tyr Cys Ala
                85                  90                  95

Thr Thr Lys His Gly Arg Arg Ile Tyr Gly Val Val Ala Phe Lys Glu
            100                 105                 110

Trp Phe Thr Tyr Phe Tyr Met Asp Val Trp Gly Lys Gly Thr Ser Val
        115                 120                 125

Thr Val Ser Ser
    130

<210> SEQ ID NO 28
<211> LENGTH: 105
<212> TYPE: PRT
<213> ORGANISM: Homo sapiens

<400> SEQUENCE: 28

Thr Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Asp Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Ile Val Leu
            100                 105

<210> SEQ ID NO 29
<211> LENGTH: 132
<212> TYPE: PRT
<213> ORGANISM: Homo sapiens

<400> SEQUENCE: 29

Gln Leu His Leu Gln Glu Ser Gly Pro Gly Leu Val Lys Pro Pro Glu
1               5                   10                  15
```

-continued

Thr Leu Ser Leu Thr Cys Ser Val Ser Gly Ala Ser Ile Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Asp Leu Thr Ala Ala Asp Ser Ala Thr Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Ala Val
        115                 120                 125

Thr Val Ser Ser
        130

<210> SEQ ID NO 30
<211> LENGTH: 105
<212> TYPE: PRT
<213> ORGANISM: Homo sapiens

<400> SEQUENCE: 30

Ser Ser Met Ser Val Ser Pro Gly Glu Thr Ala Lys Ile Ser Cys Gly
1               5                   10                  15

Lys Glu Ser Ile Gly Ser Arg Ala Val Gln Trp Tyr Gln Gln Lys Pro
            20                  25                  30

Gly Gln Pro Pro Ser Leu Ile Ile Tyr Asn Asn Gln Asp Arg Pro Ala
        35                  40                  45

Gly Val Pro Glu Arg Phe Ser Ala Ser Pro Asp Phe Arg Pro Gly Thr
    50                  55                  60

Thr Ala Thr Leu Thr Ile Thr Asn Val Asp Ala Glu Asp Glu Ala Asp
65                  70                  75                  80

Tyr Tyr Cys His Ile Tyr Asp Ala Arg Gly Gly Thr Asn Trp Val Phe
                85                  90                  95

Asp Arg Gly Thr Thr Leu Thr Val Leu
            100                 105

<210> SEQ ID NO 31
<211> LENGTH: 132
<212> TYPE: PRT
<213> ORGANISM: Homo sapiens

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

```
Arg Thr Gln Gln Gly Lys Arg Ile Tyr Gly Val Val Ser Phe Gly Asp
            100                 105                 110

Tyr Tyr Tyr Tyr Tyr Met Asp Val Trp Gly Lys Gly Thr Thr Val
        115                 120                 125

Thr Val Ser Ser
    130

<210> SEQ ID NO 32
<211> LENGTH: 109
<212> TYPE: PRT
<213> ORGANISM: Homo sapiens

<400> SEQUENCE: 32

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Trp Val Phe Gly Gly Gly Thr Lys Leu Thr Val Leu
            100                 105

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid or not present

<400> SEQUENCE: 33

Asp Xaa Tyr Trp Ser
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Val His Asp Ser Gly Asp Thr Asn Tyr Asn Pro Ser Leu Lys Ser
1               5                   10                  15

<210> SEQ ID NO 35
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Any amino acid or not present
<220> FEATURE:
<221> NAME/KEY: MOD_RES
<222> LOCATION: (5)..(5)
<223> OTHER INFORMATION: Any amino acid or not present
<220> FEATURE:
<221> NAME/KEY: MOD_RES
<222> LOCATION: (16)..(16)
<223> OTHER INFORMATION: Any amino acid or not present

<400> SEQUENCE: 35

Ala Xaa His Gly Xaa Arg Ile Tyr Gly Ile Val Ala Phe Gly Glu Xaa
1               5                   10                  15

Phe Thr Tyr Phe Tyr Met Asp Val
            20

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid or not present

<400> SEQUENCE: 36

Gly Glu Xaa Ser Leu Gly Ser Arg Ala Val Gln
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn Asn Gln Asp Arg Pro Ser
1               5

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid or not present
<220> FEATURE:
<221> NAME/KEY: MOD_RES
<222> LOCATION: (10)..(10)
<223> OTHER INFORMATION: Any amino acid or not present

<400> SEQUENCE: 38

His Ile Trp Asp Ser Arg Xaa Pro Thr Xaa Trp Val
1               5                   10

<210> SEQ ID NO 39
<211> LENGTH: 5
<212> TYPE: PRT
```

```
<213> ORGANISM: Homo sapiens

<400> SEQUENCE: 39

Asp Asn Tyr Trp Ser
1               5

<210> SEQ ID NO 40
<211> LENGTH: 16
<212> TYPE: PRT
<213> ORGANISM: Homo sapiens

<400> SEQUENCE: 40

Tyr Val His Asp Ser Gly Asp Thr Asn Tyr Asn Pro Ser Leu Lys Ser
1               5                   10                  15

<210> SEQ ID NO 41
<211> LENGTH: 24
<212> TYPE: PRT
<213> ORGANISM: Homo sapiens

<400> SEQUENCE: 41

Thr Lys His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 42
<211> LENGTH: 11
<212> TYPE: PRT
<213> ORGANISM: Homo sapiens

<400> SEQUENCE: 42

Gly Lys Glu Ser Ile Gly Ser Arg Ala Val Gln
1               5                   10

<210> SEQ ID NO 43
<211> LENGTH: 7
<212> TYPE: PRT
<213> ORGANISM: Homo sapiens

<400> SEQUENCE: 43

Asn Asn Gln Asp Arg Pro Ser
1               5

<210> SEQ ID NO 44
<211> LENGTH: 12
<212> TYPE: PRT
<213> ORGANISM: Homo sapiens

<400> SEQUENCE: 44

His Ile Tyr Asp Ala Arg Gly Gly Thr Asn Trp Val
1               5                   10

<210> SEQ ID NO 45
<211> LENGTH: 5
<212> TYPE: PRT
<213> ORGANISM: Homo sapiens

<400> SEQUENCE: 45

Asp Ser Tyr Trp Ser
1               5

<210> SEQ ID NO 46
<211> LENGTH: 16
```

```
<212> TYPE: PRT
<213> ORGANISM: Homo sapiens

<400> SEQUENCE: 46

Tyr Val His Lys Ser Gly Asp Thr Asn Tyr Ser Pro Ser Leu Lys Ser
1               5                   10                  15

<210> SEQ ID NO 47
<211> LENGTH: 24
<212> TYPE: PRT
<213> ORGANISM: Homo sapiens

<400> SEQUENCE: 47

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 48
<211> LENGTH: 11
<212> TYPE: PRT
<213> ORGANISM: Homo sapiens

<400> SEQUENCE: 48

Gly Glu Lys Ser Leu Gly Ser Arg Ala Val Gln
1               5                   10

<210> SEQ ID NO 49
<211> LENGTH: 7
<212> TYPE: PRT
<213> ORGANISM: Homo sapiens

<400> SEQUENCE: 49

Asn Asn Gln Asp Arg Pro Ser
1               5

<210> SEQ ID NO 50
<211> LENGTH: 12
<212> TYPE: PRT
<213> ORGANISM: Homo sapiens

<400> SEQUENCE: 50

His Ile Trp Asp Ser Arg Val Pro Thr Lys Trp Val
1               5                   10

<210> SEQ ID NO 51
<211> LENGTH: 5
<212> TYPE: PRT
<213> ORGANISM: Homo sapiens

<400> SEQUENCE: 51

Asp Ala Tyr Trp Ser
1               5

<210> SEQ ID NO 52
<211> LENGTH: 16
<212> TYPE: PRT
<213> ORGANISM: Homo sapiens

<400> SEQUENCE: 52

Tyr Val His His Ser Gly Asp Thr Asn Tyr Asn Pro Ser Leu Lys Arg
1               5                   10                  15

<210> SEQ ID NO 53
```

```
<211> LENGTH: 24
<212> TYPE: PRT
<213> ORGANISM: Homo sapiens

<400> SEQUENCE: 53

Ala Leu His Gly Lys Arg Ile Tyr Gly Ile Val Ala Leu Gly Glu Leu
1               5                   10                  15

Phe Thr Tyr Phe Tyr Met Asp Val
            20

<210> SEQ ID NO 54
<211> LENGTH: 11
<212> TYPE: PRT
<213> ORGANISM: Homo sapiens

<400> SEQUENCE: 54

Gly Glu Glu Ser Leu Gly Ser Arg Ser Val Ile
1               5                   10

<210> SEQ ID NO 55
<211> LENGTH: 7
<212> TYPE: PRT
<213> ORGANISM: Homo sapiens

<400> SEQUENCE: 55

Asn Asn Asn Asp Arg Pro Ser
1               5

<210> SEQ ID NO 56
<211> LENGTH: 12
<212> TYPE: PRT
<213> ORGANISM: Homo sapiens

<400> SEQUENCE: 56

His Ile Trp Asp Ser Arg Arg Pro Thr Asn Trp Val
1               5                   10

<210> SEQ ID NO 57
<211> LENGTH: 5
<212> TYPE: PRT
<213> ORGANISM: Homo sapiens

<400> SEQUENCE: 57

Asn Tyr Tyr Trp Thr
1               5

<210> SEQ ID NO 58
<211> LENGTH: 16
<212> TYPE: PRT
<213> ORGANISM: Homo sapiens

<400> SEQUENCE: 58

Tyr Ile Ser Asp Arg Ala Ser Ala Thr Tyr Asn Pro Ser Leu Asn Ser
1               5                   10                  15

<210> SEQ ID NO 59
<211> LENGTH: 24
<212> TYPE: PRT
<213> ORGANISM: Homo sapiens

<400> SEQUENCE: 59

Ala Arg Arg Gly Gln Arg Ile Tyr Gly Val Val Ser Phe Gly Glu Phe
1               5                   10                  15

Phe Tyr Tyr Tyr Ser Met Asp Val
```

-continued

<210> SEQ ID NO 60
<211> LENGTH: 11
<212> TYPE: PRT
<213> ORGANISM: Homo sapiens

<400> SEQUENCE: 60

Gly Arg Gln Ala Leu Gly Ser Arg Ala Val Gln
1               5                   10

<210> SEQ ID NO 61
<211> LENGTH: 7
<212> TYPE: PRT
<213> ORGANISM: Homo sapiens

<400> SEQUENCE: 61

Asn Asn Gln Asp Arg Pro Ser
1               5

<210> SEQ ID NO 62
<211> LENGTH: 12
<212> TYPE: PRT
<213> ORGANISM: Homo sapiens

<400> SEQUENCE: 62

His Met Trp Asp Ser Arg Ser Gly Phe Ser Trp Ser
1               5                   10

<210> SEQ ID NO 63
<211> LENGTH: 5
<212> TYPE: PRT
<213> ORGANISM: Homo sapiens

<400> SEQUENCE: 63

Gly Arg Phe Trp Ser
1               5

<210> SEQ ID NO 64
<211> LENGTH: 16
<212> TYPE: PRT
<213> ORGANISM: Homo sapiens

<400> SEQUENCE: 64

Tyr Phe Ser Asp Thr Glu Lys Ser Asn Tyr Asn Pro Ser Leu Arg Ser
1               5                   10                  15

<210> SEQ ID NO 65
<211> LENGTH: 24
<212> TYPE: PRT
<213> ORGANISM: Homo sapiens

<400> SEQUENCE: 65

Thr Gln Gln Gly Lys Arg Ile Tyr Gly Val Val Ser Phe Gly Glu Phe
1               5                   10                  15

Phe His Tyr Tyr Tyr Met Asp Ala
            20

<210> SEQ ID NO 66
<211> LENGTH: 11
<212> TYPE: PRT
<213> ORGANISM: Homo sapiens

<400> SEQUENCE: 66

Gly Glu Lys Ser Phe Ala Ser Arg Ala Val Gln
1               5                   10

<210> SEQ ID NO 67
<211> LENGTH: 7
<212> TYPE: PRT
<213> ORGANISM: Homo sapiens

<400> SEQUENCE: 67

Asn Asn Gln Asp Arg Pro Ala
1               5

<210> SEQ ID NO 68
<211> LENGTH: 12
<212> TYPE: PRT
<213> ORGANISM: Homo sapiens

<400> SEQUENCE: 68

His Lys Trp Asp Ser Arg Ser Pro Leu Ser Trp Val
1               5                   10

<210> SEQ ID NO 69
<211> LENGTH: 5
<212> TYPE: PRT
<213> ORGANISM: Homo sapiens

<400> SEQUENCE: 69

Asn Tyr Tyr Trp Thr
1               5

<210> SEQ ID NO 70
<211> LENGTH: 16
<212> TYPE: PRT
<213> ORGANISM: Homo sapiens

<400> SEQUENCE: 70

Tyr Ile Ser Asp Arg Glu Ser Ala Thr Tyr Asn Pro Ser Leu Asn Ser
1               5                   10                  15

<210> SEQ ID NO 71
<211> LENGTH: 24
<212> TYPE: PRT
<213> ORGANISM: Homo sapiens

<400> SEQUENCE: 71

Ala Arg Arg Gly Gln Arg Ile Tyr Gly Val Val Ser Phe Gly Glu Phe
1               5                   10                  15
Phe Tyr Tyr Tyr Ser Met Asp Val
            20

<210> SEQ ID NO 72
<211> LENGTH: 11
<212> TYPE: PRT
<213> ORGANISM: Homo sapiens

<400> SEQUENCE: 72

Gly Arg Gln Ala Leu Gly Ser Arg Ala Val Gln
1               5                   10

<210> SEQ ID NO 73
<211> LENGTH: 7
<212> TYPE: PRT
<213> ORGANISM: Homo sapiens

<400> SEQUENCE: 73

Asn Asn Gln Asp Arg Pro Ser
1               5

<210> SEQ ID NO 74
<211> LENGTH: 12
<212> TYPE: PRT
<213> ORGANISM: Homo sapiens

<400> SEQUENCE: 74

His Met Trp Asp Ser Arg Ser Gly Phe Ser Trp Ser
1               5                   10

<210> SEQ ID NO 75
<211> LENGTH: 5
<212> TYPE: PRT
<213> ORGANISM: Homo sapiens

<400> SEQUENCE: 75

Asp Ala Tyr Trp Ser
1               5

<210> SEQ ID NO 76
<211> LENGTH: 16
<212> TYPE: PRT
<213> ORGANISM: Homo sapiens

<400> SEQUENCE: 76

Tyr Val His His Ser Gly Asp Thr Asn Tyr Asn Pro Ser Leu Lys Arg
1               5                   10                  15

<210> SEQ ID NO 77
<211> LENGTH: 24
<212> TYPE: PRT
<213> ORGANISM: Homo sapiens

<400> SEQUENCE: 77

Ala Leu His Gly Lys Arg Ile Tyr Gly Ile Val Ala Leu Gly Glu Leu
1               5                   10                  15

Phe Thr Tyr Phe Tyr Met Asp Val
            20

<210> SEQ ID NO 78
<211> LENGTH: 11
<212> TYPE: PRT
<213> ORGANISM: Homo sapiens

<400> SEQUENCE: 78

Gly Glu Glu Ser Leu Gly Ser Arg Ser Val Ile
1               5                   10

<210> SEQ ID NO 79
<211> LENGTH: 7
<212> TYPE: PRT
<213> ORGANISM: Homo sapiens

<400> SEQUENCE: 79

Asn Asn His Asp Arg Pro Ser
1               5

<210> SEQ ID NO 80
<211> LENGTH: 12
<212> TYPE: PRT
<213> ORGANISM: Homo sapiens

```
<400> SEQUENCE: 80

His Ile Trp Asp Ser Arg Arg Pro Thr Asn Trp Val
1               5                   10

<210> SEQ ID NO 81
<211> LENGTH: 5
<212> TYPE: PRT
<213> ORGANISM: Homo sapiens

<400> SEQUENCE: 81

Asp Ala Tyr Trp Ser
1               5

<210> SEQ ID NO 82
<211> LENGTH: 16
<212> TYPE: PRT
<213> ORGANISM: Homo sapiens

<400> SEQUENCE: 82

Tyr Val His His Ser Gly Asp Thr Asn Tyr Asn Pro Ser Leu Lys Arg
1               5                   10                  15

<210> SEQ ID NO 83
<211> LENGTH: 24
<212> TYPE: PRT
<213> ORGANISM: Homo sapiens

<400> SEQUENCE: 83

Ala Leu His Gly Lys Arg Ile Tyr Gly Ile Val Ala Leu Gly Glu Leu
1               5                   10                  15

Phe Thr Tyr Phe Tyr Met Asp Val
            20

<210> SEQ ID NO 84
<211> LENGTH: 11
<212> TYPE: PRT
<213> ORGANISM: Homo sapiens

<400> SEQUENCE: 84

Gly Glu Glu Ser Leu Gly Ser Arg Ser Val Ile
1               5                   10

<210> SEQ ID NO 85
<211> LENGTH: 7
<212> TYPE: PRT
<213> ORGANISM: Homo sapiens

<400> SEQUENCE: 85

Asn Asn Asn Asp Arg Pro Ser
1               5

<210> SEQ ID NO 86
<211> LENGTH: 12
<212> TYPE: PRT
<213> ORGANISM: Homo sapiens

<400> SEQUENCE: 86

His Ile Trp Asp Ser Arg Arg Pro Thr Asn Trp Val
1               5                   10

<210> SEQ ID NO 87
<211> LENGTH: 5
<212> TYPE: PRT
<213> ORGANISM: Homo sapiens
```

<400> SEQUENCE: 87

Gly Arg Phe Trp Ser
1               5

<210> SEQ ID NO 88
<211> LENGTH: 16
<212> TYPE: PRT
<213> ORGANISM: Homo sapiens

<400> SEQUENCE: 88

Tyr Phe Ser Asp Thr Asp Arg Ser Glu Tyr Ser Pro Ser Leu Arg Ser
1               5                   10                  15

<210> SEQ ID NO 89
<211> LENGTH: 24
<212> TYPE: PRT
<213> ORGANISM: Homo sapiens

<400> SEQUENCE: 89

Ala Gln Gln Gly Lys Arg Ile Tyr Gly Ile Val Ser Phe Gly Glu Phe
1               5                   10                  15

Phe Tyr Tyr Tyr Tyr Met Asp Ala
            20

<210> SEQ ID NO 90
<211> LENGTH: 11
<212> TYPE: PRT
<213> ORGANISM: Homo sapiens

<400> SEQUENCE: 90

Gly Glu Lys Ser Arg Gly Ser Arg Ala Val Gln
1               5                   10

<210> SEQ ID NO 91
<211> LENGTH: 7
<212> TYPE: PRT
<213> ORGANISM: Homo sapiens

<400> SEQUENCE: 91

Asn Asn Gln Asp Arg Pro Ala
1               5

<210> SEQ ID NO 92
<211> LENGTH: 12
<212> TYPE: PRT
<213> ORGANISM: Homo sapiens

<400> SEQUENCE: 92

His Tyr Trp Asp Ser Arg Ser Pro Ile Ser Trp Val
1               5                   10

<210> SEQ ID NO 93
<211> LENGTH: 5
<212> TYPE: PRT
<213> ORGANISM: Homo sapiens

<400> SEQUENCE: 93

Asn Tyr Tyr Trp Thr
1               5

<210> SEQ ID NO 94
<211> LENGTH: 16
<212> TYPE: PRT

-continued

<213> ORGANISM: Homo sapiens

<400> SEQUENCE: 94

Tyr Ile Ser Asp Arg Glu Ser Ala Thr Tyr Asn Pro Ser Leu Asn Ser
1               5                   10                  15

<210> SEQ ID NO 95
<211> LENGTH: 24
<212> TYPE: PRT
<213> ORGANISM: Homo sapiens

<400> SEQUENCE: 95

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 96
<211> LENGTH: 11
<212> TYPE: PRT
<213> ORGANISM: Homo sapiens

<400> SEQUENCE: 96

Gly Arg Gln Ala Leu Gly Ser Arg Ala Val Gln
1               5                   10

<210> SEQ ID NO 97
<211> LENGTH: 7
<212> TYPE: PRT
<213> ORGANISM: Homo sapiens

<400> SEQUENCE: 97

Asn Asn Gln Asp Arg Pro Ser
1               5

<210> SEQ ID NO 98
<211> LENGTH: 12
<212> TYPE: PRT
<213> ORGANISM: Homo sapiens

<400> SEQUENCE: 98

His Met Trp Asp Ser Arg Ser Gly Phe Ser Trp Ser
1               5                   10

<210> SEQ ID NO 99
<211> LENGTH: 5
<212> TYPE: PRT
<213> ORGANISM: Homo sapiens

<400> SEQUENCE: 99

Asp His Tyr Trp Ser
1               5

<210> SEQ ID NO 100
<211> LENGTH: 16
<212> TYPE: PRT
<213> ORGANISM: Homo sapiens

<400> SEQUENCE: 100

Tyr Val His Asp Ser Gly Asp Ile Asn Tyr Asn Pro Ser Leu Lys Asn
1               5                   10                  15

<210> SEQ ID NO 101
<211> LENGTH: 24

<212> TYPE: PRT
<213> ORGANISM: Homo sapiens

<400> SEQUENCE: 101

Thr Lys His Gly Arg Arg Ile Tyr Gly Val Val Ala Phe Gly Glu Trp
1               5                   10                  15

Phe Thr Tyr Phe Tyr Met Asp Val
            20

<210> SEQ ID NO 102
<211> LENGTH: 11
<212> TYPE: PRT
<213> ORGANISM: Homo sapiens

<400> SEQUENCE: 102

Gly Glu Lys Ser Ile Gly Ser Arg Ala Val Gln
1               5                   10

<210> SEQ ID NO 103
<211> LENGTH: 7
<212> TYPE: PRT
<213> ORGANISM: Homo sapiens

<400> SEQUENCE: 103

Asn Asn Gln Asp Arg Pro Ser
1               5

<210> SEQ ID NO 104
<211> LENGTH: 12
<212> TYPE: PRT
<213> ORGANISM: Homo sapiens

<400> SEQUENCE: 104

His Ile Tyr Asp Ala Arg Arg Pro Thr Asn Trp Val
1               5                   10

<210> SEQ ID NO 105
<211> LENGTH: 5
<212> TYPE: PRT
<213> ORGANISM: Homo sapiens

<400> SEQUENCE: 105

Asp Ser Tyr Trp Ser
1               5

<210> SEQ ID NO 106
<211> LENGTH: 16
<212> TYPE: PRT
<213> ORGANISM: Homo sapiens

<400> SEQUENCE: 106

Tyr Val His Lys Ser Gly Asp Thr Asn Tyr Ser Pro Ser Leu Lys Ser
1               5                   10                  15

<210> SEQ ID NO 107
<211> LENGTH: 24
<212> TYPE: PRT
<213> ORGANISM: Homo sapiens

<400> SEQUENCE: 107

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 108
<211> LENGTH: 11
<212> TYPE: PRT
<213> ORGANISM: Homo sapiens

<400> SEQUENCE: 108

Gly Glu Lys Ser Leu Gly Ser Arg Ala Val Gln
1               5                   10

<210> SEQ ID NO 109
<211> LENGTH: 7
<212> TYPE: PRT
<213> ORGANISM: Homo sapiens

<400> SEQUENCE: 109

Asn Asn Gln Asp Arg Pro Ser
1               5

<210> SEQ ID NO 110
<211> LENGTH: 12
<212> TYPE: PRT
<213> ORGANISM: Homo sapiens

<400> SEQUENCE: 110

His Ile Trp Asp Ser Arg Val Pro Thr Lys Trp Val
1               5                   10

<210> SEQ ID NO 111
<211> LENGTH: 5
<212> TYPE: PRT
<213> ORGANISM: Homo sapiens

<400> SEQUENCE: 111

Asp Asn Tyr Trp Ser
1               5

<210> SEQ ID NO 112
<211> LENGTH: 16
<212> TYPE: PRT
<213> ORGANISM: Homo sapiens

<400> SEQUENCE: 112

Tyr Val His Asp Ser Gly Asp Thr Asn Tyr Asn Pro Ser Leu Lys Ser
1               5                   10                  15

<210> SEQ ID NO 113
<211> LENGTH: 24
<212> TYPE: PRT
<213> ORGANISM: Homo sapiens

<400> SEQUENCE: 113

Thr Lys His Gly Arg Arg Ile Tyr Gly Val Val Ala Phe Lys Glu Trp
1               5                   10                  15

Phe Thr Tyr Phe Tyr Met Asp Val
            20

<210> SEQ ID NO 114
<211> LENGTH: 11
<212> TYPE: PRT
<213> ORGANISM: Homo sapiens

<400> SEQUENCE: 114

Gly Glu Glu Ser Leu Gly Ser Arg Ser Val Ile

-continued

```
<210> SEQ ID NO 115
<211> LENGTH: 7
<212> TYPE: PRT
<213> ORGANISM: Homo sapiens

<400> SEQUENCE: 115

Asn Asn Asn Asp Arg Pro Ser
1               5

<210> SEQ ID NO 116
<211> LENGTH: 12
<212> TYPE: PRT
<213> ORGANISM: Homo sapiens

<400> SEQUENCE: 116

His Ile Trp Asp Ser Arg Arg Pro Thr Asn Trp Val
1               5                   10

<210> SEQ ID NO 117
<211> LENGTH: 5
<212> TYPE: PRT
<213> ORGANISM: Homo sapiens

<400> SEQUENCE: 117

Asp Ala Tyr Trp Ser
1               5

<210> SEQ ID NO 118
<211> LENGTH: 16
<212> TYPE: PRT
<213> ORGANISM: Homo sapiens

<400> SEQUENCE: 118

Tyr Val His His Ser Gly Asp Thr Asn Tyr Asn Pro Ser Leu Lys Arg
1               5                   10                  15

<210> SEQ ID NO 119
<211> LENGTH: 24
<212> TYPE: PRT
<213> ORGANISM: Homo sapiens

<400> SEQUENCE: 119

Ala Leu His Gly Lys Arg Ile Tyr Gly Ile Val Ala Leu Gly Glu Leu
1               5                   10                  15

Phe Thr Tyr Phe Tyr Met Asp Val
            20

<210> SEQ ID NO 120
<211> LENGTH: 11
<212> TYPE: PRT
<213> ORGANISM: Homo sapiens

<400> SEQUENCE: 120

Gly Lys Glu Ser Ile Gly Ser Arg Ala Val Gln
1               5                   10

<210> SEQ ID NO 121
<211> LENGTH: 7
<212> TYPE: PRT
<213> ORGANISM: Homo sapiens

<400> SEQUENCE: 121
```

Asn Asn Gln Asp Arg Pro Ala
1               5

<210> SEQ ID NO 122
<211> LENGTH: 12
<212> TYPE: PRT
<213> ORGANISM: Homo sapiens

<400> SEQUENCE: 122

His Ile Tyr Asp Ala Arg Gly Gly Thr Asn Trp Val
1               5                   10

<210> SEQ ID NO 123
<211> LENGTH: 5
<212> TYPE: PRT
<213> ORGANISM: Homo sapiens

<400> SEQUENCE: 123

Ser Tyr Tyr Trp Ser
1               5

<210> SEQ ID NO 124
<211> LENGTH: 16
<212> TYPE: PRT
<213> ORGANISM: Homo sapiens

<400> SEQUENCE: 124

Tyr Ile Tyr Tyr Ser Gly Ser Thr Asn Tyr Asn Pro Ser Leu Lys Ser
1               5                   10                  15

<210> SEQ ID NO 125
<211> LENGTH: 24
<212> TYPE: PRT
<213> ORGANISM: Homo sapiens

<400> SEQUENCE: 125

Thr Gln Gln Gly Lys Arg Ile Tyr Gly Val Val Ser Phe Gly Asp Tyr
1               5                   10                  15

Tyr Tyr Tyr Tyr Tyr Met Asp Val
                20

<210> SEQ ID NO 126
<211> LENGTH: 11
<212> TYPE: PRT
<213> ORGANISM: Homo sapiens

<400> SEQUENCE: 126

Gly Gly Asn Asn Ile Gly Ser Lys Ser Val His
1               5                   10

<210> SEQ ID NO 127
<211> LENGTH: 7
<212> TYPE: PRT
<213> ORGANISM: Homo sapiens

<400> SEQUENCE: 127

Asp Asp Ser Asp Arg Pro Ser
1               5

<210> SEQ ID NO 128
<211> LENGTH: 12
<212> TYPE: PRT
<213> ORGANISM: Homo sapiens

<400> SEQUENCE: 128

```
Gln Val Trp Asp Ser Ser Asp His Pro Trp Val
1               5                  10
```

<210> SEQ ID NO 129
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Ser
            20                  25                  30

Tyr Trp Thr Trp Ile Arg Gln Ser Pro Gly Lys Gly Leu Glu Trp Ile
        35                  40                  45

Gly Tyr Ile Ser Lys Ser Glu Ser Ala Asn Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg His Gly Gln Arg Ile Tyr Gly Val Val Ser Phe Gly Glu
            100                 105                 110

Phe Phe Thr Tyr Tyr Ser Met Asp Val Trp Gly Lys Gly Thr Thr Val
        115                 120                 125

Thr Val Ser Ser
    130
```

<210> SEQ ID NO 130
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
    50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105
```

<210> SEQ ID NO 131
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 131

Asn Ser Tyr Trp Thr
1               5

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Ile Ser Lys Ser Glu Ser Ala Asn Tyr Asn Pro Ser Leu Asn Ser
1               5                   10                  15

<210> SEQ ID NO 133
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Arg His Gly Gln Arg Ile Tyr Gly Val Val Ser Phe Gly Glu Phe
1               5                   10                  15

Phe Thr Tyr Tyr Ser Met Asp Val
            20

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Arg Gln Ala Leu Gly Ser Arg Ala Val Gln
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asn Asn Gln Asp Arg Pro Ser
1               5

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136
```

His Met Trp Asp Ser Arg Ser Gly Phe Ser Trp Ser
1               5                   10

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ctggaccgtt ctcctcctcg                                              20

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 138

His His His His His His
1               5

<210> SEQ ID NO 139
<211> LENGTH: 8
<212> TYPE: PRT
<213> ORGANISM: Homo sapiens

<400> SEQUENCE: 139

Gly Ala Phe Ile Ala Asp His Tyr
1               5

<210> SEQ ID NO 140
<211> LENGTH: 7
<212> TYPE: PRT
<213> ORGANISM: Homo sapiens

<400> SEQUENCE: 140

Val His Asp Ser Gly Asp Ile
1               5

<210> SEQ ID NO 141
<211> LENGTH: 26
<212> TYPE: PRT
<213> ORGANISM: Homo sapiens

<400> SEQUENCE: 141

Ala Thr Thr Lys His Gly Arg Arg Ile Tyr Gly Val Val Ala Phe Gly
1               5                   10                  15

Glu Trp Phe Thr Tyr Phe Tyr Met Asp Val
            20                  25

<210> SEQ ID NO 142
<211> LENGTH: 8
<212> TYPE: PRT
<213> ORGANISM: Homo sapiens

<400> SEQUENCE: 142

Gly Thr Leu Val Arg Asp Asn Tyr
1               5

<210> SEQ ID NO 143

```
<211> LENGTH: 7
<212> TYPE: PRT
<213> ORGANISM: Homo sapiens

<400> SEQUENCE: 143

Val His Asp Ser Gly Asp Thr
1               5

<210> SEQ ID NO 144
<211> LENGTH: 26
<212> TYPE: PRT
<213> ORGANISM: Homo sapiens

<400> SEQUENCE: 144

Ala Thr Thr Lys His Gly Arg Arg Ile Tyr Gly Ile Val Ala Phe Asn
1               5                   10                  15

Glu Trp Phe Thr Tyr Phe Tyr Met Asp Val
            20                  25

<210> SEQ ID NO 145
<211> LENGTH: 8
<212> TYPE: PRT
<213> ORGANISM: Homo sapiens

<400> SEQUENCE: 145

Gly Ala Ser Ile Ser Asp Ser Tyr
1               5

<210> SEQ ID NO 146
<211> LENGTH: 7
<212> TYPE: PRT
<213> ORGANISM: Homo sapiens

<400> SEQUENCE: 146

Val His Lys Ser Gly Asp Thr
1               5

<210> SEQ ID NO 147
<211> LENGTH: 26
<212> TYPE: PRT
<213> ORGANISM: Homo sapiens

<400> SEQUENCE: 147

Ala Arg Thr Leu His Gly Arg Arg Ile Tyr Gly Ile Val Ala Phe Asn
1               5                   10                  15

Glu Trp Phe Thr Tyr Phe Tyr Met Asp Val
            20                  25

<210> SEQ ID NO 148
<211> LENGTH: 8
<212> TYPE: PRT
<213> ORGANISM: Homo sapiens

<400> SEQUENCE: 148

Gly Ala Ser Val Asn Asp Ala Tyr
1               5

<210> SEQ ID NO 149
<211> LENGTH: 7
<212> TYPE: PRT
<213> ORGANISM: Homo sapiens

<400> SEQUENCE: 149

Val His His Ser Gly Asp Thr
```

```
<210> SEQ ID NO 150
<211> LENGTH: 26
<212> TYPE: PRT
<213> ORGANISM: Homo sapiens

<400> SEQUENCE: 150

Ala Arg Ala Leu His Gly Lys Arg Ile Tyr Gly Ile Val Ala Leu Gly
1               5                   10                  15

Glu Leu Phe Thr Tyr Phe Tyr Met Asp Val
            20                  25

<210> SEQ ID NO 151
<211> LENGTH: 8
<212> TYPE: PRT
<213> ORGANISM: Homo sapiens

<400> SEQUENCE: 151

Gly Ala Ser Ile Asn Asp Ala Tyr
1               5

<210> SEQ ID NO 152
<211> LENGTH: 7
<212> TYPE: PRT
<213> ORGANISM: Homo sapiens

<400> SEQUENCE: 152

Val His His Ser Gly Asp Thr
1               5

<210> SEQ ID NO 153
<211> LENGTH: 26
<212> TYPE: PRT
<213> ORGANISM: Homo sapiens

<400> SEQUENCE: 153

Ala Arg Ala Leu His Gly Lys Arg Ile Tyr Gly Ile Val Ala Leu Gly
1               5                   10                  15

Glu Leu Phe Thr Tyr Phe Tyr Met Asp Val
            20                  25

<210> SEQ ID NO 154
<211> LENGTH: 8
<212> TYPE: PRT
<213> ORGANISM: Homo sapiens

<400> SEQUENCE: 154

Gly Ala Ser Ile Asn Asp Ala Tyr
1               5

<210> SEQ ID NO 155
<211> LENGTH: 7
<212> TYPE: PRT
<213> ORGANISM: Homo sapiens

<400> SEQUENCE: 155

Val His His Ser Gly Asp Thr
1               5

<210> SEQ ID NO 156
<211> LENGTH: 26
<212> TYPE: PRT
<213> ORGANISM: Homo sapiens
```

<400> SEQUENCE: 156

Ala Arg Ala Leu His Gly Lys Arg Ile Tyr Gly Ile Val Ala Leu Gly
1               5                   10                  15

Glu Leu Phe Thr Tyr Phe Tyr Met Asp Val
            20                  25

<210> SEQ ID NO 157
<211> LENGTH: 8
<212> TYPE: PRT
<213> ORGANISM: Homo sapiens

<400> SEQUENCE: 157

Asn Gly Ser Val Ser Gly Arg Phe
1               5

<210> SEQ ID NO 158
<211> LENGTH: 7
<212> TYPE: PRT
<213> ORGANISM: Homo sapiens

<400> SEQUENCE: 158

Phe Ser Asp Thr Asp Arg Ser
1               5

<210> SEQ ID NO 159
<211> LENGTH: 26
<212> TYPE: PRT
<213> ORGANISM: Homo sapiens

<400> SEQUENCE: 159

Ala Arg Ala Gln Gln Gly Lys Arg Ile Tyr Gly Ile Val Ser Phe Gly
1               5                   10                  15

Glu Phe Phe Tyr Tyr Tyr Tyr Met Asp Ala
            20                  25

<210> SEQ ID NO 160
<211> LENGTH: 8
<212> TYPE: PRT
<213> ORGANISM: Homo sapiens

<400> SEQUENCE: 160

Asn Gly Ser Val Ser Gly Arg Phe
1               5

<210> SEQ ID NO 161
<211> LENGTH: 7
<212> TYPE: PRT
<213> ORGANISM: Homo sapiens

<400> SEQUENCE: 161

Phe Ser Asp Thr Glu Lys Ser
1               5

<210> SEQ ID NO 162
<211> LENGTH: 26
<212> TYPE: PRT
<213> ORGANISM: Homo sapiens

<400> SEQUENCE: 162

Ala Arg Thr Gln Gln Gly Lys Arg Ile Tyr Gly Val Val Ser Phe Gly
1               5                   10                  15

Glu Phe Phe His Tyr Tyr Tyr Met Asp Ala

-continued

<210> SEQ ID NO 163
<211> LENGTH: 8
<212> TYPE: PRT
<213> ORGANISM: Homo sapiens

<400> SEQUENCE: 163

Gly Gly Ser Ile Ser Ser Tyr Tyr
1               5

<210> SEQ ID NO 164
<211> LENGTH: 7
<212> TYPE: PRT
<213> ORGANISM: Homo sapiens

<400> SEQUENCE: 164

Ile Tyr Tyr Ser Gly Ser Thr
1               5

<210> SEQ ID NO 165
<211> LENGTH: 26
<212> TYPE: PRT
<213> ORGANISM: Homo sapiens

<400> SEQUENCE: 165

Ala Arg Thr Gln Gln Gly Lys Arg Ile Tyr Gly Val Val Ser Phe Gly
1               5                   10                  15
Asp Tyr Tyr Tyr Tyr Tyr Met Asp Val
            20                  25

<210> SEQ ID NO 166
<211> LENGTH: 8
<212> TYPE: PRT
<213> ORGANISM: Homo sapiens

<400> SEQUENCE: 166

Gly Asp Ser Met Asn Asn Tyr Tyr
1               5

<210> SEQ ID NO 167
<211> LENGTH: 7
<212> TYPE: PRT
<213> ORGANISM: Homo sapiens

<400> SEQUENCE: 167

Ile Ser Asp Arg Glu Ser Ala
1               5

<210> SEQ ID NO 168
<211> LENGTH: 26
<212> TYPE: PRT
<213> ORGANISM: Homo sapiens

<400> SEQUENCE: 168

Ala Thr Ala Arg Arg Gly Gln Arg Ile Tyr Gly Val Val Ser Phe Gly
1               5                   10                  15
Glu Phe Phe Tyr Tyr Tyr Ser Met Asp Val
            20                  25

<210> SEQ ID NO 169
<211> LENGTH: 8
<212> TYPE: PRT
<213> ORGANISM: Homo sapiens

<400> SEQUENCE: 169

Gly Asp Ser Met Asn Asn Tyr Tyr
1               5

<210> SEQ ID NO 170
<211> LENGTH: 7
<212> TYPE: PRT
<213> ORGANISM: Homo sapiens

<400> SEQUENCE: 170

Ile Ser Asp Arg Ala Ser Ala
1               5

<210> SEQ ID NO 171
<211> LENGTH: 26
<212> TYPE: PRT
<213> ORGANISM: Homo sapiens

<400> SEQUENCE: 171

Ala Thr Ala Arg Arg Gly Gln Arg Ile Tyr Gly Val Val Ser Phe Gly
1               5                   10                  15

Glu Phe Phe Tyr Tyr Tyr Ser Met Asp Val
            20                  25

<210> SEQ ID NO 172
<211> LENGTH: 8
<212> TYPE: PRT
<213> ORGANISM: Homo sapiens

<400> SEQUENCE: 172

Gly Asp Ser Met Asn Asn Tyr Tyr
1               5

<210> SEQ ID NO 173
<211> LENGTH: 7
<212> TYPE: PRT
<213> ORGANISM: Homo sapiens

<400> SEQUENCE: 173

Ile Ser Asp Arg Glu Ser Ala
1               5

<210> SEQ ID NO 174
<211> LENGTH: 26
<212> TYPE: PRT
<213> ORGANISM: Homo sapiens

<400> SEQUENCE: 174

Ala Thr Ala Arg Arg Gly Gln Arg Ile Tyr Gly Val Val Ser Phe Gly
1               5                   10                  15

Glu Phe Phe Tyr Tyr Tyr Ser Met Asp Val
            20                  25

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Asp Ser Met Asn Asn Ser Tyr

```
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ile Ser Lys Ser Glu Ser Ala
1               5

<210> SEQ ID NO 177
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Thr Ala Arg His Gly Gln Arg Ile Tyr Gly Val Val Ser Phe Gly
1               5                   10                  15

Glu Phe Phe Thr Tyr Tyr Ser Met Asp Val
            20                  25

<210> SEQ ID NO 178
<211> LENGTH: 6
<212> TYPE: PRT
<213> ORGANISM: Homo sapiens

<400> SEQUENCE: 178

Asn Ile Gly Ser Lys Ser
1               5

<210> SEQ ID NO 179
<211> LENGTH: 3
<212> TYPE: PRT
<213> ORGANISM: Homo sapiens

<400> SEQUENCE: 179

Asp Asp Ser
1

<210> SEQ ID NO 180
<211> LENGTH: 12
<212> TYPE: PRT
<213> ORGANISM: Homo sapiens

<400> SEQUENCE: 180

Gln Val Trp Asp Ser Ser Ser Asp His Pro Trp Val
1               5                   10

<210> SEQ ID NO 181
<211> LENGTH: 6
<212> TYPE: PRT
<213> ORGANISM: Homo sapiens

<400> SEQUENCE: 181

Ser Ile Gly Ser Arg Ala
1               5

<210> SEQ ID NO 182
```

```
<211> LENGTH: 3
<212> TYPE: PRT
<213> ORGANISM: Homo sapiens

<400> SEQUENCE: 182

Asn Asn Gln
1

<210> SEQ ID NO 183
<211> LENGTH: 12
<212> TYPE: PRT
<213> ORGANISM: Homo sapiens

<400> SEQUENCE: 183

His Ile Tyr Asp Ala Arg Arg Pro Thr Asn Trp Val
1               5                   10

<210> SEQ ID NO 184
<211> LENGTH: 6
<212> TYPE: PRT
<213> ORGANISM: Homo sapiens

<400> SEQUENCE: 184

Ser Ile Gly Ser Arg Ala
1               5

<210> SEQ ID NO 185
<211> LENGTH: 3
<212> TYPE: PRT
<213> ORGANISM: Homo sapiens

<400> SEQUENCE: 185

Asn Asn Gln
1

<210> SEQ ID NO 186
<211> LENGTH: 12
<212> TYPE: PRT
<213> ORGANISM: Homo sapiens

<400> SEQUENCE: 186

His Ile Tyr Asp Ala Arg Gly Gly Thr Asn Trp Val
1               5                   10

<210> SEQ ID NO 187
<211> LENGTH: 6
<212> TYPE: PRT
<213> ORGANISM: Homo sapiens

<400> SEQUENCE: 187

Ser Leu Gly Ser Arg Ala
1               5

<210> SEQ ID NO 188
<211> LENGTH: 3
<212> TYPE: PRT
<213> ORGANISM: Homo sapiens

<400> SEQUENCE: 188

Asn Asn Gln
1

<210> SEQ ID NO 189
<211> LENGTH: 12
<212> TYPE: PRT
```

<213> ORGANISM: Homo sapiens

<400> SEQUENCE: 189

His Ile Trp Asp Ser Arg Val Pro Thr Lys Trp Val
1               5                   10

<210> SEQ ID NO 190
<211> LENGTH: 6
<212> TYPE: PRT
<213> ORGANISM: Homo sapiens

<400> SEQUENCE: 190

Ser Leu Gly Ser Arg Ser
1               5

<210> SEQ ID NO 191
<211> LENGTH: 3
<212> TYPE: PRT
<213> ORGANISM: Homo sapiens

<400> SEQUENCE: 191

Asn Asn His
1

<210> SEQ ID NO 192
<211> LENGTH: 12
<212> TYPE: PRT
<213> ORGANISM: Homo sapiens

<400> SEQUENCE: 192

His Ile Trp Asp Ser Arg Arg Pro Thr Asn Trp Val
1               5                   10

<210> SEQ ID NO 193
<211> LENGTH: 6
<212> TYPE: PRT
<213> ORGANISM: Homo sapiens

<400> SEQUENCE: 193

Ser Leu Gly Ser Arg Ser
1               5

<210> SEQ ID NO 194
<211> LENGTH: 3
<212> TYPE: PRT
<213> ORGANISM: Homo sapiens

<400> SEQUENCE: 194

Asn Asn Asn
1

<210> SEQ ID NO 195
<211> LENGTH: 12
<212> TYPE: PRT
<213> ORGANISM: Homo sapiens

<400> SEQUENCE: 195

His Ile Trp Asp Ser Arg Arg Pro Thr Asn Trp Val
1               5                   10

<210> SEQ ID NO 196
<211> LENGTH: 6
<212> TYPE: PRT
<213> ORGANISM: Homo sapiens

```
<400> SEQUENCE: 196

Ser Leu Gly Ser Arg Ser
1               5

<210> SEQ ID NO 197
<211> LENGTH: 3
<212> TYPE: PRT
<213> ORGANISM: Homo sapiens

<400> SEQUENCE: 197

Asn Asn Asn
1

<210> SEQ ID NO 198
<211> LENGTH: 12
<212> TYPE: PRT
<213> ORGANISM: Homo sapiens

<400> SEQUENCE: 198

His Ile Trp Asp Ser Arg Arg Pro Thr Asn Trp Val
1               5                   10

<210> SEQ ID NO 199
<211> LENGTH: 6
<212> TYPE: PRT
<213> ORGANISM: Homo sapiens

<400> SEQUENCE: 199

Ala Leu Gly Ser Arg Ala
1               5

<210> SEQ ID NO 200
<211> LENGTH: 3
<212> TYPE: PRT
<213> ORGANISM: Homo sapiens

<400> SEQUENCE: 200

Asn Asn Gln
1

<210> SEQ ID NO 201
<211> LENGTH: 12
<212> TYPE: PRT
<213> ORGANISM: Homo sapiens

<400> SEQUENCE: 201

His Met Trp Asp Ser Arg Ser Gly Phe Ser Trp Ser
1               5                   10

<210> SEQ ID NO 202
<211> LENGTH: 6
<212> TYPE: PRT
<213> ORGANISM: Homo sapiens

<400> SEQUENCE: 202

Ala Leu Gly Ser Arg Ala
1               5

<210> SEQ ID NO 203
<211> LENGTH: 3
<212> TYPE: PRT
<213> ORGANISM: Homo sapiens

<400> SEQUENCE: 203
```

Asn Asn Gln
1

<210> SEQ ID NO 204
<211> LENGTH: 12
<212> TYPE: PRT
<213> ORGANISM: Homo sapiens

<400> SEQUENCE: 204

His Met Trp Asp Ser Arg Ser Gly Phe Ser Trp Ser
1               5                   10

<210> SEQ ID NO 205
<211> LENGTH: 6
<212> TYPE: PRT
<213> ORGANISM: Homo sapiens

<400> SEQUENCE: 205

Ala Leu Gly Ser Arg Ala
1               5

<210> SEQ ID NO 206
<211> LENGTH: 3
<212> TYPE: PRT
<213> ORGANISM: Homo sapiens

<400> SEQUENCE: 206

Asn Asn Gln
1

<210> SEQ ID NO 207
<211> LENGTH: 12
<212> TYPE: PRT
<213> ORGANISM: Homo sapiens

<400> SEQUENCE: 207

His Met Trp Asp Ser Arg Ser Gly Phe Ser Trp Ser
1               5                   10

<210> SEQ ID NO 208
<211> LENGTH: 6
<212> TYPE: PRT
<213> ORGANISM: Homo sapiens

<400> SEQUENCE: 208

Ser Phe Ala Ser Arg Ala
1               5

<210> SEQ ID NO 209
<211> LENGTH: 3
<212> TYPE: PRT
<213> ORGANISM: Homo sapiens

<400> SEQUENCE: 209

Asn Asn Gln
1

<210> SEQ ID NO 210
<211> LENGTH: 12
<212> TYPE: PRT
<213> ORGANISM: Homo sapiens

<400> SEQUENCE: 210

His Lys Trp Asp Ser Arg Ser Pro Leu Ser Trp Val
1               5                   10

<210> SEQ ID NO 211
<211> LENGTH: 6
<212> TYPE: PRT
<213> ORGANISM: Homo sapiens

<400> SEQUENCE: 211

Ser Arg Gly Ser Arg Ala
1               5

<210> SEQ ID NO 212
<211> LENGTH: 3
<212> TYPE: PRT
<213> ORGANISM: Homo sapiens

<400> SEQUENCE: 212

Asn Asn Gln
1

<210> SEQ ID NO 213
<211> LENGTH: 12
<212> TYPE: PRT
<213> ORGANISM: Homo sapiens

<400> SEQUENCE: 213

His Tyr Trp Asp Ser Arg Ser Pro Ile Ser Trp Val
1               5                   10

<210> SEQ ID NO 214
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214 agagcattttt atacaacagg agacataata ggagatataa gacaagcaca ttgcaacatt    60
agtaaagtaa aatggc                                                    76

<210> SEQ ID NO 215
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tcctggtcct atatgtatac ttttccttgt attgttgttg ggtcttgtac aattaatttc    60
tacagtttca ttc                                                       73

<210> SEQ ID NO 216
<211> LENGTH: 20
<212> TYPE: PRT
<213> ORGANISM: Human immunodeficiency virus

<400> SEQUENCE: 216

Asn Cys Thr Arg Pro Asn Asn Asn Thr Arg Lys Ser Ile Asn Ile Gly
1               5                   10                  15

Pro Gly Arg Ala
            20

<210> SEQ ID NO 217
<211> LENGTH: 19
<212> TYPE: PRT
<213> ORGANISM: Human immunodeficiency virus -continued

<400> SEQUENCE: 217

Asn Asn Asn Thr Arg Lys Ser Ile Asn Ile Gly Pro Gly Arg Ala Leu
1               5                   10                  15

Tyr Thr Thr

<210> SEQ ID NO 218
<211> LENGTH: 19
<212> TYPE: PRT
<213> ORGANISM: Human immunodeficiency virus

<400> SEQUENCE: 218

Arg Lys Ser Ile Asn Ile Gly Pro Gly Arg Ala Leu Tyr Thr Thr Gly
1               5                   10                  15

Glu Ile Ile

<210> SEQ ID NO 219
<211> LENGTH: 20
<212> TYPE: PRT
<213> ORGANISM: Human immunodeficiency virus

<400> SEQUENCE: 219

Asn Ile Gly Pro Gly Arg Ala Leu Tyr Thr Thr Gly Glu Ile Ile Gly
1               5                   10                  15

Asp Ile Arg Gln
            20

<210> SEQ ID NO 220
<211> LENGTH: 20
<212> TYPE: PRT
<213> ORGANISM: Human immunodeficiency virus

<400> SEQUENCE: 220

Arg Ala Leu Tyr Thr Thr Gly Glu Ile Ile Gly Asp Ile Arg Gln Ala
1               5                   10                  15

His Cys Asn Leu
            20

<210> SEQ ID NO 221
<211> LENGTH: 20
<212> TYPE: PRT
<213> ORGANISM: Human immunodeficiency virus

<400> SEQUENCE: 221

Thr Gly Glu Ile Ile Gly Asp Ile Arg Gln Ala His Cys Asn Leu Ser
1               5                   10                  15

Lys Thr Gln Trp
            20

<210> SEQ ID NO 222
<211> LENGTH: 20
<212> TYPE: PRT
<213> ORGANISM: Human immunodeficiency virus

```
<400> SEQUENCE: 222

Gly Asp Ile Arg Gln Ala His Cys Asn Leu Ser Lys Thr Gln Trp Glu
1               5                   10                  15

Asn Thr Leu Glu
            20

<210> SEQ ID NO 223
<211> LENGTH: 20
<212> TYPE: PRT
<213> ORGANISM: Human immunodeficiency virus

<400> SEQUENCE: 223

Ala His Cys Asn Leu Ser Lys Thr Gln Trp Glu Asn Thr Leu Glu Gln
1               5                   10                  15

Ile Ala Ile Lys
            20
```

BROADLY NEUTRALIZING ANTIBODY DIRECTED AGAINST HIV-1 GP140

CROSS-REFERENCE TO RELATED APPLICATIONS

This application is a Divisional of U.S. patent application Ser. No. 14/436,608, filed Apr. 17, 2015, which is the U.S. National Phase of International application Ser. No. PCT/US2013/065696, filed Oct. 18, 2013, which claims priority under 35 U.S.C. § 119(e) to U.S. Provisional Application No. 61/715,642 filed on Oct. 18, 2012, which are hereby incorporated by reference in their entireties.

GOVERNMENT INTERESTS

The invention disclosed herein was made, at least in part, with government support under Grant No. P01 AI081677 from the National Institutes of Health. Accordingly, the U.S. Government has certain rights in this invention.

FIELD OF THE INVENTION

This invention relates to broad and potent antibodies against Human Immunodeficiency Virus ("HIV").

BACKGROUND OF THE INVENTION

HIV causes acquired immunodeficiency syndrome (AIDS), a condition in humans characterized by clinical features including wasting syndromes, central nervous system degeneration and profound immunosuppression that results in life-threatening opportunistic infections and malignancies. Since its discovery in 1981, HIV type 1 (HIV-1) has led to the death of at least 25 million people worldwide. It is predicted that 20-60 million people will become infected over the next two decades even if there is a 2.5% annual decrease in HIV infections. There is a need for therapeutic agents and methods for treatment or inhibition of HIV infection.

Some HIV infected individuals show broadly neutralizing IgG antibodies in their serum. Yet, little is known regarding the specificity and activity of these antibodies, despite their potential importance in designing effective vaccines. In animal models, passive transfer of neutralizing antibodies can contribute to protection against virus challenge. Neutralizing antibody responses also can be developed in HIV-infected individuals but the detailed composition of the serologic response is yet to be fully uncovered.

SUMMARY OF INVENTION

This invention relates to new categories of broadly-neutralizing anti-HIV antibodies. The consensus heavy and light chain amino acid sequences of the antibodies are listed below and shown in FIGS. 3a and 3b:

```
                                                (SEQ ID NO: 1)
QVQLQESGPGLVKPSETLSLICSVSGX₁SX₂X₃DX₄YWSWIRQSPGKGLE
WIGYVHDSGDTNYNPSLKSRVX₅X₆SLDTSKNQVSLKLX₇X₈VTAADSA
X₉YYCARAX₁₀HGX₁₁RIYGIVAFGEX₁₂FTYFYMDVWGKGTIVIVSS (SEQ ID NO: 2)
SX₁VIRPQPPSLSVAPGETARIX₂CGEX₃SLGSRAVQWYQQRPGQAPSLI
IYNNQDRPSGIPERFSGSPDX₄X₅FGTTATLTITX₆VEAGDEADYYCHIW
DSRX₇PTX₈WVFGGGITLTVL
```

In the sequence of SEQ ID NO: 1 or 2, each "X" can be any amino acid residue or no amino acid. Preferably, each of the Xs can be a residue at the corresponding location of clonal variants 10-259, 10-303, 10-410, 10-847, 10-996, 10-1074, 10-1121, 10-1130, 10-1146, 10-1341, and 10-1369 as shown in FIGS. 3a and 3b, and an artificially modified version of 10-1074 antibody, 10-1074GM.

Accordingly, one aspect of this invention features an isolated anti-HIV antibody, or antigen binding portion thereof, having at least one complementarity determining region (CDR) having a sequence selected from the group consisting of SEQ ID NOs: 33-38, with a proviso that the antibody is not antibody PGT-121, 122, or 123. SEQ ID NOs: 33-38 refer to the sequences of heavy chain CDRs (CDRH) 1-3 and the light chain CDRs (CDRL) 1-3 under the Kabat system as shown in FIGS. 3a and 3b. In one embodiment, the CDR can contain a sequence selected from the group consisting of SEQ ID NOs: 39-104, i.e., the CDR sequences under the KABAT system as shown in Table 1 below. Alternatively, the CDR can contain a sequence selected from those corresponding antibodies' CDR sequences under the IMGT system as shown in Table 1 below.

In one embodiment, the isolated anti-HIV antibody, or antigen binding portion thereof, contains a heavy chain variable region that includes CDRH 1, CDRH 2, and CDRH 3, wherein the CDRH 1, CDRH 2 and CDRH 3 include the respective sequences of SEQ ID NOs: 33-35. The CDRH 1, CDRH 2 and CDRH 3 can also include the respective sequences of a CDRH set selected from the group consisting of SEQ ID NOs: 39-41, SEQ ID NOs: 45-47, SEQ ID NOs: 51-53, SEQ ID NOs: 57-59, SEQ ID NOs: 63-65, SEQ ID NOs: 69-71, SEQ ID NOs: 75-77, SEQ ID NOs: 81-83, SEQ ID NOs: 87-89, SEQ ID NOs: 93-95, SEQ ID NOs: 99-101, and SEQ ID NOs: 131-133. Alternatively, the CDRHs can contain the respective sequences selected from those corresponding antibodies' CDR sequences under the IMGT system as shown in Table 1 below.

In another embodiment, the isolated anti-HIV antibody, or antigen binding portion thereof, contains a light chain variable region that includes CDRL 1, CDRL 2 and CDRL 3, wherein the CDRL 1, CDRL 2 and CDRL 3 include the respective sequences of SEQ ID NOs: 36-38. For example, the CDRL 1, CDRL 2 and CDRL 3 can include the respective sequences of a CDRL set selected from the group consisting of SEQ ID NOs: 42-44, SEQ ID NOs: 48-50, SEQ ID NOs: 54-56, SEQ ID NOs: 60-62, SEQ ID NOs: 66-68, SEQ ID NOs: 72-74, SEQ ID NOs: 78-80, SEQ ID NOs: 84-86, SEQ ID NOs: 90-92, SEQ ID NOs: 96-98, SEQ ID NOs: 102-104, and SEQ ID NOs: 134-136. Alternatively, the CDRLs can contain the respective sequences selected from those corresponding antibodies' CDR sequences under the IMGT system as shown in Table 1 below.

In yet another embodiment, the above-mentioned isolated anti-HIV antibody, or antigen binding portion thereof, includes (i) a heavy chain variable region that include CDRH 1, CDRH 2, and CDRH 3, and (ii) a light chain variable region that include CDRL 1, CDRL 2 and CDRL 3. The CDRH 1, CDRH 2, CDRH 3, CDRL 1, CDRL 2 and CDRL 3 can include the respective sequences of a CDR set selected from the group consisting of SEQ ID NOs: 39-44, SEQ ID NOs: 45-50, SEQ ID NOs: 51-56, SEQ ID NOs: 57-62, SEQ ID NOs: 63-68, SEQ ID NOs: 69-74, SEQ ID NOs: 75-79, SEQ ID NOs: 81-86, SEQ ID NOs: 87-92, SEQ ID NOs: 93-98, SEQ ID NOs: 99-104, and SEQ ID NOs: 131-136. Alternatively, the CDRHs and CDRLs can contain the respective sequences selected from those corresponding antibodies' CDR sequences under the IMGT system as shown in Table 1 below.

In a further embodiment, the isolated anti-HIV antibody, or antigen binding portion thereof, contains one or both of (i) a heavy chain having the consensus amino acid sequence of SEQ ID NO: 1 and (ii) a light chain having the consensus amino acid sequence of SEQ ID NO: 2. The heavy chain can contain a sequence selected from the group consisting of SEQ ID NOs: 3, 5, 7, 9, 11, 13, 15, 17, 19, 21, 23, and 129, and the light chain can contain a sequence selected from the group consisting of SEQ ID NOs: 4, 6, 8, 10, 12, 14, 16, 18, 20, 22, 24, and 130. For example, the heavy chain and the light chain can include the respective sequences of SEQ ID NOs: 3-4, SEQ ID NOs: 5-6, SEQ ID NOs: 7-8, SEQ ID NOs: 9-10, SEQ ID NOs: 11-12, SEQ ID NOs: 13-14, SEQ ID NOs: 15-16, SEQ ID NOs: 17-18, SEQ ID NOs: 19-20, SEQ ID NOs: 21-22, SEQ ID NOs: 23-24, and 129-130.

In a preferred embodiment, the isolated anti-HIV antibody is one selected from the group consisting of 10-259, 10-303, 10-410, 10-847, 10-996, 10-1074, 10-1074GM, 10-1121, 10-1130, 10-1146, 10-1341, and 10-1369. Their corresponding heavy chain variable regions, light chain variable regions, CDRH 1-3 and CDRL 1-3 are shown in FIGS. 3a and 3b. In a more preferred embodiment, the isolated anti-HIV antibody is a 10-1074-like antibody, i.e., one reselected from the group consisting of 10-847, 10-996, 10-1074, 10-1074GM, 10-1146, and 10-1341. An antibody of this group is more potent in neutralizing contemporary viruses than PGT121. The above-discussed antibody can be a human antibody, a humanized antibody, or a chimeric antibody. encoding a CDR, a heavy chain variable region, or a light chain variable region of the above-discussed anti-HIV antibody, or antigen binding portion thereof. Also featured are a vector having the nucleic acid and a cultured cell having the vector.

The nucleic acid, vector, and cultured cell can be used in a method for making an anti-HIV antibody or a fragment thereof. The method includes, among others, the steps of: obtaining the cultured cell mentioned above; culturing the cell in a medium under conditions permitting expression of a polypeptide encoded by the vector and assembling of an antibody or fragment thereof, and purifying the antibody or fragment from the cultured cell or the medium of the cell.

In a third aspect, the invention features a pharmaceutical composition containing (i) at least one anti-HIV antibody mentioned above, or antigen binding portion thereof, and (ii) a pharmaceutically acceptable carrier.

In a fourth aspect, the invention provides a method of preventing or treating an HIV infection or an HIV-related disease. The method includes, among others, the steps of: identifying a patient in need of such prevention or treatment, and administering to said patient a first therapeutic agent containing a therapeutically effective amount of at least one anti-HIV antibody mentioned above, or antigen binding portion thereof. The method can further include administering a second therapeutic agent, such as an antiviral agent.

In a fifth aspect, the invention provides a kit having a pharmaceutically acceptable dose unit of a pharmaceutically effective amount of at least one isolated anti-HIV antibody mentioned a above, or antigen binding portion thereof, and a pharmaceutically acceptable dose unit of a pharmaceutically effective amount of an anti-HIV agent. The two pharmaceutically acceptable dose units can optionally take the form of a single pharmaceutically acceptable dose unit. Exemplary anti-HIV agent can be one selected from the group consisting of a non-nucleoside reverse transcriptase inhibitor, a protease inhibitor, a entry or fusion inhibitor, and an integrase inhibitor.

In a sixth aspect, the invention provides a kit for the diagnosis, prognosis or monitoring the treatment of an HIV infection in a subject. The kit contains one or more detection reagents which specifically bind to anti-HIV neutralizing antibodies in a biological sample from a subject. The kit can further include reagents for performing PCR or mass spectrometry.

The details of one or more embodiments of the invention are set forth in the description below. Other features, objects, and advantages of the invention will be apparent from the description and from the claims.

BRIEF DESCRIPTION OF THE DRAWINGS

FIG. 3A discloses SEQ ID NOS 31, 9, 21, 13, 19, 11, 23, 27, 3, 29, 17, 15, 7, 25, 5, and 1, respectively, in order of appearance. FIG. 3B discloses SEQ ID NOS 32, 26, 6, 24, 30, 4, 10, 14, 22, 12, 20, 8, 28, 18, 16, and 2, respectively, in order of appearance.

FIGS. 4A, 4B and 4C show: Binding affinity of PGT121 and 10-1074 clonal variants. (A) Binding affinity of the interaction of PGT121 IgG antibody variants with YU-2 gp140 and gp120 ligands as measured by surface plasmon resonance (SPR). M, mol/l; s, seconds; RU, response units; /, no binding detected. A chi$^2$ value ($\chi^2$) <10 indicates that the 1:1 binding model used to fit the curves adequately described the experimental data. Equilibrium and kinetic constants shown are considered as "apparent" constants to account for avidity effects resulting from bivalent binding of IgGs. (B) Dot plots showing the association ($k_a$) and dissociation ($k_d$) rate constants for PGT121-like (blue shading) and 10-1074-like (green shading). (C) Linear regression graphs comparing the $k_a$ and $k_d$ values of the IgG antibodies for their binding to gp120 and gp140 (x axis) vs their neutralization potencies (mean $IC_{80}$ values) against the 9 viruses shown in Table 4 (y axis).

FIG. 5C discloses SEQ ID NOS 216-223, respectively, in order of appearance.

(FIG. 7A) Monosaccharide sequences of the set of 15 N-glycan probes used in the glycan microarray analyses to examine PGT121-like and 10-1074-like antibodies for direct binding to N-glycans. DH, designates the lipid tag 1,2-dihexadecyl-sn-glycero-3-phosphoethanolamine (DHPE) to which the N-glycans were conjugated by reductive amination. Key features of note are (i) PGT121-group antibodies bound the monoantennary N-glycan probe 10 (N2) with a galactose-terminating antenna joined by 1-3-linkage to the core mannose, but not the isomeric N-glycan probe 11 (designated N4) with the antenna 1-6-linked to the core mannose; (ii) the presence of this galactose-terminating 1-6-linked antenna, as in the biantennary probe 13 (NA2), was permissive to binding, as was the presence of α2-6-linked (but not α2-3-linked) sialic acid; (iii) the biantennary probe 12 (NGA2), lacking galactose and terminating in N-acetylglucosamine, was not bound. (FIG. 7B) Bar graphs comparing glycan binding by PGT121-like, 10-1074-like, and the germline version (GL) antibodies. 10-188, an anti-V3 loop antibody, was used as negative control. Numerical scores of binding are measured as fluorescence intensity (means at duplicate spots) for probes arrayed at 2 fmol (white) and 5 fmol per spot (grey).

FIGS. 11A and 11B depict: Neutralization of two R5 tropic SHIVs with a panel of 11 broadly acting anti-HIV-1 mAbs. The calculated IC50 values for neutralizing SHIVAD8EO (A) and SHIVDH12-V3AD8 (B).

FIGS. 13A, 13B and 13C depict: Plasma concentration of bNAbs. The concentration of mAbs was determined by measuring neutralization activity in plasma samples. (A) ID50-values measured in TZM.b1 neutralization assay of 10-1074 and 3BNC117 against HIV-1 strains that are sensitive to one but not the other bNAb (i.e. HIV-1 strain X2088_9 (10-1074 sensitive); HIV-1 strain Q769_d22 (3BNC117 sensitive). (B) Neutralizing activity of plasma before antibody administration (preP), but spiked with 0.01, 0.1, 1, 10, and 100 µg/ml of antibodies 10-1074 (blue) or 3BNC117 (green). Neutralizing activity reported as plasma $_{ID50}$ titers (left columns) and converted to antibody concentrations (right columns) based on measured ID50-values in (A). (C) $_{ID50}$ titers (left columns) and concentrations of bNAbs (right columns) measured in the indicated macaque plasma samples before (Prebleed) and following (Day) bNAb administration.

FIG. 14 depicts Table 7 showing neutralization sensitivity according to N332 PNGS. Dots indicate the presence of an asparagine and of a serine residue in position 332 and 334, respectively. Mutations at positions 332 and 334 (HXB2 sequence number) are indicated by the substituting amino acid. IC50 values indicate neutralization sensitivity in the TZM-b1 assay.

DETAILED DESCRIPTION OF THE INVENTION

Figures 1A, 1B:
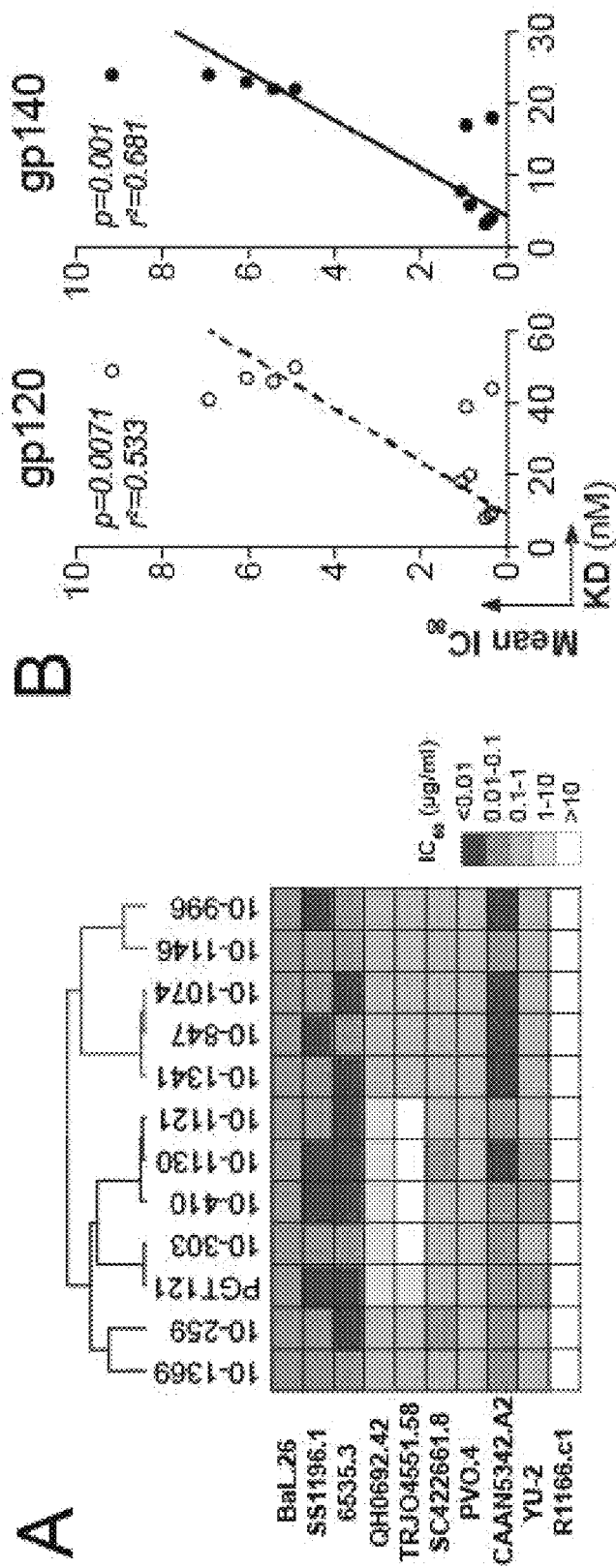
FIGS. 1A, 1B, 1C, 1D and 1E show: Neutralization activity of PGT121-like and 10-1074-like variants. (A) Heat map comparing the neutralization potencies of PGT121-like and 10-1074-like antibodies in the TZM-b1 assay. Darker colors=more potent neutralization; white=no neutralization. (B) Correlation between the mean $IC_{80}$ against 9 viruses (y axis) and apparent $K_D$ values for binding to gp120 and gp140 (x axis). (C) Graph comparing the neutralization breadth and potencies of PGT121, 10-996 and 10-1074 antibodies in the TZM-b1 assay against an extended panel of 119 viruses. The y axis shows the cumulative frequency of $IC_{50}$ so values up to the concentration shown on the x axis. The spider graph (upper left corner) shows the frequency distribution of neutralized viruses according to HIV-1 clades. (D) Dot plot showing molar neutralization ratios (MNRs; ratio of the Fab and IgG $IC_{50}$ concentrations). Horizontal bars represent the mean $ICs_{50}$s for all viruses. (E) Bar graph comparing the neutralization potencies of PGT121 (dark gray) and 10-1074 (light gray) against viruses isolated from historical (Hist.) and contemporary (Cont.) seroconverters. ns, non significant; **, p<0.005. Fold difference between median IC50s for the neutralization of contemporary viruses by PGT121 and 10-1074 is indicated.

This invention is based, at least in part, on an unexpected discovery of a new category of broadly neutralizing antibodies (bNAbs) against HIV that can recognize carbohydrate-dependent epitopes, including complex-type N-glycan, on gp120.

Antibodies are essential for the success of most vaccines, and antibodies against HIV appear to be the only correlate of protection in the recent RV144 anti-HIV vaccine trial. Some HIV-1 infected patients develop broadly neutralizing serologic activity against the gp160 viral spike 2-4 years after infection, but these antibodies do not generally protect infected humans because autologous viruses escape through mutation. Nevertheless, broadly neutralizing activity puts selective pressure on the virus and passive transfer of broadly neutralizing antibodies (bNAbs) to macaques protects against SHIV infection. It has therefore been proposed that vaccines that elicit such antibodies may be protective against HIV infection in humans.

The development of single cell antibody cloning techniques revealed that bNAbs target several different epitopes on the HIV-1 gp160 spike. The most potent HIV-1 bNAbs recognize the CD4 binding site (CD4bs) (Science 333 (6049):1633-1637; Nature 477(7365):466-470; Science 334 (6060):1289-1293) and carbohydrate-dependent epitopes associated with the variable loops (Nature 477(7365):466-470; Science 326(5950):285-289; Science 334(6059):1097-1103; Nature 480(7377):336-343), including the V1/V2 (PG9/PG16) (Science 326(5950):285-289) and V3 loops (PGTs) (Nature 477(7365):466-470). Less is known about carbohydrate-dependent epitopes because the antibodies studied to date are either unique examples or members of small clonal families.

To better understand the neutralizing antibody response to HIV-1 and the epitope targeted by PGT antibodies, we isolated members of a large clonal family dominating the gp160-specific IgG memory response from the clade A-infected patient who produced PGT121. As disclosed herein, PGT121 antibodies segregate into two groups, a PGT121-like and a 10-1074-like group, according to sequence, binding affinity, neutralizing activity and recognition of carbohydrates and the V3 loop. 10-1074 and related family members exhibit unusual potent neutralization, including broad reactivity against newly-transmitted viruses. Unlike previously-characterized carbohydrate-dependent bNAbs, PGT121 binds to complex-type, rather than high-mannose, N-glycans in glycan microarray experiments. Crystal structures of PGT121 and 10-1074 compared with structures of their germline precursor and a structure of PGT121 bound to a complex-type N-glycan rationalize their distinct properties.

In one example, assays were carried out to isolate B-cell clones encoding PGT121, which is unique among glycan-dependent bNAbs in recognizing complex-type, rather than high-mannose, N-glycans. The PGT121 clones segregates into PGT121- and 10-1074-like groups distinguished by sequence, binding affinity, carbohydrate recognition and neutralizing activity. The 10-1074 group exhibit remarkable potency and breadth despite not binding detectably to protein-free glycans. Crystal structures of un-liganded PGT121, 10-1074, and their germline precursor reveal that differential carbohydrate recognition maps to a cleft between CDRH2 and CDRH3, which was occupied by a complex-type N-glycan in a separate PGT121 structure. Swapping glycan contact residues between PGT121 and 10-1074 confirmed the importance of these residues in neutralizing activities. HIV envelopes exhibit varying proportions of high- mannose- and complex-type N-glycans, thus these results, including the first structural characterization of complex-type N-glycan recognition by anti-HIV bNAbs, are critical for understanding how antibodies and ultimately vaccines might achieve broad neutralizing activity.

The term "antibody" (Ab) as used herein includes monoclonal antibodies, polyclonal antibodies, multispecific antibodies (for example, bispecific antibodies and polyreactive antibodies), and antibody fragments. Thus, the term "antibody" as used in any context within this specification is meant to include, but not be limited to, any specific binding member, immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv, and scFv (single chain or related entity). It is understood in the art that an antibody is a glycoprotein having at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors.

Also included in the definition of "antibody" as used herein are chimeric antibodies, humanized antibodies, and recombinant antibodies, human antibodies generated from a transgenic non-human animal, as well as antibodies selected from libraries using enrichment technologies available to the artisan.

The term "variable" refers to the fact that certain segments of the variable (V) domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta sheet configuration, connected by three hypervariable regions, which form loops connecting, and in some cases forming part of, the beta sheet structure. The hypervariable regions in each chain are held together in close proximity by the FRs and, with the hypervariable regions from the other chain, contribute to the formation of the antigen-binding site of antibodies (see, for example, Kabat et al., Sequences of Proteins of Immunological Interest, 5th Ed. Public Health Service, National Institutes of Health, Bethesda, Md. (1991)).

The term "hypervariable region" as used herein refers to the amino acid residues of an antibody that are responsible for antigen binding. The hypervariable region generally comprises amino acid residues from a "complementarity determining region" ("CDR").

The term "monoclonal antibody" as used herein refers to an antibody obtained from a population of substantially homogeneous antibodies, i.e., the individual antibodies comprising the population are identical except for possible naturally occurring mutations that may be present in minor amounts. The term "polyclonal antibody" refers to preparations that include different antibodies directed against different determinants ("epitopes").

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with, or homologous to, corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., Proc. Natl. Acad. Sci. USA, 81:6851-6855 (1984)). The described invention provides variable region antigen-binding sequences derived from human antibodies. Accordingly, chimeric antibodies of primary interest herein include antibodies having one or more human antigen binding sequences (for example, CDRs) and containing one or more sequences derived from a non-human antibody, for example, an FR or C region sequence. In addition, chimeric antibodies included herein are those comprising a human variable region antigen binding sequence of one antibody class or subclass and another sequence, for example, FR or C region sequence, derived from another antibody class or subclass.

A "humanized antibody" generally is considered to be a human antibody that has one or more amino acid residues introduced into it from a source that is non-human. These non-human amino acid residues often are referred to as "import" residues, which typically are taken from an "import" variable region. Humanization may be performed following the method of Winter and co-workers (see, for example, Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (see, for example, U.S. Pat. No. 4,816,567), where substantially less than an intact human variable region has been substituted by the corresponding sequence from a non-human species.

An "antibody fragment" comprises a portion of an intact antibody, such as the antigen binding or variable region of the intact antibody. Examples of antibody fragments include, but are not limited to, Fab, Fab', F(ab')2, and Fv fragments; diabodies; linear antibodies (see, for example, U.S. Pat. No. 5,641,870; Zapata et al., Protein Eng. 8(10): 1057-1062 [1995]); single-chain antibody molecules; and multispecific antibodies formed from antibody fragments.

"Fv" is the minimum antibody fragment that contains a complete antigen-recognition and antigen-binding site. This fragment contains a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable region (or half of an Fv comprising only three CDRs specific for an antigen) has the ability to recognize and bind antigen, although at a lower affinity than the entire binding site.

"Single-chain Fv" ("sFv" or "scFv") are antibody fragments that comprise the VH and VL antibody domains connected into a single polypeptide chain. The sFv polypeptide can further comprise a polypeptide linker between the VH and VL domains that enables the sFv to form the desired structure for antigen binding. For a review of sFv, see, for example, Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from about 11 kDa to about 15 kDa. DAbs are the robust variable regions of the heavy and light chains of immunoglobulins (VH and VL, respectively). They are highly expressed in microbial cell culture, show favorable biophysical properties including, for example, but not limited to, solubility and temperature stability, and are well suited to selection and affinity maturation by in vitro selection systems such as, for example, phage display. DAbs are bioactive as monomers and, owing to their small size and inherent stability, can be formatted into larger molecules to create drugs with prolonged serum half-lives or other pharmacological activities. Examples of this technology have been described in, for example, WO9425591 for antibodies derived from Camelidae heavy chain Ig, as well in US20030130496 describing the isolation of single domain fully human antibodies from phage libraries.

Fv and sFv are the only species with intact combining sites that are devoid of constant regions. Thus, they are suitable for reduced nonspecific binding during in vivo use. sFv fusion proteins can be constructed to yield fusion of an effector protein at either the amino or the carboxy terminus of an sFv. See, for example, Antibody Engineering, ed. Borrebaeck, supra. The antibody fragment also can be a "linear antibody", for example, as described in U.S. Pat. No. 5,641,870 for example. Such linear antibody fragments can be monospecific or bispecific.

In certain embodiments, antibodies of the described invention are bispecific or multi-specific. Bispecific antibodies are antibodies that have binding specificities for at least two different epitopes. Exemplary bispecific antibodies can bind to two different epitopes of a single antigen. Other such antibodies can combine a first antigen binding site with a binding site for a second antigen. Alternatively, an anti-HIV arm can be combined with an arm that binds to a triggering molecule on a leukocyte, such as a T-cell receptor molecule (for example, CD3), or Fc receptors for IgG (Fc gamma R), such as Fc gamma RI (CD64), Fc gamma RII (CD32) and Fc gamma RIII (CD16), so as to focus and localize cellular defense mechanisms to the infected cell. Bispecific antibodies also can be used to localize cytotoxic agents to infected cells. Bispecific antibodies can be prepared as full length antibodies or antibody fragments (for example, F(ab')2 bispecific antibodies). For example, WO 96/16673 describes a bispecific anti-ErbB2/anti-Fc gamma RIII antibody and U.S. Pat. No. 5,837,234 discloses a bispecific anti-ErbB2/anti-Fc gamma RI antibody. For example, a bispecific anti-ErbB2/Fc alpha antibody is reported in WO98/02463; U.S. Pat. No. 5,821,337 teaches a bispecific anti-ErbB2/anti-CD3 antibody. See also, for example, Mouquet et al., Polyreactivity Increases The Apparent Affinity Of Anti-HIV Antibodies By Heteroligation. Nature. 467, 591-5 (2010), and Mouquet et al., Enhanced HIV-1 neutralization by antibody heteroligation" Proc Natl Acad Sci USA. 2012 Jan.17; 109(3):875-80.

Methods for making bispecific antibodies are known in the art. Traditional production of full length bispecific antibodies is based on the co-expression of two immunoglobulin heavy chain-light chain pairs, where the two chains have different specificities (see, for example, Millstein et al., Nature, 305:537-539 (1983)). Similar procedures are disclosed in, for example, WO 93/08829, Traunecker et al., EMBO J., 10:3655-3659 (1991) and see also Mouquet et al., Enhanced HIV-1 neutralization by antibody heteroligation" Proc Natl Acad Sci USA. 2012 Jan. 17; 109(3):875-80.

Alternatively, antibody variable regions with the desired binding specificities (antibody-antigen combining sites) are fused to immunoglobulin constant domain sequences. The fusion is with an Ig heavy chain constant domain, comprising at least part of the hinge, CH2, and CH3 regions. According to some embodiments, the first heavy-chain constant region (CH1) containing the site necessary for light chain bonding, is present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Techniques for generating bispecific antibodies from antibody fragments also have been described in the literature. For example, bispecific antibodies can be prepared using chemical linkage. For example, Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Other modifications of the antibody are contemplated herein. For example, the antibody can be linked to one of a variety of nonproteinaceous polymers, for example, polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in, for example, Remington's Pharmaceutical Sciences, 16th edition, Oslo, A., Ed., (1980).

Typically, the antibodies of the described invention are produced recombinantly, using vectors and methods available in the art. Human antibodies also can be generated by in vitro activated B cells (see, for example, U.S. Pat. Nos. 5,567,610 and 5,229,275). General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Human antibodies also can be produced in transgenic animals (for example, mice) that are capable of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice results in the production of human antibodies upon antigen challenge. See, for example, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals can be genetically engineered to produce human antibodies comprising a polypeptide of the described invention.

Various techniques have been developed for the production of antibody fragments. Traditionally, these fragments were derived via proteolytic digestion of intact antibodies (see, for example, Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')2 fragments (see, for example, Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner.

Other techniques that are known in the art for the selection of antibody fragments from libraries using enrichment technologies, including but not limited to phage display, ribosome display (Hanes and Pluckthun, 1997, Proc. Nat. Acad. Sci. 94: 4937-4942), bacterial display (Georgiou, et al., 1997, Nature Biotechnology 15: 29-34) and/or yeast display (Kieke, et al., 1997, Protein Engineering 10: 1303-1310) may be utilized as alternatives to previously discussed technologies to select single chain antibodies. Single-chain antibodies are selected from a library of single chain antibodies produced directly utilizing filamentous phage technology. Phage display technology is known in the art (e.g., see technology from Cambridge Antibody Technology (CAT)) as disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593, 081, as well as other U.S. family members, or applications which rely on priority filing GB 9206318, filed 24 May 1992; see also Vaughn, et al. 1996, Nature Biotechnology 14: 309-314). Single chain antibodies may also be designed and constructed using available recombinant DNA technology, such as a DNA amplification method (e.g., PCR), or possibly by using a respective hybridoma cDNA as a template.

Variant antibodies also are included within the scope of the invention. Thus, variants of the sequences recited in the application also are included within the scope of the invention. Further variants of the antibody sequences having improved affinity can be obtained using methods known in the art and are included within the scope of the invention. For example, amino acid substitutions can be used to obtain antibodies with further improved affinity. Alternatively, codon optimization of the nucleotide sequence can be used to improve the efficiency of translation in expression systems for the production of the antibody.

Such variant antibody sequences will share 70% or more (i.e., 80%, 85%, 90%, 95%, 97%, 98%, 99% or greater) sequence identity with the sequences recited in the application. Such sequence identity is calculated with regard to the full length of the reference sequence (i.e., the sequence recited in the application). Percentage identity, as referred to herein, is as determined using BLAST version 2.1.3 using the default parameters specified by the NCBI (the National Center for Biotechnology Information) [Blosum 62 matrix; gap open penalty=11 and gap extension penalty=1]. For example, peptide sequences are provided by this invention that comprise at least about 5, 10, 15, 20, 30, 40, 50, 75, 100, 150, or more contiguous peptides of one or more of the sequences disclosed herein as well as all intermediate lengths there between. As used herein, the term "intermediate lengths" is meant to describe any length between the quoted values, such as 7, 8, 9, 10, 11, 12, 13, 14, 15, 16, 17, 18, 19, etc.; 21, 22, 23, etc.; 30, 31, 32, etc.; 50, 51, 52, 53, etc.; 100, 101, 102, 103, etc.; 150, 151, 152, 153, etc.

The present invention provides for antibodies, either alone or in combination with other antibodies, such as, but not limited to, VRC01, anti-V3 loop, CD4bs, and CD4i antibodies as well as PG9/PG16-like antibodies, that have broad neutralizing activity in serum.

According to another embodiment, the present invention provides methods for the preparation and administration of an HIV antibody composition that is suitable for administration to a human or non-human primate patient having HIV infection, or at risk of HIV infection, in an amount and according to a schedule sufficient to induce a protective immune response against HIV, or reduction of the HIV virus, in a human.

According to another embodiment, the present invention provides a vaccine comprising at least one antibody of the invention and a pharmaceutically acceptable carrier. According to one embodiment, the vaccine is a vaccine comprising at least one antibody described herein and a pharmaceutically acceptable carrier. The vaccine can include a plurality of the antibodies having the characteristics described herein in any combination and can further include antibodies neutralizing to HIV as are known in the art.

It is to be understood that compositions can be a single or a combination of antibodies disclosed herein, which can be the same or different, in order to prophylactically or therapeutically treat the progression of various subtypes of HIV infection after vaccination. Such combinations can be selected according to the desired immunity. When an antibody is administered to an animal or a human, it can be combined with one or more pharmaceutically acceptable carriers, excipients or adjuvants as are known to one of ordinary skilled in the art. The composition can further include broadly neutralizing antibodies known in the art, including but not limited to, VRC01, b12, anti-V3 loop, CD4bs, and CD4i antibodies as well as PG9/PG16-like antibodies.

Further, with respect to determining the effective level in a patient for treatment of HIV, in particular, suitable animal models are available and have been widely implemented for evaluating the in vivo efficacy against HIV of various gene therapy protocols (Sarver et al. (1993b), supra). These models include mice, monkeys and cats. Even though these animals are not naturally susceptible to HIV disease, chimeric mice models (for example, SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection).

According to another embodiment, the present invention provides an antibody-based pharmaceutical composition comprising an effective amount of an isolated HIV antibody, or an affinity matured version, which provides a prophylactic or therapeutic treatment choice to reduce infection of the HIV virus. The antibody-based pharmaceutical composition of the present invention may be formulated by any number of strategies known in the art (e.g., see McGoff and Scher, 2000, Solution Formulation of Proteins/Peptides: In McNally, E. J., ed. Protein Formulation and Delivery. New York, N.Y.: Marcel Dekker; pp. 139-158; Akers and Defilippis, 2000, Peptides and Proteins as Parenteral Solutions. In: Pharmaceutical Formulation Development of Peptides and Proteins. Philadelphia, Pa.: Talyor and Francis; pp. 145-177; Akers, et al., 2002, Pharm. Biotechnol. 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed.

The above described antibodies and antibody compositions or vaccine compositions, comprising at least one or a combination of the antibodies described herein, can be administered for the prophylactic and therapeutic treatment of HIV viral infection.

The present invention also relates to isolated polypeptides comprising the novel amino acid sequences of the light chains and heavy chains, as well as the consensus sequences for the heavy and light chains of SEQ ID NOs: 1 and 2, as listed in FIG. 3.

In other related embodiments, the invention provides polypeptide variants that encode the amino acid sequences of the HIV antibodies listed in FIG. 3; the consensus sequences for the heavy and light chains of SEQ ID NOs: 1 and 2. These polypeptide variants have at least 70%, 75%, 80%, 85%, 90%, 95%, 96%, 97%, 98%, or 99%, or greater, sequence identity compared to a polypeptide sequence of this invention, as determined using the methods described herein, (for example, BLAST analysis using standard parameters). One skilled in this art will recognize that these values can be appropriately adjusted to determine corresponding identity of proteins encoded by taking into amino acid similarity and the like.

The term "polypeptide" is used in its conventional meaning, i.e., as a sequence of amino acids. The polypeptides are not limited to a specific length of the product. Peptides, oligopeptides, and proteins are included within the definition of polypeptide, and such terms can be used interchangeably herein unless specifically indicated otherwise. This term also includes post-expression modifications of the polypeptide, for example, glycosylations, acetylations, phosphorylations and the like, as well as other modifications known in the art, both naturally occurring and non-naturally occurring. A polypeptide can be an entire protein, or a subsequence thereof. Particular polypeptides of interest in the context of this invention are amino acid subsequences comprising CDRs, VH and VL, being capable of binding an antigen or HIV-infected cell.

A polypeptide "variant," as the term is used herein, is a polypeptide that typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of techniques well known in the art.

For example, certain amino acids can be substituted for other amino acids in a protein structure without appreciable loss of its ability to bind other polypeptides (for example, antigens) or cells. Since it is the binding capacity and nature of a protein that defines that protein's biological functional activity, certain amino acid sequence substitutions can be made in a protein sequence, and, accordingly, its underlying DNA coding sequence, whereby a protein with like properties is obtained. It is thus contemplated that various changes can be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

Amino acid substitutions generally are based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

"Homology" or "sequence identity" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least about 70%, at least about 75%, at least about 80%, at least about 90%, at least about 95%, at least about 98%, or at least about 99% polynucleotide or polypeptide homology with a polynucleotide or polypeptide described herein.

Such variant polypeptide sequences will share 70% or more (i.e. 80%, 85%, 90%, 95%, 97%, 98%, 99% or more) sequence identity with the sequences recited in the application. In additional embodiments, the described invention provides polypeptide fragments comprising various lengths of contiguous stretches of amino acid sequences disclosed herein. For example, peptide sequences are provided by this invention that comprise at least about 5, 10, 15, 20, 30, 40, 50, 75, 100, 150, or more contiguous peptides of one or more of the sequences disclosed herein as well as all intermediate lengths there between.

The invention also includes nucleic acid sequences encoding part or all of the light and heavy chains of the described inventive antibodies, and fragments thereof. Due to redundancy of the genetic code, variants of these sequences will exist that encode the same amino acid sequences.

The present invention also includes isolated nucleic acid sequences encoding the polypeptides for the heavy and light chains of the HIV antibodies listed in FIG. 3 and the consensus sequences for the heavy and light chains of SEQ ID NOs: 1 and 2.

In other related embodiments, the described invention provides polynucleotide variants that encode the peptide sequences of the heavy and light chains of the HIV antibodies listed in FIG. 3; the consensus sequences for the heavy and light chains of SEQ ID NOs: 1 and 2. These polynucleotide variants have at least 70%, at least 75%, at least 80%, at least 85%, at least 90%, at least 95%, at least 96%, at least 97%, at least 98%, or at least 99%, or greater, sequence identity compared to a polynucleotide sequence of this invention, as determined using the methods described herein, (for example, BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

The terms "nucleic acid" and "polynucleotide" are used interchangeably herein to refer to single-stranded or double-stranded RNA, DNA, or mixed polymers. Polynucleotides can include genomic sequences, extra-genomic and plasmid sequences, and smaller engineered gene segments that express, or can be adapted to express polypeptides.

An "isolated nucleic acid" is a nucleic acid that is substantially separated from other genome DNA sequences as well as proteins or complexes such as ribosomes and polymerases, which naturally accompany a native sequence. The term encompasses a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Accordingly, this refers to the nucleic acid as originally isolated and does not exclude genes or sequences later added to the isolated nucleic acid by the hand of man.

A polynucleotide "variant," as the term is used herein, is a polynucleotide that typically differs from a polynucleotide specifically disclosed herein in one or more substitutions, deletions, additions and/or insertions. Such variants can be naturally occurring or can be synthetically generated, for example, by modifying one or more of the polynucleotide sequences of the invention and evaluating one or more biological activities of the encoded polypeptide as described herein and/or using any of a number of techniques well known in the art.

Modifications can be made in the structure of the polynucleotides of the described invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art typically will change one or more of the codons of the encoding DNA sequence.

Typically, polynucleotide variants contain one or more substitutions, additions, deletions and/or insertions, such that the immunogenic binding properties of the polypeptide encoded by the variant polynucleotide is not substantially diminished relative to a polypeptide encoded by a polynucleotide sequence specifically set forth herein.

In additional embodiments, the described invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between and encompass any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; and including all integers through 200-500; 500-1,000.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderate stringent conditions for testing the hybridization of a polynucleotide of this invention with other polynucleotides include prewashing in a solution of 5×SSC, 0.5% SDS, 1.0 mM EDTA (pH 8.0); hybridizing at 50-60° C., 5×SSC, overnight; followed by washing twice at 65° C. for 20 minutes with each of 2×, 0.5×, and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, for example, to 60-65° C. or 65-70° C.

In some embodiments, the polypeptide encoded by the polynucleotide variant or fragment has the same binding specificity (i.e., specifically or preferentially binds to the same epitope or HIV strain) as the polypeptide encoded by the native polynucleotide. In some embodiments, the described polynucleotides, polynucleotide variants, fragments and hybridizing sequences, encode polypeptides that have a level of binding activity of at least about 50%, at least about 70%, and at least about 90% of that for a polypeptide sequence specifically set forth herein.

The polynucleotides of the described invention, or fragments thereof, regardless of the length of the coding sequence itself, can be combined with other DNA sequences, such as promoters, polyadenylation signals, additional restriction enzyme sites, multiple cloning sites, other coding segments, and the like, such that their overall length can vary considerably. A nucleic acid fragment of almost any length is employed. For example, illustrative polynucleotide segments with total lengths of about 10000, about 5000, about 3000, about 2000, about 1000, about 500, about 200, about 100, about 50 base pairs in length, and the like, (including all intermediate lengths) are included in many implementations of this invention.

Further included within the scope of the invention are vectors such as expression vectors, comprising a nucleic acid sequence according to the invention. Cells transformed with such vectors also are included within the scope of the invention.

The present invention also provides vectors and host cells comprising a nucleic acid of the invention, as well as recombinant techniques for the production of a polypeptide of the invention. Vectors of the invention include those capable of replication in any type of cell or organism, including, for example, plasmids, phage, cosmids, and mini chromosomes. In some embodiments, vectors comprising a polynucleotide of the described invention are vectors suitable for propagation or replication of the polynucleotide, or vectors suitable for expressing a polypeptide of the described invention. Such vectors are known in the art and commercially available.

"Vector" includes shuttle and expression vectors. Typically, the plasmid construct also will include an origin of replication (for example, the ColE1 origin of replication) and a selectable marker (for example, ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

As used herein, the term "cell" can be any cell, including, but not limited to, that of a eukaryotic, multicellular species (for example, as opposed to a unicellular yeast cell), such as, but not limited to, a mammalian cell or a human cell. A cell can be present as a single entity, or can be part of a larger collection of cells. Such a "larger collection of cells" can comprise, for example, a cell culture (either mixed or pure), a tissue (for example, endothelial, epithelial, mucosa or other tissue), an organ (for example, lung, liver, muscle and other organs), an organ system (for example, circulatory system, respiratory system, gastrointestinal system, urinary system, nervous system, integumentary system or other organ system), or an organism (e.g., a bird, mammal, or the like).

Polynucleotides of the invention may synthesized, whole or in parts that then are combined, and inserted into a vector using routine molecular and cell biology techniques, including, for example, subcloning the polynucleotide into a linearized vector using appropriate restriction sites and restriction enzymes. Polynucleotides of the described invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the invention, the nucleotide sequences encoding the polypeptide, or functional equivalents, may be inserted into an appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

The present invention also provides kits useful in performing diagnostic and prognostic assays using the antibodies, polypeptides and nucleic acids of the present invention. Kits of the present invention include a suitable container comprising an HIV antibody, a polypeptide or a nucleic acid of the invention in either labeled or unlabeled form. In addition, when the antibody, polypeptide or nucleic acid is supplied in a labeled form suitable for an indirect binding assay, the kit further includes reagents for performing the appropriate indirect assay. For example, the kit may include one or more suitable containers including enzyme substrates or derivatizing agents, depending on the nature of the label. Control samples and/or instructions may also be included. The present invention also provides kits for detecting the presence of the HIV antibodies or the nucleotide sequence of the HIV antibody of the present invention in a biological sample by PCR or mass spectrometry.

"Label" as used herein refers to a detectable compound or composition that is conjugated directly or indirectly to the antibody so as to generate a "labeled" antibody. A label can also be conjugated to a polypeptide and/or a nucleic acid sequence disclosed herein. The label can be detectable by itself (for example, radioisotope labels or fluorescent labels) or, in the case of an enzymatic label, can catalyze chemical alteration of a substrate compound or composition that is detectable. Antibodies and polypeptides of the described invention also can be modified to include an epitope tag or label, for example, for use in purification or diagnostic applications. Suitable detection means include the use of labels such as, but not limited to, radionucleotides, enzymes, coenzymes, fluorescers, chemiluminescers, chromogens, enzyme substrates or co-factors, enzyme inhibitors, prosthetic group complexes, free radicals, particles, dyes, and the like.

According to another embodiment, the present invention provides diagnostic methods. Diagnostic methods generally involve contacting a biological sample obtained from a patient, such as, for example, blood, serum, saliva, urine, sputum, a cell swab sample, or a tissue biopsy, with an HIV antibody and determining whether the antibody preferentially binds to the sample as compared to a control sample or predetermined cut-off value, thereby indicating the presence of the HIV virus.

According to another embodiment, the present invention provides methods to detect the presence of the HIV antibodies of the present invention in a biological sample from a patient. Detection methods generally involve obtaining a biological sample from a patient, such as, for example, blood, serum, saliva, urine, sputum, a cell swab sample, or a tissue biopsy and isolating HIV antibodies or fragments thereof, or the nucleic acids that encode an HIV antibody, and assaying for the presence of an HIV antibody in the biological sample. Also, the present invention provides methods to detect the nucleotide sequence of an HIV antibody in a cell. The nucleotide sequence of an HIV antibody may also be detected using the primers disclosed herein. The presence of the HIV antibody in a biological sample from a patient may be determined utilizing known recombinant techniques and/or the use of a mass spectrometer.

In another embodiment, the present invention provides a method for detecting an HIV antibody comprising a heavy chain comprising a highly conserved consensus sequence and a light chain comprising a highly conserved consensus sequence in a biological sample, comprising obtaining an immunoglobulin-containing biological sample from a mammalian subject, isolating an HIV antibody from said sample, and identifying the highly conserved consensus sequences of the heavy chain and the light chain. The biological sample may be blood, serum, saliva, urine, sputum, a cell swab sample, or a tissue biopsy. The amino acid sequences may be determined by methods known in the art including, for example, PCR and mass spectrometry.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

II. Method of Reducing Viral Replication

Methods for reducing an increase in HIV virus titer, virus replication, virus proliferation or an amount of an HIV viral protein in a subject are further provided. According to another aspect, a method includes administering to the subject an amount of an HIV antibody effective to reduce an increase in HIV titer, virus replication or an amount of an HIV protein of one or more HIV strains or isolates in the subject.

According to another embodiment, the present invention provides a method of reducing viral replication or spread of HIV infection to additional host cells or tissues comprising contacting a mammalian cell with the antibody, or a portion thereof, which binds to an antigenic epitope on gp120.

III. Method of Treatment

According to another embodiment, the present invention provides a method for treating a mammal infected with a virus infection, such as, for example, HIV, comprising administering to said mammal a pharmaceutical composition comprising the HIV antibodies disclosed herein. According to one embodiment, the method for treating a mammal infected with HIV comprises administering to said mammal a pharmaceutical composition that comprises an antibody of the present invention, or a fragment thereof. The compositions of the invention can include more than one antibody having the characteristics disclosed (for example, a plurality or pool of antibodies). It also can include other HIV neutralizing antibodies as are known in the art, for example, but not limited to, VRC01, PG9 and b12.

Passive immunization has proven to be an effective and safe strategy for the prevention and treatment of viral diseases. (See, for example, Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999). Passive immunization using human monoclonal antibodies provides an immediate treatment strategy for emergency prophylaxis and treatment of HIV.

Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

For in vivo treatment of human and non-human patients, the patient is administered or provided a pharmaceutical formulation including an HIV antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, for example, as a bolus or by continuous infusion over a period of time, by intramuscular, intraperitoneal, intracerobrospinal, subcutaneous, intra-articular, intrasynovial, intrathecal, oral, topical, or inhalation routes. The antibodies can be administered parenterally, when possible, at the target cell site, or intravenously. In some embodiments, antibody is administered by intravenous or subcutaneous administration. Therapeutic compositions of the invention may be administered to a patient or subject systemically, parenterally, or locally. The above parameters for assessing successful treatment and improvement in the disease are readily measurable by routine procedures familiar to a physician.

For parenteral administration, the antibodies may be formulated in a unit dosage injectable form (solution, suspension, emulsion) in association with a pharmaceutically acceptable, parenteral vehicle. Examples of such vehicles include, but are not limited, water, saline, Ringer's solution, dextrose solution, and 5% human serum albumin. Nonaqueous vehicles include, but are not limited to, fixed oils and ethyl oleate. Liposomes can be used as carriers. The vehicle may contain minor amounts of additives such as substances that enhance isotonicity and chemical stability, such as, for example, buffers and preservatives. The antibodies can be formulated in such vehicles at concentrations of about 1 mg/ml to 10 mg/ml.

The dose and dosage regimen depends upon a variety of factors readily determined by a physician, such as the nature of the infection, for example, its therapeutic index, the patient, and the patient's history. Generally, a therapeutically effective amount of an antibody is administered to a patient. In some embodiments, the amount of antibody administered is in the range of about 0.1 mg/kg to about 50 mg/kg of patient body weight. Depending on the type and severity of the infection, about 0.1 mg/kg to about 50 mg/kg body weight (for example, about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art. The above parameters for assessing successful treatment and improvement in the disease are readily measurable by routine procedures familiar to a physician.

Other therapeutic regimens may be combined with the administration of the HIV antibody of the present invention. The combined administration includes co-administration, using separate formulations or a single pharmaceutical formulation, and consecutive administration in either order, wherein preferably there is a time period while both (or all) active agents simultaneously exert their biological activities. Such combined therapy can result in a synergistic therapeutic effect. The above parameters for assessing successful treatment and improvement in the disease are readily measurable by routine procedures familiar to a physician.

The terms "treating" or "treatment" or "alleviation" are used interchangeably and refer to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to treat a disease or disorder in a subject or mammal.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but not limited to, buffers such as phosphate, citrate, and other organic acids; antioxidants including, but not limited to, ascorbic acid; low molecular weight (less than about 10 residues) polypeptide; proteins, such as, but not limited to, serum albumin, gelatin, or immunoglobulins; hydrophilic polymers such as, but not limited to, polyvinylpyrrolidone; amino acids such as, but not limited to, glycine, glutamine, asparagine, arginine or lysine; monosaccharides, disaccharides, and other carbohydrates including, but not limited to, glucose, mannose, or dextrins; chelating agents such as, but not limited to, EDTA; sugar alcohols such as, but not limited to, mannitol or sorbitol; salt-forming counterions such as, but not limited to, sodium; and/or nonionic surfactants such as, but not limited to, TWEEN; polyethylene glycol (PEG), and PLURONICS.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

EXAMPLE 1

This example describes materials and methods used in EXAMPLES 2-5 below.

HIV antibodies were cloned and produced following gp140-specific single B-cell capture as previously described (Mouquet, H. et al. PLoS One 6, e24078 (2011); Tiller, T. et al. J Immunol Methods 329, 112-24 (2008); and Scheid, J. F. et al. Nature 458, 636-40 (2009)). PGT121$_{GM}$ and 10-1074$_{GM}$ "glycomutant" antibodies were generated by substituting 10-1074 residues at HC positions 32, 53, 54, 58, 97, 100I into PGT121 and vice versa. Binding properties of anti-gp140 antibodies to HIV Env proteins were assayed by ELISA, SPR and glycan microarray assays as previously described (Scheid, J. F. et al. Science 333, 1633-7 (2011); Walker, L. M. et al. Nature 477, 466-70 (2011); and Mouquet, H. et al. PLoS One 6, e24078 (2011)). Neutralization was evaluated using (i) a luciferase-based assay in TZM.b1 cells, and (ii) a PBMC-based assay using infection with primary HIV-1 variants as previously described (Li, M. et al. J Virol 79, 10108-25 (2005); Euler, Z. et al. Journal of virology 85, 7236-45 (2011); and Bunnik, E. M. et al. Nature medicine 16, 995-7 (2010)). Structures of PGT121 ("unliganded" and "liganded"), 10-1074 and GL Fab fragments were solved by molecular replacement to 2.8 Å, 2.3 Å, 1.8 Å and 2.4 Å resolution, respectively.

Single B Cell RT-PCRs and Ig Gene Analyses

Single-cell sorting of gp140$^+$CD19$^+$IgG$^+$ B cells from patient 10 (pt10; referred to as patient 17 in Nature 477 (7365):466-470.) PBMCs, cDNA synthesis and nested PCR amplifications of Ig genes were performed in a previous study (PLoS One 6(9):e24078). Igλ genes expressed by PGT121 clonal variants were PCR amplified using a forward primer (L-Vλ3-21*02: 5' CTGGACCGTTCTCCTCCTCG 3' (SEQ ID NO: 137)) further upstream in the leader region to avoid the potentially mutated region (31). All PCR products were sequenced and analyzed for Ig gene usage, CDR3 analyses and number of VH/Vκ somatic hypermutations (IgBLAST and IMGT®). Multiple sequence alignments were performed using the MacVector program (v.12.5.0) with the ClustalW analysis function (default parameters), and were used to generate dendrograms by the Neighbor Joining method (with Best tree mode and outgroup rooting). Alternatively, dendrograms were generated using the UPGMA method (with Best tree mode).

The germline (GL) precursor gene segments of the PGT121-like and 10-1074-like antibodies were identified using IgBLAST and IMGT®/V-QUEST as V$_H$4-59*01, J$_H$6*03, V$_L$3-21*02 and J$_L$3*02. (These gene segments are among the most frequently used in the repertoire of human antibodies (PLoS One 6(8):e22365; Immunogenetics 64(5): 337-350). To build a representative GL ancestor sequence, we aligned the IgH and IgL sequences of 10-996 (the antibody containing the fewest somatic hypermutations) to the GL sequences using IgBLAST. The GL IgH sequence was constructed by replacing the mature V$_H$ and J$_H$ gene segments with their GL counterparts and using the 10-996 sequence for the CDRH3 region involving N-region nucleotides and the DH gene segment. The GL IgL sequence was assembled from the $V_L3$-21*02 and $J_L3$*02 gene segment sequences.

Cloning and Production of Antibodies

Purified digested PCR products were cloned into human Igγ$_1$-, or Igλ-expressing vectors (J Immunol Methods 329 (1-2):112-124). Vectors containing IgH and Igλ genes were then sequenced and compared to the original PCR product sequences. PGT121 and 10-303 shared the same Igλ gene and had one amino acid difference in position 2 of the IgH gene (FIG. 4); therefore to produce the PGT121 IgG, we used the 10-303 Igλ gene and a PGT121 IgH gene generated by introducing a single substitution (V2M) into the 10-303 IgH gene by site-directed mutagenesis (QuikChange Site-Directed Mutagenesis Kit; Stratagene). To generate His-tagged Fabs, the PGT121 and 10-1074 $V_H$ genes were subcloned into a 6×His-IgCγ1 ('6×His' disclosed as SEQ ID NO: 138) expression vector generated by modifying our standard Igγ$_1$ vector (Science 301(5638):1374-1377) to encode the IgG1 $C_H1$ domain followed by a 6×-His tag (SEQ ID NO: 138). IgH DNA fragments encoding PGT121$_{GM}$ (S32Y, K53D, S54R, N58T, H97R, T1001Y) and 10-1074$_{GM}$ (Y32S, D53K, R54S, T58N, R97H, Y1001T) mutant antibodies were obtained as a synthetic minigene (IDT) and subcloned into Igγ$_1$-expressing vectors.

Listed below is the heavy chain sequence for 10-1074$_{GM}$ where the mutations are underlined. The light chain sequence of 10-1074$_{GM}$ is the same as that of 10-1074.

```
                                          (SEQ ID NO: 129)
QVQLQESGPGLVKPSETLSVTCSVSGDSMNNSYWTWIRQSPGKGLEWIGY
ISKSESANYNPSLNSRVVISRDTSKNQLSLKLNSVTPADTAVYYCATARH
GQRIYGVVSFGEFFTYYSMDVWGKGTTVTVSS
```

Antibodies and Fab fragments were produced by transient transfection of IgH and IgL expression plasmids into exponentially growing HEK 293T cells (ATCC, CRL-11268) using the polyethyleneimine (PEI)-precipitation method (PLoS One 6(9):e24078). IgG antibodies were affinity purified using Protein G sepharose beads (GE Healthcare) according to the manufacturer's instructions. Fab fragments were affinity purified using HisPur™ Cobalt Resin (Thermo scientific) as described below.

HIV-1 Env Proteins

Alanine mutations were introduced into the pYU-2 gp120 vector (gift of J. Sodroski, Harvard Medical School) at positions 301 to 303 (Asn-Asn-Thr), 324 to 325 (Gly-Asp), and 332 (Asn) (HXBc2 amino acid numbering) using the QuikChange Site-Directed Mutagenesis kit (Stratagene) according to the manufacturer's instructions. The same procedure was used to generate "double glycan" mutants by introducing single alanine mutations in the pYU-2 gp120$^{N332A}$ vector at each PNGS located between Asn262$_{gp120}$ and Asn406$_{gp120}$. Site-directed mutations were verified by DNA sequencing.

Expression vectors encoding YU-2 gp140 (Journal of virology 74(12):5716-5725), YU-2 gp120, HXB2c gp120$^{core}$ (Nature 393(6686):648-659), HXB2c 2CCcore (PLoS Pathog 5(5):e1000445) proteins, and YU-2 gp120 mutant proteins were used to transfect HEK 293T cells. To produce high-mannose-only YU-2 gp120 protein (gp120$_{kif}$), 25 μM kifunensine (Enzo Life Sciences) was added at the time of transfection. Culture supernatants were harvested and concentrated using centrifugation-based filtration devices (Vivacell 100, Sartorius Stedim Biotech Gmbh) that allowed buffer exchange of the samples into 10 mM imidazole, 50 mM sodium phosphate, 300 mM sodium chloride; pH 7.4. Proteins were purified by affinity chromatography using HisPur™ Cobalt Resin (Thermo scientific) according to the manufacturer's instructions.

For deglycosylation reactions, 50 μg of HEK 293T cell-produced YU-2 gp120 in PBS was digested overnight at 37° C. with 200 U of PNGase F (New England Biolabs) or 10,000 U of Endo H$_f$ (New England Biolabs) in their respective reaction buffers without denaturing agents. After buffer exchange into PBS using Centrifugal Filters (Amicon® Ultra, Millipore), glycosidase-treated gp120s (200 ng) were examined by SDS-PAGE using a 4-12% NuPAGE gel (Invitrogen) followed by silver staining (Pierce Silver Stain Kit, Thermo Scientific).

ELISAs

High-binding 96-well ELISA plates (Costar) were coated overnight with 100 ng/well of purified gp120 in PBS. After washing, the plates were blocked for 2 h with 2% BSA, 1 μM EDTA, 0.05% Tween-PBS (blocking buffer) and then incubated for 2 h with IgGs at concentrations of 26.7 nM (or 427.2 nM for ELISAs using the YU-2 gp120 double glycan mutants) and 7 consecutive 1:4 dilutions in PBS. After washing, the plates were developed by incubation with goat HRP-conjugated anti-human IgG antibodies (Jackson ImmunoReseach) (at 0.8 μg/ml in blocking buffer) for 1 h, and by addition of HRP chromogenic substrate (ABTS solution, Invitrogen) (PLoS One 6(9):e24078). Antibody binding to the selected gp120$^{V3}$ overlapping peptides was tested using a previously described peptide-ELISA method.

For competition ELISAs, gp120-coated plates were blocked for 2 h with blocking buffer and then incubated for 2 h with biotinylated antibodies (at a concentration of 26.6 nM for PGT121, 0.21 nM for 10-1074, 0.43 nM for 10-996 and 1.67 nM for 10-1369) in 1:2 serially diluted solutions of antibody competitors in PBS (IgG concentration range from 5.2 to 667 nM). Plates were developed as described above using HRP-conjugated streptavidin (Jackson ImmunoReseach) (at 0.8 μg/ml in blocking buffer). All experiments were performed at least in duplicate.

Glycan Microarray Analysis

Figure 7A:
FIGS. 7A and 7B depict: Binding of PGT121 and 10-1074 clonal variants to glycans.

Microarrays were generated by robotically printing glycan probes linked to lipid (neoglycolipids) onto nitrocellulose-coated glass slides (Methods Mol Biol 808:117-136) at two levels (2 and 5 fmol/spot) in duplicate. Binding assays were performed with microarrays containing 15 neoglycolipids derived from N-glycans of high-mannose and complex-types. The sequences of the probes are shown in FIG. 7A. In brief, antibodies were tested at 50 μg/ml, and binding was detected with biotinylated anti-human IgG (Vector) followed by AlexaFluor 647-labeled streptavidin (Molecular Probes).

Surface Plasmon Resonance

Figures 8A, 8B:
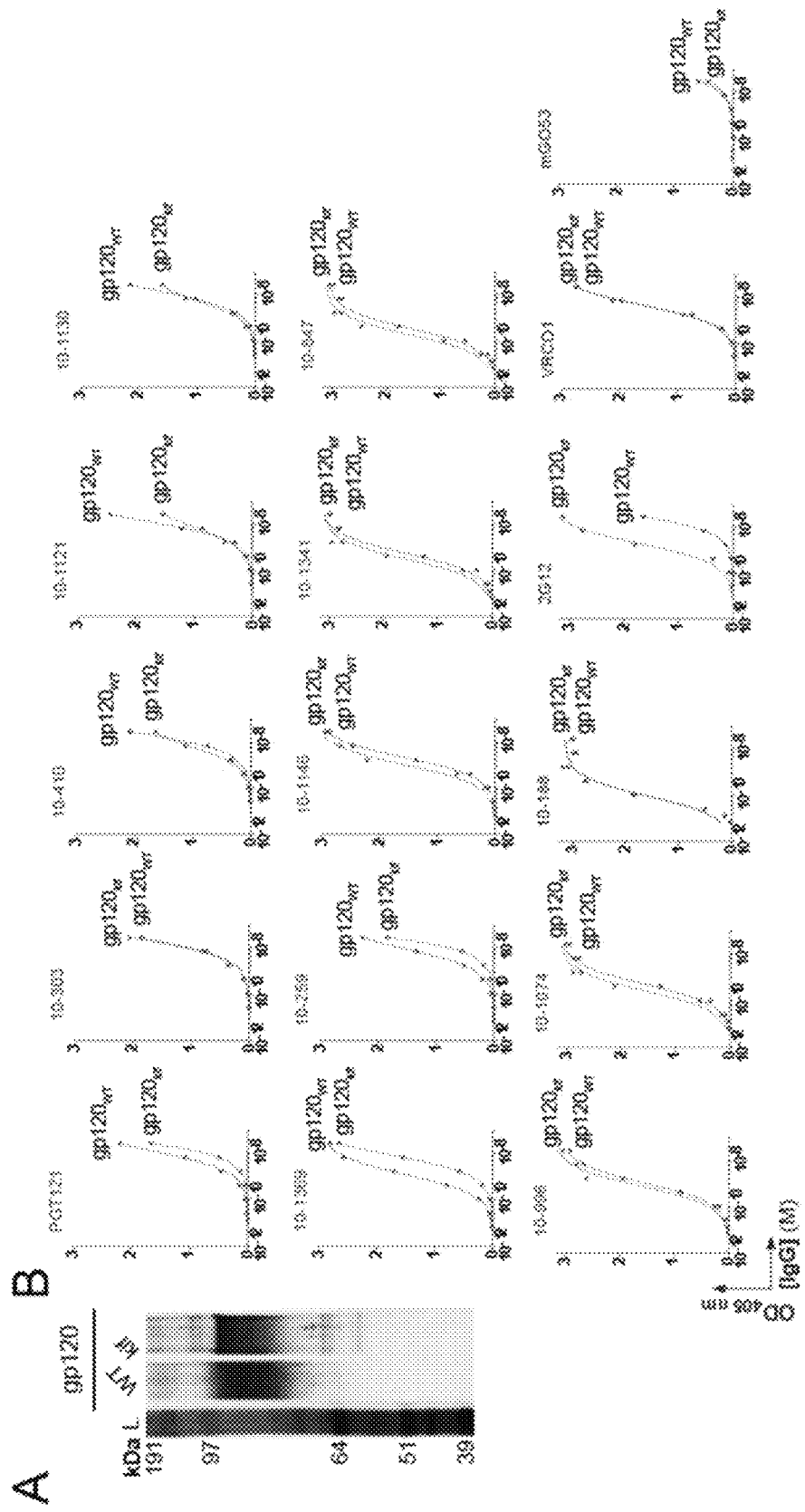
FIGS. 8A, 8B, 8C and 8D depict: Antibody binding and neutralization activity against high-mannose-only gp120 and viruses. (A) Silver-stained SDS-PAGE gel comparing YU-2 gp120 produced in cells treated with kifunensine (gp120$_{kif}$) and gp120 produced in untreated cells (WT, wild type). L, protein ladder. (B) ELISA comparison of the binding of PGT121-like (blue labels) and 10-1074-like (green labels) antibodies to YU-2 gp120 (gp120$_{WT}$) and gp120$_{kif}$. The x axis shows the antibody concentration (M) required to obtain the ELISA values ($OD_{405\ nm}$) indicated on the y axis. (C) Neutralization curves for PGT121 evaluated against selected PGT121-sensitive/10-1074-resistant pseudoviruses produced in presence (Virus$_{kif}$) or absence (Virus$_{WT}$) of kifunensine. The dotted horizontal line indicates 50% neutralization, from which the $IC_{50}$ value can be derived from the antibody concentration on the x axis. Experiments were performed in triplicate. Error bars indicate the SD of triplicate measurements. (D) Bar graphs comparing the neutralization activity of selected antibodies against YU-2 and PVO.4 pseudoviruses produced in HEK 293S GnTI$^{-/-}$cells (Virus$_{GnT}^{-/-}$) or in wild type cells (Virus$_{WT}$). The y axis shows the mean $IC_{50}$ values (μg/ml) for the neutralization of the viruses shown on the x axis. Error bars indicate the SEM of $IC_{50}$ so values obtained from two independent experiments.
Figures 8C, 8D:
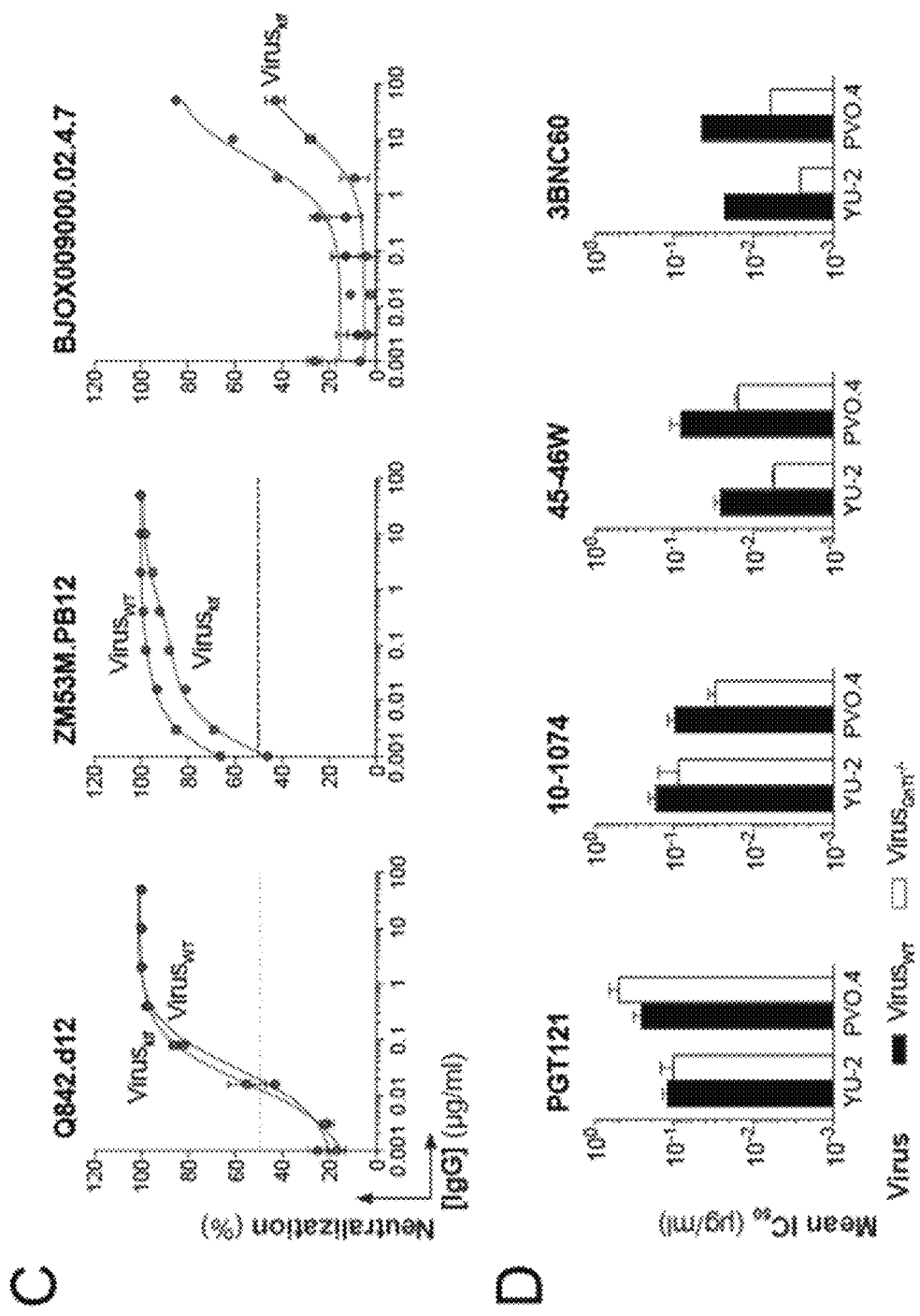

Experiments were performed using a Biacore T100 (Biacore, Inc)(Nature 467(7315):591-595). Briefly, YU-2 gp140 and gp120 proteins were primary amine-coupled on CM5 chips (Biacore, Inc.) at a coupling density of 300 RUs. Anti-gp120 IgGs and the germline precursor (GL) were injected over flow cells at 1 μM and 10 μM, respectively, at flow rates of 35 μl/min with 3 min association and 5 min dissociation phases. The sensor surface was regenerated by a 30 sec injection of 10 mM glycine-HCl pH 2.5 at a flow rate of 50 μl/min. Dissociation ($k_d$ ($s^{-1}$)), association ($k_a$ ($M^{-1}$ $s^{-1}$)) and binding constants ($K_D$ (M) or $K_A$ ($M^{-1}$)) were calculated from kinetic analyses after subtraction of backgrounds using a 1:1 binding model without a bulk reflective index (RI) correction (Biacore T100 Evaluation software). Binding constants for bivalent IgGs calculated using a 1:1 binding model are referred to in the text as "apparent" affinities to emphasize that the $K_D$ values include potential avidity effects Neutralization Assays Virus neutralization was evaluated using a luciferase-based assay in TZM.b1 cells (J Virol 79(16):10108-10125). The HIV-1 pseudoviruses tested contained mostly tier-2 and tier-3 viruses (Journal of virology 84(3):1439-1452) (Tables 4 and 5). High-mannose-only pseudoviruses were produced in wild-type cells treated with 25 µM kifunensine (Enzo Life Sciences) (FIG. 8C) or in HEK 293S GnTI$^{-/-}$ cells (FIG. 8D). Non-linear regression analysis was used to calculate concentrations at which half-maximal inhibition was observed ($IC_{50}$ values). Neutralization activities were also evaluated with a previously characterized PBMC-based assay using infection with primary HIV-1 variants (n=95) isolated from clade B-infected donors with known seroconversion dates either between 1985 and 1989 ("historical seroconverters", n=14) or between 2003 and 2006 ("contemporary seroconverters", n=21) (Journal of virology 85(14):7236-7245; Nat Med 16(9):995-997). Neutralization activity for each antibody was calculated using GraphPad Prism software (v5.0b) as area under the best-fit curve, which fits the proportion of viruses neutralized over $IC_{50}$ values ranging from 0.001 to 50 µg/ml. Relative area under the curve (RAUC) values were derived by normalizing all AUC values by the highest value (obtained with 10-1074).

Statistical Analyses

Statistical analyses were performed with the GraphPad Prism software (v5.0b). Neutralization potencies in the TZM-b1 assay against the selected panel of 9 virus strains versus the apparent binding affinities of the antibodies for gp120 and gp140 were analyzed using a Spearman's correlation test. The Mann Whitney test was used to compare: (i) affinities for gp120/gp140 of antibodies belonging to the PGT121 or 10-1074 group, and (ii) neutralization activities against viruses isolated from historical and contemporary seroconverters.

Crystallization and Structure Determinations

6×-His (SEQ ID NO: 138) tagged PGT121, 10-1074 and 10-996GL Fabs for crystallization were expressed. Fabs were purified from the supernatants of transiently-transfected HEK 293-6E cells by sequential Ni$^{2+}$-NTA affinity (Qiagen) and Superdex200 10/300 (GE Healthcare) size exclusion chromatography. For crystals of the unliganded PGT121 Fab, PGT121 IgG was isolated from the supernatants of transiently-transfected HEK 293-6E cells by Protein A affinity chromatography (Pierce), and Fab fragments were obtained by papain cleavage of the IgG and further purification using Superdex200 10/300 (GE Healthcare) size exclusion chromatography.

Purified Fabs were concentrated to 8-20 mg/mL ("unliganded" PGT121, 8 mg/mL; 10-1074 and GL, 20 mg/mL) in PBS buffer. The "liganded" PGT121 Fab crystals were prepared from a protein sample (final concentration: 15 mg/mL) that was mixed with a 3-fold molar excess of NA2 glycan and incubated at 20° C. for 2 hours. Crystallization conditions were screened at 20° C. using a Mosquito® crystallization robot (TTP labs) in 400 nL drops using a 1:1 protein to reservoir ratio. Crystals of "unliganded" PGT121 Fab ($P2_12_12_1$; a=56.8, b=74.7, c=114.9 Å) were obtained in 24% PEG 4,000, 0.1 M Tris-HCl pH 8.5, 10 mM CuCl$_2$ and crystals of "liganded" PGT121 Fab ($P2_12_12_1$; a=67.8, b=67.8, c=94.1 Å) grew in 17% PEG 10,000, 0.1M Bis-Tris pH 5.5, 0.1M CH$_3$COOHNH$_4$. Crystals of 10-1074 Fab ($P2_1$; a=61.4, b=40.3, c=84.5 Å; β=95.39°) were obtained in 25% PEG 3,350, 0.1 M Bis-Tris pH 5.5, 0.2 M NaCl, and crystals of GL Fab ($P2_1$; a=54.9, b=344.7, c=55.2 Å; β91.95°) grew in 20% PEG 3,350, 0.24 M sodium malonate pH 7.0, 10 mM MnCl$_2$. Crystals were cryoprotected by soaking in mother liquor containing 20% glycerol ("unliganded" and "liganded" PGT121 Fab) or 20% ethylene glycol (10-1074 Fab and GL Fab) and subsequently flash-cooled in liquid nitrogen.

Diffraction data were collected at beamline 12-2 (wavelength=1.029 Å) at the Stanford Synchrotron Radiation Lightsource (SSRL) on a Pilatus 6M pixel detector (Dectris). Data were indexed, integrated and scaled using XDS. Using the data obtained from the "unliganded" PGT121 Fab crystals, we used Phenix to find a molecular replacement solution for one Fab per asymmetric unit (chains H and L for the heavy and light chain, respectively) using two search models, the $C_H$-$C_L$ domains of PGT128 Fab (PDB code 3PV3) and the $V_H$-$V_L$ domains of 2F5 (PDB code 3IDJ) after omitting residues in the CDRH3 and CDRL3 loops. Subsequently, we used the "unliganded" PGT121 structure as a search model to find molecular replacement solutions for "liganded" PGT121 Fab (one Fab per asymmetric unit), 10-1074 Fab (one Fab per asymmetric unit) and GL (four Fabs per asymmetric unit).

Iterative refinement (including non-crystallographic symmetry restraints for GL) was performed using Phenix and manually fitting models into electron density maps using Coot. The atomic models were refined to 3.0 Å resolution for PGT121 Fab ($R_{work}$=21.6%; $R_{free}$=26.4%), 1.9 Å resolution for 10-1074 Fab ($R_{work}$=18.7%; $R_{free}$=22.3%), 2.4 Å resolution for four GL Fab molecules ($R_{work}$=19.4%; $R_{free}$=23.7%), and 2.4 Å resolution for "liganded" PGT121 Fab ($R_{work}$=20.1%; $R_{free}$=24.9%). The atomic model of PGT121 Fab contains 95.2%, 4.9% and 0.0% of the residues in the favored, allowed and disallowed regions of the Ramachandran plot, respectively (10-1074 Fab: 98.8%, 0.9%, 0.2%; GL Fab: 96.0%, 3.8%, 0.23%; "liganded" PGT121 Fab: 96.7%, 3.1%, 0.2%). PyMOL was used for molecular visualization and to generate figures of the Fab structures. Buried surface area calculations were performed with Areaimol (CCP4 Suite) using a 1.4 Å probe.

Fab structures were aligned using the Super script in PyMOL. Pairwise Cα alignments were performed using PDBeFold.

EXAMPLE 2

Predominance and Diversity of PGT121 Clonotype gp140-specific IgG memory B cells were isolated from a clade A-infected African donor using YU-2 gp140 trimers as "bait." Eighty-seven matching immunoglobulin heavy (IgH) and light (IgL) chain genes corresponding to 23 unique clonal families were identified. The IgH anti-gp140 repertoire was dominated by one clonal family representing ~28% of all expanded B cell clones. This B cell family corresponds to the same clone as PGT121-123 (Nature 477(7365):466-470) and contained 38 members, 29 of which were unique variants at the nucleotide level (Table 3). Based on their IgH nucleotide sequence, the PGT121 family divides into two groups: a PGT121-like group containing PGT121-123 and 9 closely-related variants, and a second group, 10-1074-like, containing 20 members. Although our traditional primers (J Immunol Methods 329(1-2):112-124; Science 301(5638):1374-1377) did not amplify the IgL genes expressed by the PGT121 B cell clone due to the nucleotide deletions in the region encoding framework region 1, 24 of 38 genes were obtained using new Igλ- specific primers designed to amplify heavily somatically-mutated genes (Table 3). Consistent with the high levels of hypermutation in the IgH genes (18.2% of the VH gene on average), the amplified Igλ genes were highly mutated (18.2% of the Vλ gene on average) and carried nucleotide deletions in framework region 1 (FWR1) (12 to 21 nucleotides) and a 9-nucleotide insertion in framework region 3 (FWR3) (FIG. 3B and Table 3).

Figure 3A:
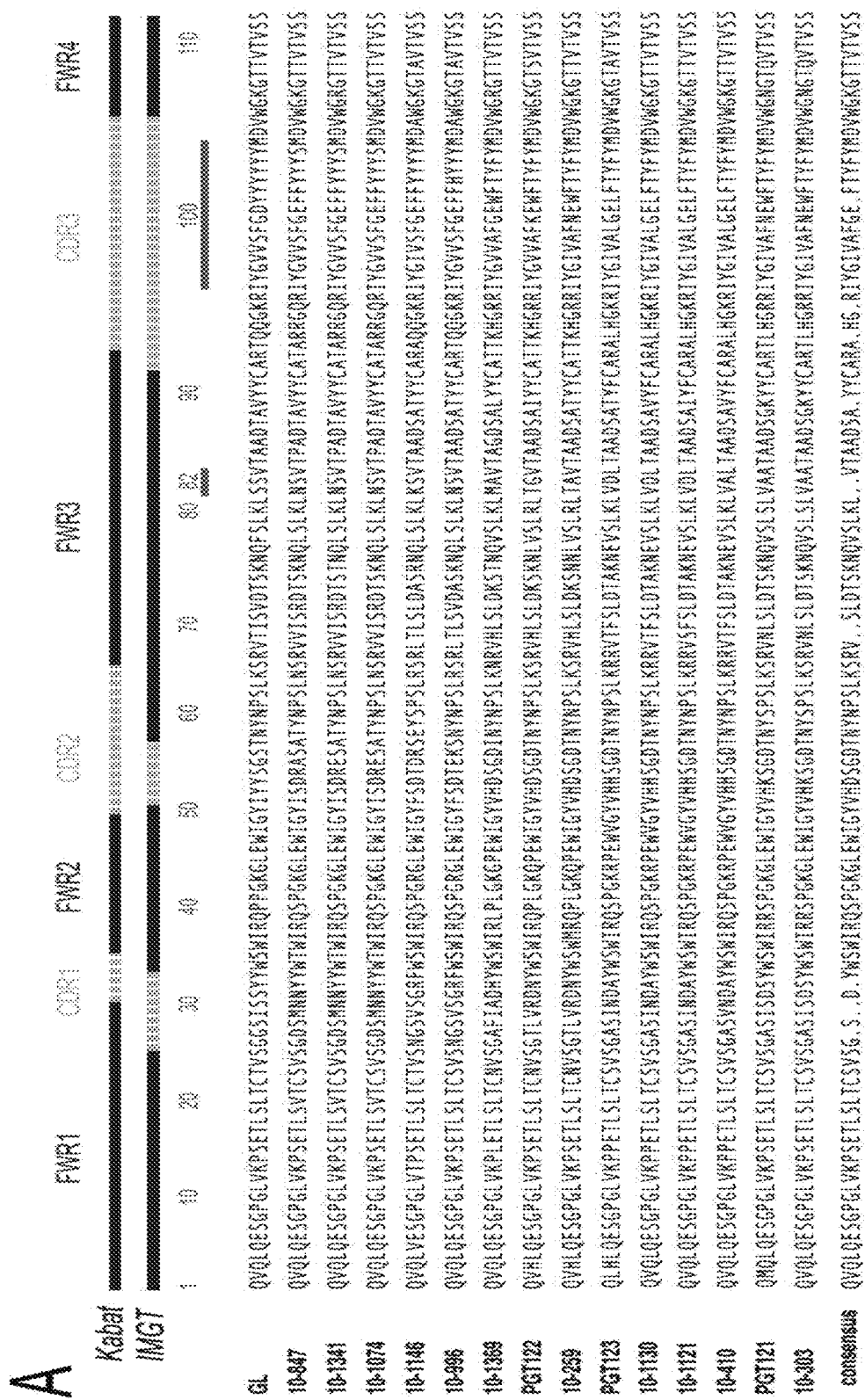
FIGS. 3A and 3B depict: Sequence alignments of PGT121 and 10-1074 clonal variants. (A) Amino acid alignment of the heavy chains (IgH) of the PGT121-like and 10-1074-like antibodies, and the likely germline (GL) VH for all clonal variants. Amino acid numbering based on crystal structures, framework (FWR) and complementary determining regions (CDR) as defined by Kabat (. J Exp Med 132(2):211-250) and IMGT (Nucleic Acids Res 37 (Database issue): D1006-1012) are indicated. Color shading shows acidic (red), basic (blue), and tyrosine (green) amino acids. (B) Same as A but for the light chains (IgL).
Figure 3B:
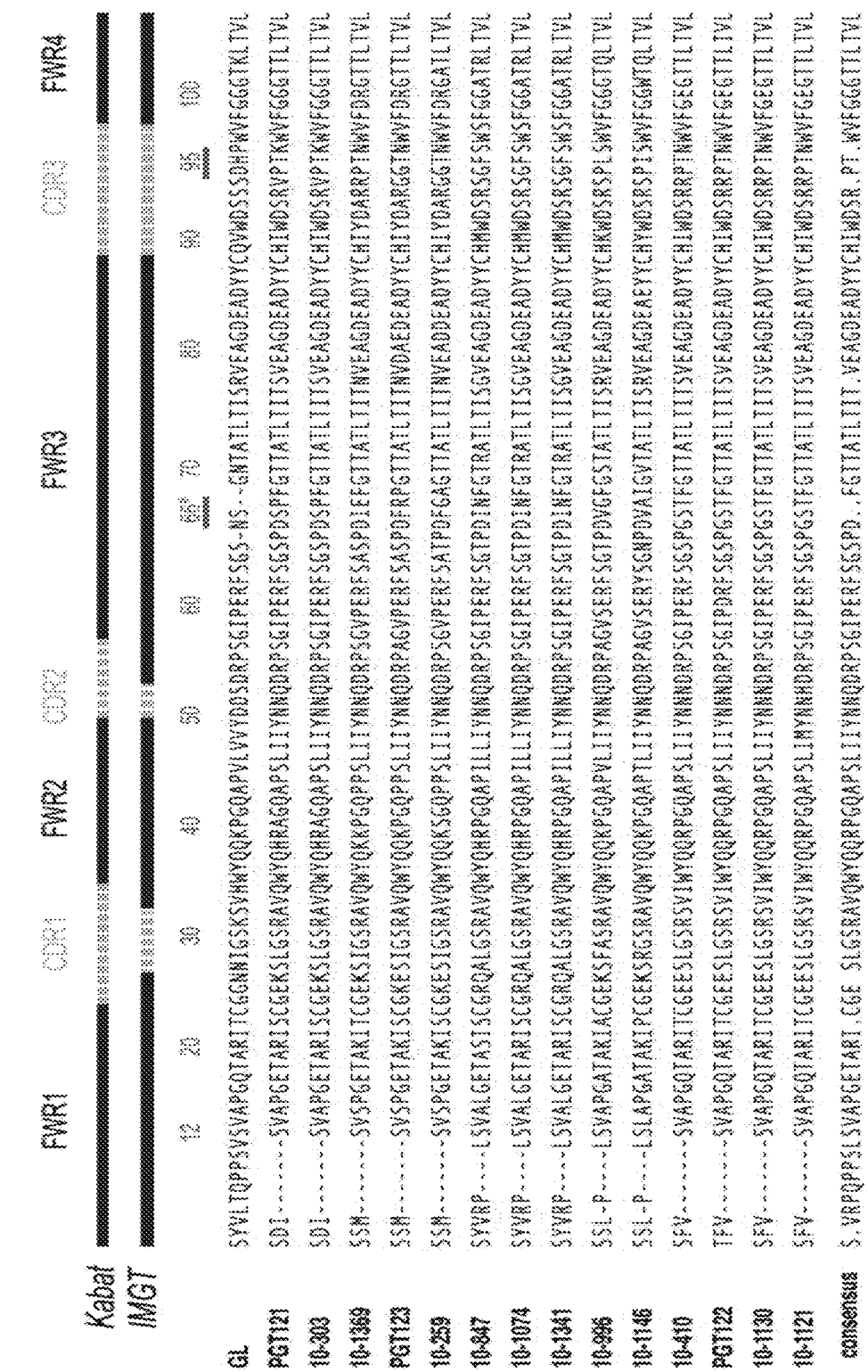

The sequence alignments of three PGT antibodies (PGT-121, -122, and -123), eleven PGT121 and 10-1074 clonal variants (10-259, 10-303, 10-410, 10-847, 10-996, 10-1074, 10-1121, 10-1130, 10-1146, 10-1341, 10-1369, and 10-1074GM,), likely germline (GL), and consensus sequences are shown in FIGS. 3(a) and 3(b). The sequences for corresponding heavy chain variable regions, light chain variable regions, heavy chain CDRs, and light chain CDRs under both IMGT and KABT systems are listed in Table 1 below. Assigned sequence identification numbers for the sequences under the KABT systems are listed in Table 2 below:

TABLE 1

| IMGT | FWR1 | CDR1 | FWR2 | CDR2 | FWR3 | CDR3 | FWR4 |
|---|---|---|---|---|---|---|---|
| 10-1369 (SEQ ID NO: 23) | QVQLQESGPGLVKPLETLSLTCN VS | GAFIADHY (SEQ ID NO: 139) | WSWIRLPLGKG PEWIGY | VHDSGDI (SEQ ID NO: 140) | NYNPSLKNRVHLSLDKSTNQVSLKLM AVTAGDSALYYC | ATTKHGRRIYGVVAFGE WFTYFYMDV (SEQ ID NO: 141) | WGRGTTVTVSS |
| 10-259 (SEQ ID NO: 3) | QVHLQESGPGLVKPSETLSLTCN VS | GTLVRDNY (SEQ ID NO: 142) | WSWMRQPLGKQ PEWIGY | VHDSGDT (SEQ ID NO: 143) | NYNPSLKSRVHLSLDKSNNLVSLRLT AVTAADSATYYC | ATTKHGRRIYGIVAFNE WFTYFYMDV (SEQ ID NO: 144) | WGKGTTVTVSS |
| 10-303 (SEQ ID NO: 5) | QVQLQESGPGLVKPSETLSLTCS VS | GASISDSY (SEQ ID NO: 145) | WSWIRRSPGKG LEWIGY | VHKSGDT (SEQ ID NO: 146) | NYSPSLKSRVNLSLDTSKNQVSLSLV AATAADSGKYYC | ARTLHGRRIYGIVAFNE WFTYFYMDV (SEQ ID NO: 147) | WGNGTQVTVSS |
| 10-410 (SEQ ID NO: 7) | QVQLQESGPGLVKPPETLSLTCS VS | GASVNDAY (SEQ ID NO: 148) | WSWIRQSPGKR PEWVGY | VHHSGDT (SEQ ID NO: 149) | NYNPSLKRRVTFSLDTAKNEVSLKLV ALTAADSAVYFC | ARALHGKRIYGIVALGE LFTYFYMDV (SEQ ID NO: 150) | WGKGTTVTVSS |
| 10-1130 (SEQ ID NO: 17) | QVQLQESGPGLVKPPETLSLTCS VS | GASINDAY (SEQ ID NO: 151) | WSWIRQSPGKR PEWVGY | VHHSGDT (SEQ ID NO: 152) | NYNPSLKRRVTFSLDTAKNEVSLKLV DLTAADSAVYFC | ARALHGKRIYGIVALGE LFTYFYMDV (SEQ ID NO: 153) | WGKGTTVTVSS |
| 10-1121 (SEQ ID NO: 15) | QVQLQESGPGLVKPPETLSLTCS VS | GASINDAY (SEQ ID NO: 154) | WSWIRQSPGKR PEWVGY | VHHSGDT (SEQ ID NO: 155) | NYNPSLKRRVSFSLDTAKNEVSLKLV DLTAADSAIYFC | ARALHGKRIYGIVALGE LFTYFYMDV (SEQ ID NO: 156) | WGKGTTVTVSS |
| 10-1146 (SEQ ID NO: 19) | QVQLVESGPGLVTPSETLSLTCT VS | NGSVSGRF (SEQ ID NO: 157) | WSWIRQSPGRG LEWIGY | FSDTDRS (SEQ ID NO: 158) | EYSPSLRSRLTLSLDASRNQLSLKLK SVTAADSATYYC | ARAQQGKRIYGIVSFGE FFYYYMDA (SEQ ID NO: 159) | WGKGTAVTVSS |
| 10-996 (SEQ ID NO: 11) | QVQLQESGPGLVKPSETLSLTCS VS | NGSVSGRF (SEQ ID NO: 160) | WSWIRQSPGRG LEWIGY | FSDTEKS (SEQ ID NO: 161) | NYNPSLRSRLTLSVDASKNQLSLKLN SVTAADSATYYC | ARTQQGKRIYGVVSFGE FFHYYMDA (SEQ ID NO: 162) | WGKGTAVTVSS |
| 10-847 GL (SEQ ID NO: 31) | QVQLQESGPGLVKPSETLSLTCT VS | GGSISSYY (SEQ ID NO: 163) | WSWIRQPPGKG LEWIGY | IYYSGST (SEQ ID NO: 164) | NYNPSLKSRVTISVDTSKNQFSLKLS SVTPADTAVYYC | ARTQQGKRIYGVVSFGD YYYYYMDV (SEQ ID NO: 165) | WGKGTTVTVSS |
| 10-1341 (SEQ ID NO: 21) | QVQLQESGPGLVKPSETLSVTCS VS | GDSMNNYY (SEQ ID NO: 166) | WTWIRQSPGKG LEWIGY | ISDRESA (SEQ ID NO: 167) | TYNPSLNSRVVISRDTSTNQLSLKLN SVTPADTAVYYC | ATARRGQRIYGVVSFGE FFYYYSMDV (SEQ ID NO: 168) | WGRGTTVTVSS |
| 10-847 (SEQ ID NO: 9) | QVQLQESGPGLVKPSETLSVTCS VS | GDSMNNYY (SEQ ID NO: 169) | WTWIRQSPGKG LEWIGY | ISDRASA (SEQ ID NO: 170) | TYNPSLNSRVVISRDTSKNQLSLKLN SVTPADTAVYYC | ATARRGQRIYGVVSFGE FFYYYSMDV (SEQ ID NO: 171) | WGKGTTVTVSS |
| 10-1074 (SEQ ID NO: 13) | QVQLQESGPGLVKPSETLSVTCS VS | GDSMNNYY (SEQ ID NO: 172) | WTWIRQSPGKG LEWIGY | ISDRESA (SEQ ID NO: 173) | TYNPSLNSRVVISRDTSKNQLSLKLN SVTPADTAVYYC | ATARRGQRIYGVVSFGE FFYYYSMDV (SEQ ID NO: 174) | WGKGTTVTVSS |
| 10-1074GM (SEQ ID NO: 129) | QVQLQESGPGLVKPSETLSVTCS VS | GDSMNNSY (SEQ ID NO: 175) | WTWIRQSPGKG LEWIGY | ISKSESA (SEQ ID NO: 176) | NYNPSLNSRVVISRDTSKNQLSLKLN SVTPADTAVYYC | ATARHGQRIYGVVSFGE FFTYYSMDV (SEQ ID NO: 177) | WGKGTTVTVSS |

TABLE 1-continued

| KABAT | FWR1 | CDR1 | FWR2 | CDR2 | FWR3 | CDR3 | FWR4 |
|---|---|---|---|---|---|---|---|
| 10-1369 (SEQ ID NO: 23) | QVQLQESGPGLVKPLETLSLTCN VSGAFIA | DHYWS (SEQ ID NO: 99) | WIRLPLGKGPE WIG | YVHDSGDINY NPSLKN (SEQ ID NO: 100) | RVHLSLDKSTNQVSLKKLMAVTAGDSA LYYCAT | TKHGRRIYGVVAFGEWF TYFYMDV (SEQ ID NO: 101) | WGRGTTVTVSS |
| 10-259 (SEQ ID NO: 3) | QVHLQESGPGLVKPSETLSLTCN VSGTLVR | DNYWS (SEQ ID NO: 39) | WMRQPLGKQPE WIG | YVHDSGDTNY NPSLKS (SEQ ID NO: 40) | RVHLSLDKSNNLVSLRLTAVTAADSA TYYCAT | TKHGRRIYGIVAFNEWF TYFYMDV (SEQ ID NO: 41) | WGKGTTVTVSS |
| 10-303 (SEQ ID NO: 5) | QVQLQESGPGLVKPSETLSLTCS VSGASIS | DSYWS (SEQ ID NO: 45) | WIRRSPGKGLE WIG | YVHKSGDTNY SPSLKS (SEQ ID NO: 46) | RVNLSLDTSKNQVSLSLVAATAADSG KYYCAR | TLHGRRIYGIVAFNEWF TYFYMDV (SEQ ID NO: 47) | WGNGTQVTVSS |
| 10-410 (SEQ ID NO: 7) | QVQLQESGPGLVKPPETLSLTCS VSGASVN | DAYWS (SEQ ID NO: 51) | WIRQSPGKRPE WVG | YVHHSGDTNY NPSLKR (SEQ ID NO: 52) | RVTFSLDTAKNEVSLKLVALTAADSA VYFCAR | ALHGKRIYGIVALGELF TYFYMDV (SEQ ID NO: 53) | WGKGTTVTVSS |
| 10-1130 (SEQ ID NO: 17) | QVQLQESGPGLVKPPETLSLTCS VSGASIN | DAYWS (SEQ ID NO: 81) | WIRQSPGKRPE WVG | YVHHSGDTNY NPSLKR (SEQ ID NO: 82) | RVTFSLDTAKNEVSLKLVDLTAADSA VYFCAR | ALHGKRIYGIVALGELF TYFYMDV (SEQ ID NO: 83) | WGKGTTVTVSS |
| 10-1121 (SEQ ID NO: 15) | QVQLQESGPGLVKPPETLSLTCS VSGASIN | DAYWS (SEQ ID NO: 75) | WIRQSPGKRPE WVG | YVHHSGDTNY NPSLKR (SEQ ID NO: 76) | RVSFSLDTAKNEVSLKLVDLTAADSA IYFCAR | ALHGKRIYGIVALGELF TYFYMDV (SEQ ID NO: 77) | WGKGTTVTVSS |
| 10-1146 (SEQ ID NO: 19) | QVQLVESGPGLVTPSETLSLTCT VSNGVVS | GRFWS (SEQ ID NO: 87) | WIRQSPGRGLE WIG | YFSDTDRSEY SPSLRS (SEQ ID NO: 88) | RLTLSLDASRNQLSLKLKSVTAADSA TYYCAR | AQQGKRIYGIVSFGEFF YYYMDV (SEQ ID NO: 89) | WGKGTAVTVSS |
| 10-996 (SEQ ID NO: 11) | QVQLVESGPGLVKPSETLSLTCS VSNGVVS | GRFWS (SEQ ID NO: 63) | WIRQSPGRGLE WIG | YFSDTEKSNY NPSLRS (SEQ ID NO: 64) | RLTLSVDASKNQLSLKLNSVTAADSA TYYCAR | TQQGKRIYGVVSFGEFF HYYYMDA (SEQ ID NO: 65) | WGKGTAVTVSS |
| GL (SEQ ID NO: 31) | QVQLQESGPGLVKPSETLSLTCT VSGGSIS | SYYWS (SEQ ID NO: 123) | WIRQPPGKGLE WIG | YIYYSGSTNY NPSLKS (SEQ ID NO: 124) | RVTISVDTSKNQPSLKLSSVTAADTA VYYCAR | TQQGKRIYGVVSFGDYY YYYYMDV (SEQ ID NO: 125) | WGKGTTVTVSS |
| 10-1341 (SEQ ID NO: 21) | QVQLQESGPGLVKPSETLSVTCS VSGDSMN | NYYWT (SEQ ID NO: 93) | WIRQSPGKGLE WIG | YISDRESATY NPSLNS (SEQ ID NO: 94) | RVVISRDTSTNQLSLKLNSVTPADTA VYYCAR | ARRGQRIYGVVSFGEFF YYYSMDV (SEQ ID NO: 95) | WGKGTTVTVSS |
| 10-847 (SEQ ID NO: 9) | QVQLQESGPGLVKPSETLSVTCS VSGDSMN | NYYWT (SEQ ID NO: 57) | WIRQSPGKGLE WIG | YISDRASATY NPSLNS (SEQ ID NO: 58) | RVVISRDTSKNQLSLKLNSVTPADTA VYYCAT | ARRGQRIYGVVSFGEFF YYYSMDV (SEQ ID NO: 59) | WGKGTTVTVSS |
| 10-1074 (SEQ ID NO: 13) | QVQLQESGPGLVKPSETLSVTCS VSGDSMN | NYYWT (SEQ ID NO: 69) | WIRQSPGKGLE WIG | YISDRESATY NPSLNS (SEQ ID NO: 70) | RVVISRDTSKNQLSLKLNSVTPADTA VYYCAT | ARRGQRIYGVVSFGEFF YYYSMDV (SEQ ID NO: 71) | WGKGTTVTVSS |

TABLE 1-continued

IgL SEQUENCES

| IMGT | FWR1 | CDR1 | FWR2 | CDR2 | FWR3 | CDR3 | FWR4 |
|---|---|---|---|---|---|---|---|
| 10-1074GM GL (SEQ ID NO: 32) | SYVLTQPPSVSAPGQTARITCG GN | NIGSKS (SEQ ID NO: 178) | VHWYQQKPGQA PVLVVY | DDS (SEQ ID NO: 179) | DRPSGIPERFSGSNSGNTATLTISRV EAGDEADYYC | QVWDSSDHPWV (SEQ ID NO: 180) | FGGGTKLTVL |
| 10-1369 (SEQ ID NO: 24) | SSMSVSPGETAKITCGEK | SIGSRA (SEQ ID NO: 181) | VQWYQKKPGQP PSLIIY | NNQ (SEQ ID NO: 182) | DRPSGVPERFSASPDIEFGTTATLTI TNVEAGDEADYYC | HIYDARRPTNWV (SEQ ID NO: 183) | FDRGTILTVL |
| 10-259 (SEQ ID NO: 4) | SSMSVSPGETAKISCGKE | SIGSRA (SEQ ID NO: 184) | VQWYQQKSGQP PSLIIY | NNQ (SEQ ID NO: 185) | DRPSGVPERFSATPDFGAGITAILTI TNVEADDEADYYC | HIYDARGGTNWV (SEQ ID NO: 186) | FDRGATLIVL |
| 10-303 (SEQ ID NO: 6) | SDISVAPGETARISCGEK | SLGSRA (SEQ ID NO: 187) | VQWYQHRAGQA PSLIIY | NNQ (SEQ ID NO: 188) | DRPSGIPERFSGSPDSPPGTTATLTI TSVEAGDEADYYC | HIWDSRVPIKWV (SEQ ID NO: 189) | FGGGTLTVL |
| 10-1121 (SEQ ID NO: 16) | SFVSVAPGQTARITCGEE | SLGSRS (SEQ ID NO: 190) | VIWYQQRPGQA PSLIMY | NNH (SEQ ID NO: 191) | DRPSGIPERFSGSPGSTFGTTATLTI TSVEAGDEADYYC | HIWDSRRPINWV (SEQ ID NO: 192) | FGEGTLTVL |
| 10-410 (SEQ ID NO: 8) | SFVSVAPGQTARITCGEE | SLGSRS (SEQ ID NO: 193) | VIWYQQRPGQA PSLIIY | NNN (SEQ ID NO: 194) | DRPSGIPERFSGSPGSTFGTTATLTI TSVEAGDEADYYC | HIWDSRRPINWV (SEQ ID NO: 195) | FGEGTTLTVL |
| 10-1130 (SEQ ID NO: 18) | SFVSVAPGQTARITCGEE | SLGSRA (SEQ ID NO: 196) | VIWYQQRPGQA PSLIIY | NNN (SEQ ID NO: 197) | DRPSGIPERFSGSPGSTFGTTATLTI TSVEAGDEADYYC | HIWDSRRPINWV (SEQ ID NO: 198) | FGEGTLTVL |
| 10-847 (SEQ ID NO: 10) | SYVRPLSVALGETASISCGRQ | ALGSRA (SEQ ID NO: 199) | VQWYQHRPGQA PILLIY | NNQ (SEQ ID NO: 200) | DRPSGIPERFSGTPDINFGTRATLTI SGVEAGDEADYYC | HMWDSRSGFSWS (SEQ ID NO: 201) | FGGATRLTVL |
| 10-1074 (SEQ ID NO: 14) | SYVRPLSVALGETARISCGRQ | ALGSRA (SEQ ID NO: 202) | VQWYQHRPGQA PILLIY | NNQ (SEQ ID NO: 203) | DRPSGIPERFSGTPDINFGTRATLTI SGVEAGDEADYYC | HMWDSRSGFSWS (SEQ ID NO: 204) | FGGATRLTVL |
| 10-1341 (SEQ ID NO: 22) | SYVRPLSVALGETARISCGRQ | ALGSRA (SEQ ID NO: 205) | VQWYQHRPGQA PILLIY | NNQ (SEQ ID NO: 206) | DRPSGIPERFSGTPDINFGTRATLTI SGVEAGDEADYYC | HMWDSRSGFSWS (SEQ ID NO: 207) | FGGATRLTVL |
| 10-996 (SEQ ID NO: 12) | SSLPLSVAPGATAKIACGEK | SFASRA (SEQ ID NO: 208) | VQWYQQKPGQA PVLIIY | NNQ (SEQ ID NO: 209) | DRPAGVSERFSGTPDVGFGSTATLTI SRVEAGDEADYYC | HKWDSRSPLSWV (SEQ ID NO: 210) | FGGGTQLTVL |
| 10-1146 (SEQ ID NO: 20) | SSLPLSLAPGATAKIPCGEK | SRGSRA (SEQ ID NO: 211) | VQWYQQKPGQA PTLIIY | NNQ (SEQ ID NO: 212) | DRPAGVSERYSGNPDVAIGVTATLTI SRVEAGDEAEYYC | HYWDSRSPISWV (SEQ ID NO: 213) | FGGWTQLTVL |

TABLE 1-continued

| KABAT | FWR1 | CDR1 | FWR2 | CDR2 | FWR3 | CDR3 | FWR4 |
|---|---|---|---|---|---|---|---|
| GL (SEQ ID NO: 32) | SYVLTQPPSVSVAPGQTARITC | GGNNIGSKSVH (SEQ ID NO: 126) | WYQQKPGQAPV LVVY | DDSDRPS (SEQ ID NO: 127) | GIPERFSGSNSGNTATLTISRVEAGD EADYYC | QVWDSSDHPWV (SEQ ID NO: 128) | FGGGTKLTVL |
| 10-1369 (SEQ ID NO: 24) | SSMSVSPGETAKITC | GEKSIGSRAVQ (SEQ ID NO: 102) | WYQKKPGQPPS LIIY | NNQDRPS (SEQ ID NO: 103) | GVPERFSASPDIEFGTTATLTITNVE AGDEADYYC | HIYDARRPTNWV (SEQ ID NO: 104) | FDRGTILTVL |
| 10-259 (SEQ ID NO: 4) | SSMSVSPGETAKISC | GKESIGSRAVQ (SEQ ID NO: 42) | WYQQKSGQPPS LIIY | NNQDRPS (SEQ ID NO: 43) | GVPERFSATPDFGAGITAILTITNVE ADDEADYYC | HIYDARGGTNWV (SEQ ID NO: 44) | FDRGATLIVL |
| 10-303 (SEQ ID NO: 6) | SDISVAPGETARISC | GEKSLGSRAVQ (SEQ ID NO: 48) | WYQHRAGQAPS LIIY | NNHDRPS (SEQ ID NO: 49) | GIPERFSGSPDSPFGTTATLTITSVE AGDEADYYC | HIWDSRVPIKWV (SEQ ID NO: 50) | FGGGTTLTVL |
| 10-1121 (SEQ ID NO: 16) | SFVSVAPGQTARITC | GEESLGSRSVI (SEQ ID NO: 78) | WYQQRPGQAPS LIMY | NNHDRPS (SEQ ID NO: 79) | GIPERFSGSPGSTFGTTATLTITSVE AGDEADYYC | HIWDSRRPINWV (SEQ ID NO: 80) | FGEGTTLTVL |
| 10-410 (SEQ ID NO: 8) | SFVSVAPGQTARITC | GEESLGSRSVI (SEQ ID NO: 54) | WYQQRPGQAPS LIIY | NNNDRPS (SEQ ID NO: 55) | GIPERFSGSPGSTFGTTATLTITSVE AGDEADYYC | HIWDSRRPINWV (SEQ ID NO: 56) | FGEGTTLTVL |
| 10-1130 (SEQ ID NO: 10) | SFVSVAPGQTARITC | GEESLGSRSVI (SEQ ID NO: 84) | WYQQRPGQAPS LIIY | NNNDRPS (SEQ ID NO: 85) | GIPERFSGSPGSTFGTTATLTITSVE AGDEADYYC | HIWDSRRPINWV (SEQ ID NO: 86) | FGEGTTLTVL |
| 10-847 (SEQ ID NO: 10) | SYVRPLSVALGETASISC | GRQALGSRAVQ (SEQ ID NO: 60) | WYQHRPGQAPI LLIY | NNQDRPS (SEQ ID NO: 61) | GIPERFSGTPDINFGTRATLTISGVE AGDEADYYC | HMWDSRSGFSWS (SEQ ID NO: 62) | FGGATRLTVL |
| 10-1074 (SEQ ID NO: 14) | SYVRPLSVALGETARISC | GRQALGSRAVQ (SEQ ID NO: 72) | WYQHRPGQAPI LLIY | NNQDRPS (SEQ ID NO: 73) | GIPERFSGTPDINFGTRATLTISGVE AGDEADYYC | HMWDSRSGFSWS (SEQ ID NO: 74) | FGGATRLTVL |
| 10-1341 (SEQ ID NO: 22) | SYVRPLSVALGETARISC | GRQALGSRAVQ (SEQ ID NO: 96) | WYQHRPGQAPI LLIY | NNQDRPS (SEQ ID NO: 97) | GIPERFSGTPDINFGTRATLTISGVE AGDEADYYC | HMWDSRSGFSWS (SEQ ID NO: 98) | FGGATRLTVL |
| 10-996 (SEQ ID NO: 12) | SSLPLSVAPGATAKIAC | GEKSFASRAVQ (SEQ ID NO: 66) | WYQQKPGQAPV LIIY | NNQDRPA (SEQ ID NO: 67) | GVSERFSGTPDVGFGSTATLTISRVE AGDEADYYC | HKWDSRSPLSWV (SEQ ID NO: 68) | FGGGTQLTVL |
| 10-1146 (SEQ ID NO: 20) | SSLPLSLAPGATAKIPC | GEKSRGSRAVQ (SEQ ID NO: 90) | WYQQKPGQAPT LIIY | NNQDRPA (SEQ ID NO: 91) | GVSERYSGNPDVAIGVTATLTISRVE AGDEAEYYC | HYWDSRSPISWV (SEQ ID NO: 92) | FGGWTQLTVL |

TABLE 2

| | SEQ ID NOs | | | |
|---|---|---|---|---|
| | Variable Region | | CDRs 1-3 | |
| Name | Heavy chain (H) | Light chain (L) | H | L |
| consensus | SEQ ID NO: 1 | SEQ ID NO: 2 | SEQ ID NOs: 33-35 | SEQ ID NOs: 36-38 |
| 10-259 | SEQ ID NO: 3 | SEQ ID NO: 4 | SEQ ID NOs: 39-41 | SEQ ID NOs: 42-44 |
| 10-303 | SEQ ID NO: 5 | SEQ ID NO: 6 | SEQ ID NOs: 45-47 | SEQ ID NOs: 48-50 |
| 10-410 | SEQ ID NO: 7 | SEQ ID NO: 8 | SEQ ID NOs: 51-53 | SEQ ID NOs: 54-56 |
| 10-847 | SEQ ID NO: 9 | SEQ ID NO: 10 | SEQ ID NOs: 57-59 | SEQ ID NOs: 60-62 |
| 10-996 | SEQ ID NO: 11 | SEQ ID NO: 12 | SEQ ID NOs: 63-65 | SEQ ID NOs: 66-68 |
| 10-1074 | SEQ ID NO: 13 | SEQ ID NO: 14 | SEQ ID NOs: 69-71 | SEQ ID NOs: 72-74 |
| 10-1121 | SEQ ID NO: 15 | SEQ ID NO: 16 | SEQ ID NOs: 75-77 | SEQ ID NOs: 78-80 |
| 10-1130 | SEQ ID NO: 17 | SEQ ID NO: 18 | SEQ ID NOs: 81-83 | SEQ ID NOs: 84-86 |
| 10-1146 | SEQ ID NO: 19 | SEQ ID NO: 20 | SEQ ID NOs: 87-89 | SEQ ID NOs: 90-92 |
| 10-1341 | SEQ ID NO: 21 | SEQ ID NO: 22 | SEQ ID NOs: 93-95 | SEQ ID NOs: 96-98 |
| 10-1369 | SEQ ID NO: 23 | SEQ ID NO: 24 | SEQ ID NOs: 99-101 | SEQ ID NOs: 102-104 |
| PGT-121 | SEQ ID NO: 25 | SEQ ID NO: 26 | SEQ ID NOs: 105-107 | SEQ ID NOs: 108-110 |
| PGT-122 | SEQ ID NO: 27 | SEQ ID NO: 28 | SEQ ID NOs: 111-113 | SEQ ID NOs: 114-116 |
| PGT-123 | SEQ ID NO: 29 | SEQ ID NO: 30 | SEQ ID NOs: 117-119 | SEQ ID NOs: 120-122 |
| GL | SEQ ID NO: 31 | SEQ ID NO: 32 | SEQ ID NOs: 123-125 | SEQ ID NOs: 126-128 |
| 10-1074GM | SEQ ID NO: 129 | SEQ ID NO: 130 | SEQ ID NOs: 131-133 | SEQ ID NOs: 134-136 |

Eleven new unique variants were expressed (Table 3) and demonstrated binding to YU-2 gp120 and gp140 by ELISA and surface plasmon resonance (SPR). Unless otherwise noted, the gp120 and gp140 proteins for these and other experiments were expressed in mammalian cells that can attach either a complex-type or a high-mannose N-glycan to a PNGS. The level of reactivity with gp120 differed between antibodies belonging to the PGT121 and 10-1074 groups, the latter exhibiting higher apparent affinities (FIG. 3A) mainly due to slower dissociation from gp120/gp140 for the 10-1074-related antibodies (FIG. 4B).

EXAMPLE 3

Figure 5A:
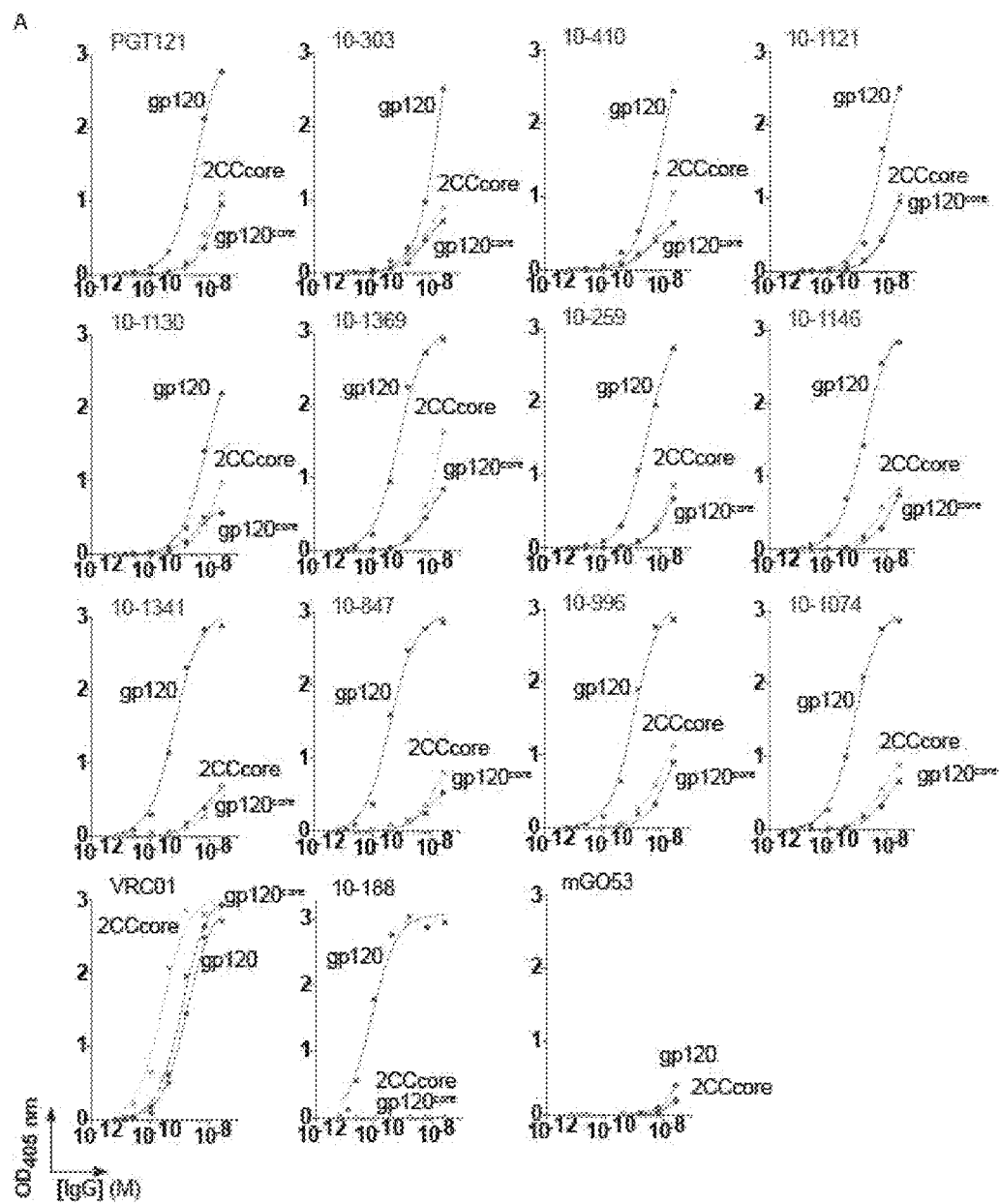
FIGS. 5A, 5B and 5C depict: Binding of PGT121 variants to gp120 "core" proteins, gp120$^{GD324-5AA}$ mutant and linear gp120$^{V3}$ peptides. (A) ELISA-based binding analyses of PGT121-like and 10-1074-like antibodies to HXB2 gp120$^{core}$ and 2CC-core proteins compared to intact YU-2 gp120. The x axis shows the antibody concentration (M) required to obtain the ELISA values ($OD_{405}$ nm) indicated on the y axis. The anti-CD4bs antibody VRC01 (Science 329(5993):856-861), the anti-V3 loop antibody 10-188 (PLoS One 6(9): e24078), and the non HIV-reactive antibody mGO53 (Science 301(5638):1374-1377) were used as controls. (B) Same as (A) but for binding to gp120$^{GD324-5AA}$ mutant protein (c) Bar graphs comparing the ELISA reactivities of the PGT121- and 10-1074-like antibodies and control antibodies (positive control, 10-188, 1-79, 2-59 and 2-1261 (Nature 458(7238):636-640)), and negative control, mGO53) against gp120$^{V3-C3}$ overlapping peptides. The y axis indicates the ELISA values ($OD_{405\ nm}$) obtained by testing the IgG antibodies at 2 μg/ml. The amino acid sequences of individual peptides are shown in the bottom right. All experiments were performed at least in duplicate. Representative data are shown.
Figure 5B:
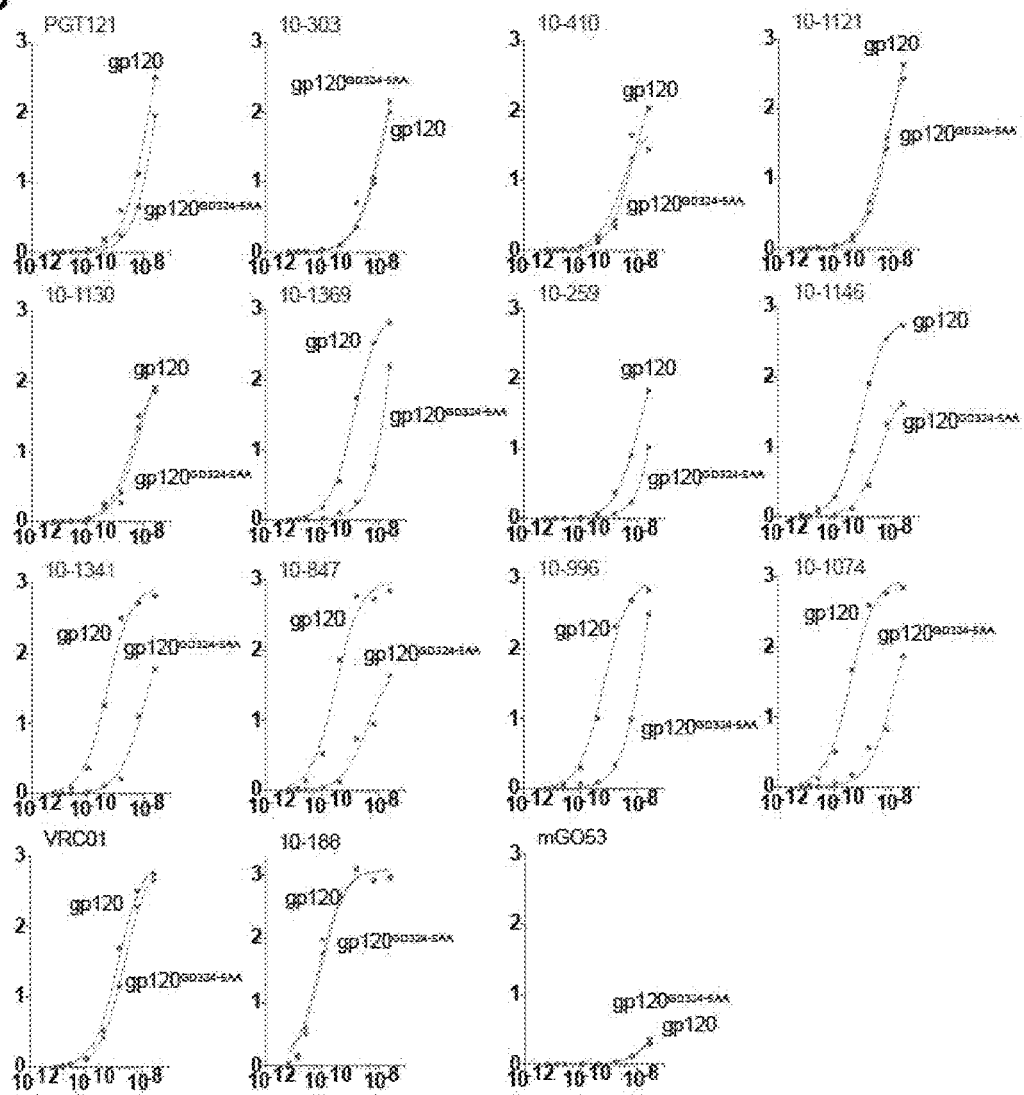
Figure 5C:
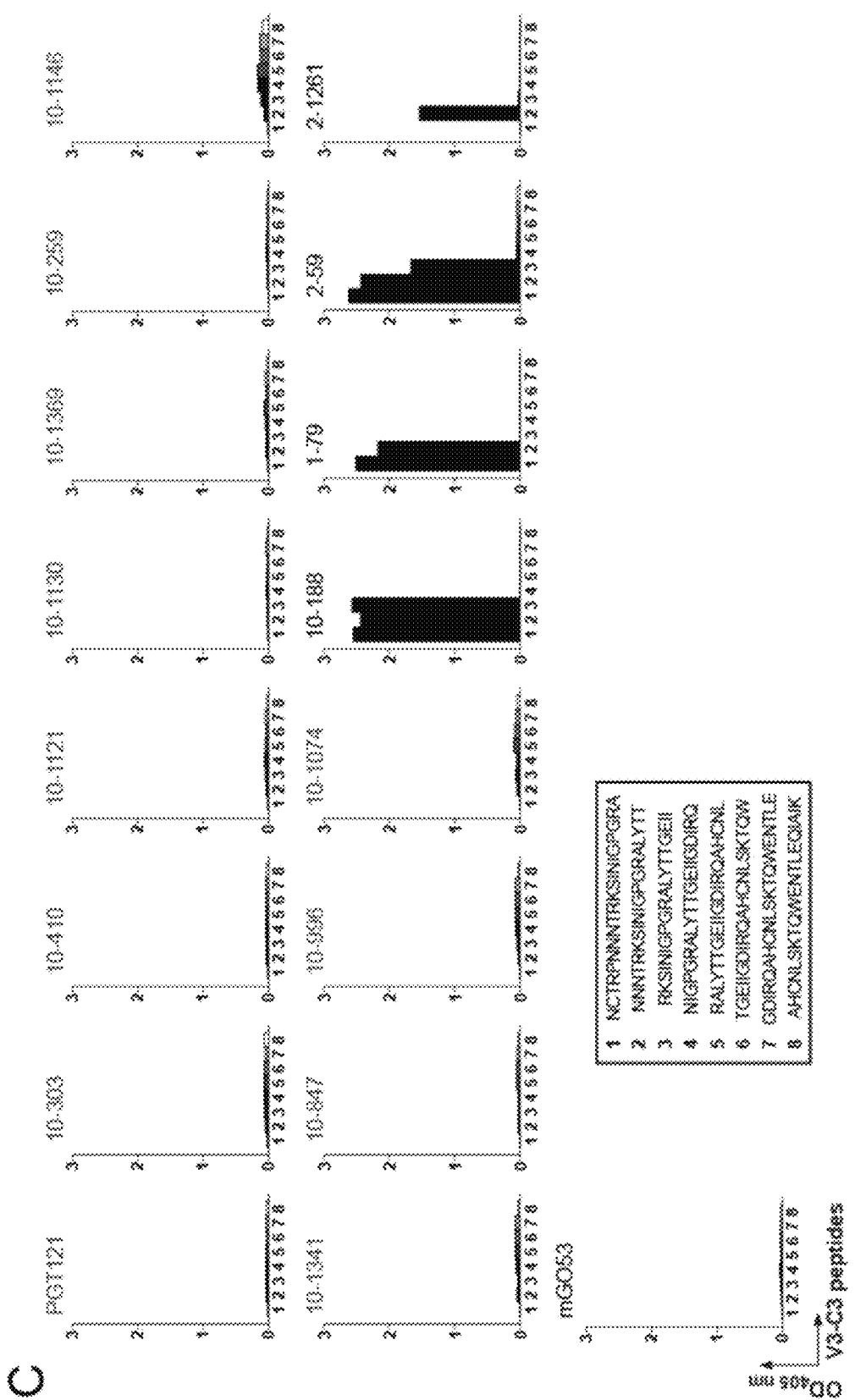

PGT121 and 10-1074 Epitopes $Asn332_{gp120}$ in the vicinity of the V3 loop stem was reported as critical for binding and viral neutralization by PGT121 (Nature 477(7365):466-470), thus we examined the role of V3 in antigen recognition by PGT121-like and 10-1074-like antibodies. ELISAs were performed using HXB2 gp120 "core" proteins that lack V1-V3 loops ($gp120^{core}$) or retain a portion of V3 (2CC-core), and using a YU-2 gp120 mutant protein carrying a double alanine substitution in the V3 stem ($gp120^{GD324-5AA}$). The tested antibodies showed decreased reactivity against variants lacking the V3 loop and $gp120^{GD324-5AA}$ when compared to intact YU-2 gp120, with the binding of 10-1074-group antibodies being the most affected (FIGS. 5A and B). These results suggest that recognition by both antibody groups involves protein determinants in the vicinity of the V3 loop. None of the antibodies bound to overlapping peptides spanning V3, suggesting the targeted epitopes are discontinuous and/or require a particular conformation not achieved by isolated peptides (FIG. 5C).

$Asn332_{gp120}$ ($Asn337_{gp120}$ in earlier numbering (J Proteome Res 7(4):1660-1674)) is the N-terminal residue of a potential N-glycosylation site (PNGS) defined as the sequence Asn-X-Ser/Thr. To determine whether $Asn332_{gp120}$ and/or its N-linked glycan are required for gp120 reactivity of the new PGT121- and 10-1074-group antibodies, we tested their binding to YU-2 $gp120^{N332A}$ by ELISA. The N332A substitution diminished the binding of PGT121 and all the new antibody variants, whereas their reactivity against a mutant gp120 lacking a nearby glycosylation site ($gp120^{NNT301-3AAA}$ mutant) was unchanged. To determine if a PNGS in addition to the $Asn332_{gp120}$ PNGS affects recognition by the new antibodies, we constructed a series of 11 double glycan mutants in which the N332A mutation in YU-2 gp120 was combined with mutation of PNGSs located between $Asn262_{gp120}$ and $Asn406_{gp120}$. All of the PGT121-like and 10-1074-like antibodies bound to each of the double glycan mutants with comparable affinity as to that for $gp120^{N332A}$.

Figure 6A:
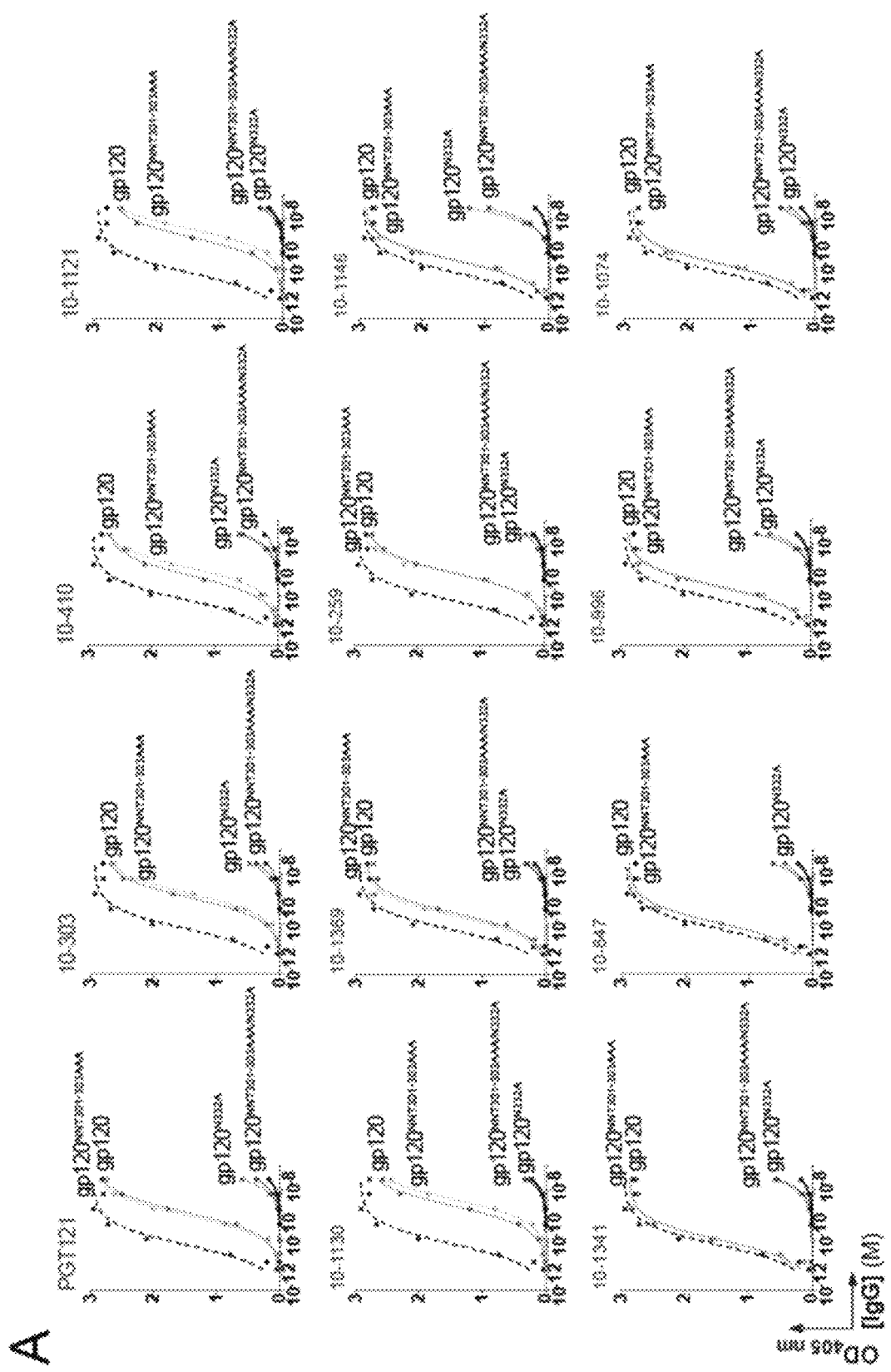
FIGS. 6A, 6B, 6C and 6D depict: Binding of PGT121 to gp120 glycosylation mutants and deglycosylated gp120. (A) ELISA-based binding analyses of PGT121 and 10-1074 antibody variants to gp120, gp120$^{NNT301-303AAA}$, gp120$^{N332A}$ and gp120$^{N332A/NNT301-303AAA}$. The x axis shows the antibody concentration (M) required to obtain the ELISA values ($OD_{405}$ nm) indicated on the y axis. The black dashed and continuous lines show the averaged reactivity against the four antigens of positive (10-188) and negative (mGO53) antibody controls. (B) Silver-stained SDS-PAGE gel comparing untreated gp120 (WT, wild type), PNGase F- and EndoH-digested gp120s. L, protein ladder. (C), Same as (A) but comparing untreated and PNGase F-treated gp120. (D) Same as (A) but comparing untreated and EndoH-treated gp120. All experiments were performed at least in duplicate.
Figure 6B:
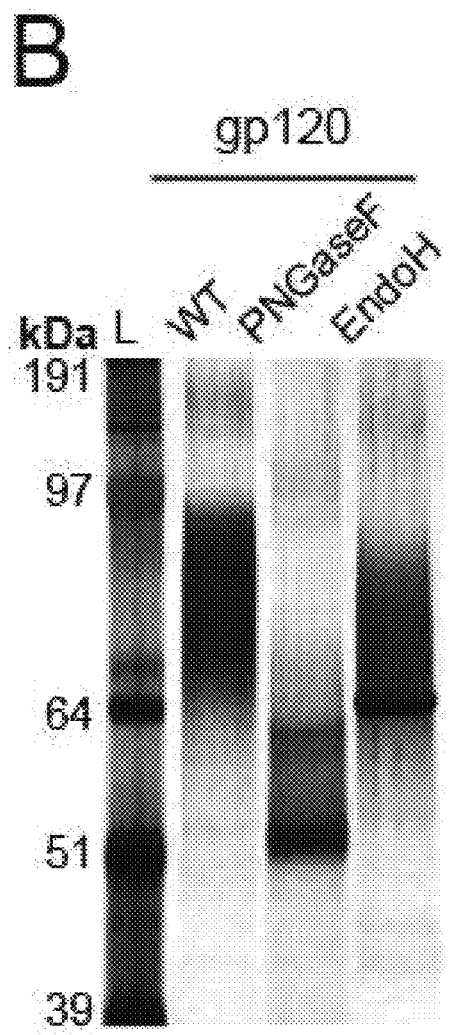
Figure 6C:
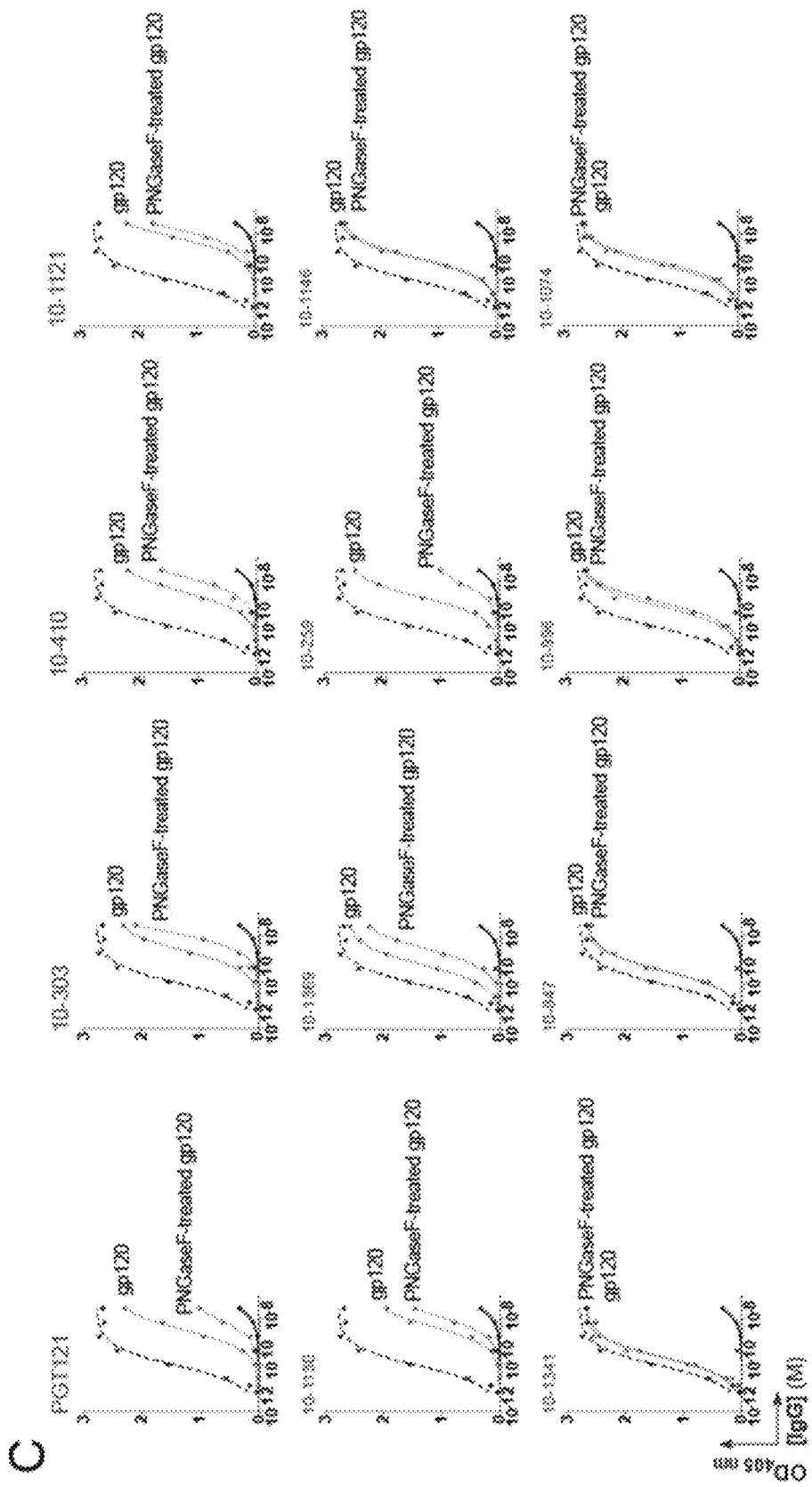
Figure 6D:
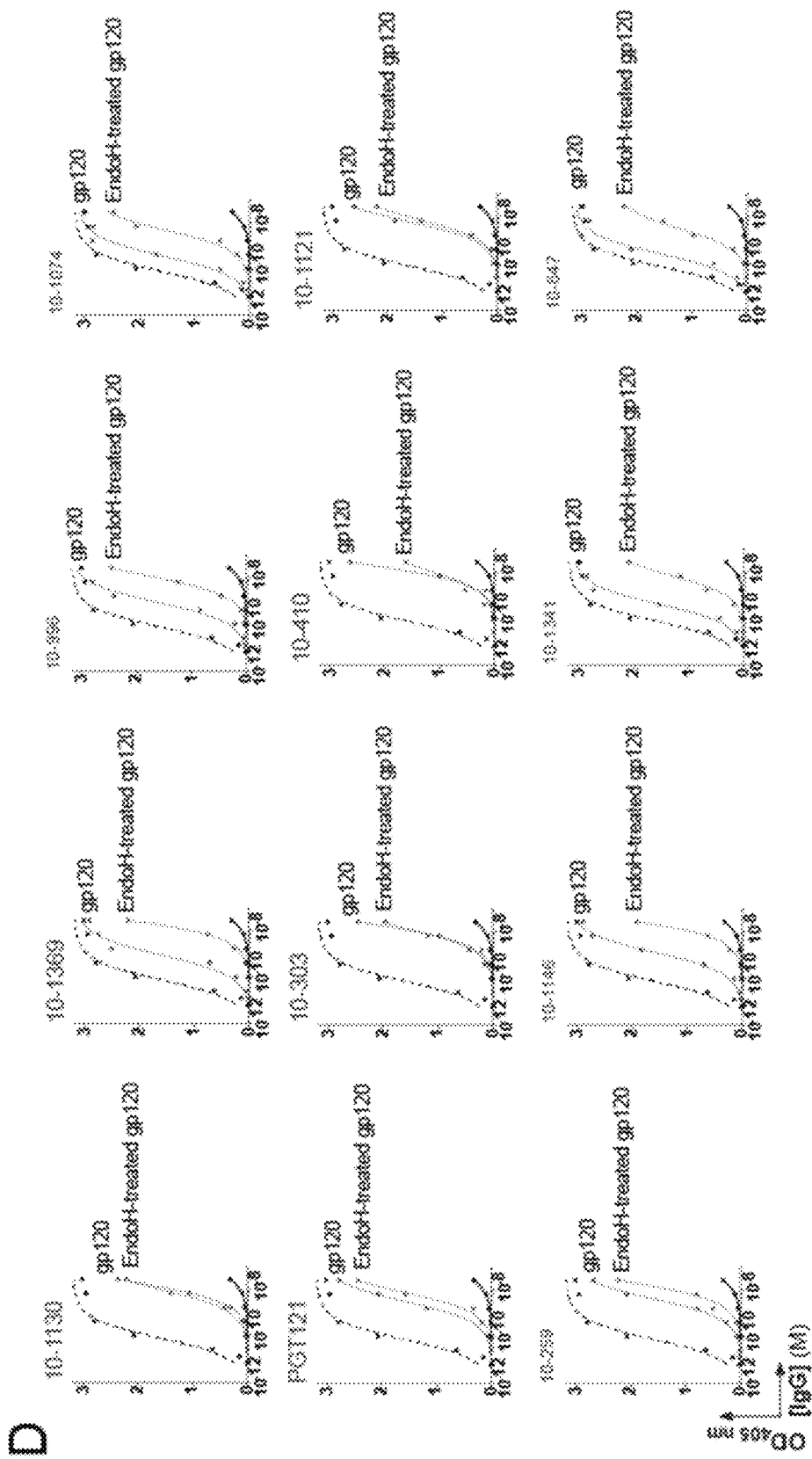

To compare overall glycan recognition by the PGT121- and 10-1074-like antibodies, we examined their binding to YU-2 gp120 treated with PNGase F, which cleaves both complex-type and high-mannose N-glycans. Because gp120 cannot be fully deglycosylated enzymatically unless it is denatured, PNGase F treatment resulted in partial deglycosylation of natively-folded gp120 (FIG. 6). Nevertheless, the reactivities of the two groups of antibodies differed in that partial deglycosylation of gp120 by PNGase F decreased the binding activity of all PGT121-like antibodies but none of the 10-1074-like antibodies (FIG. 6C). Similar experiments conducted with YU-2 gp120 treated with Endo H, which cleaves high-mannose, but not complex-type, N-glycans, affected binding of 10-1074-like antibodies more than PGT121-like antibodies (FIG. 6D).

Figure 7B:
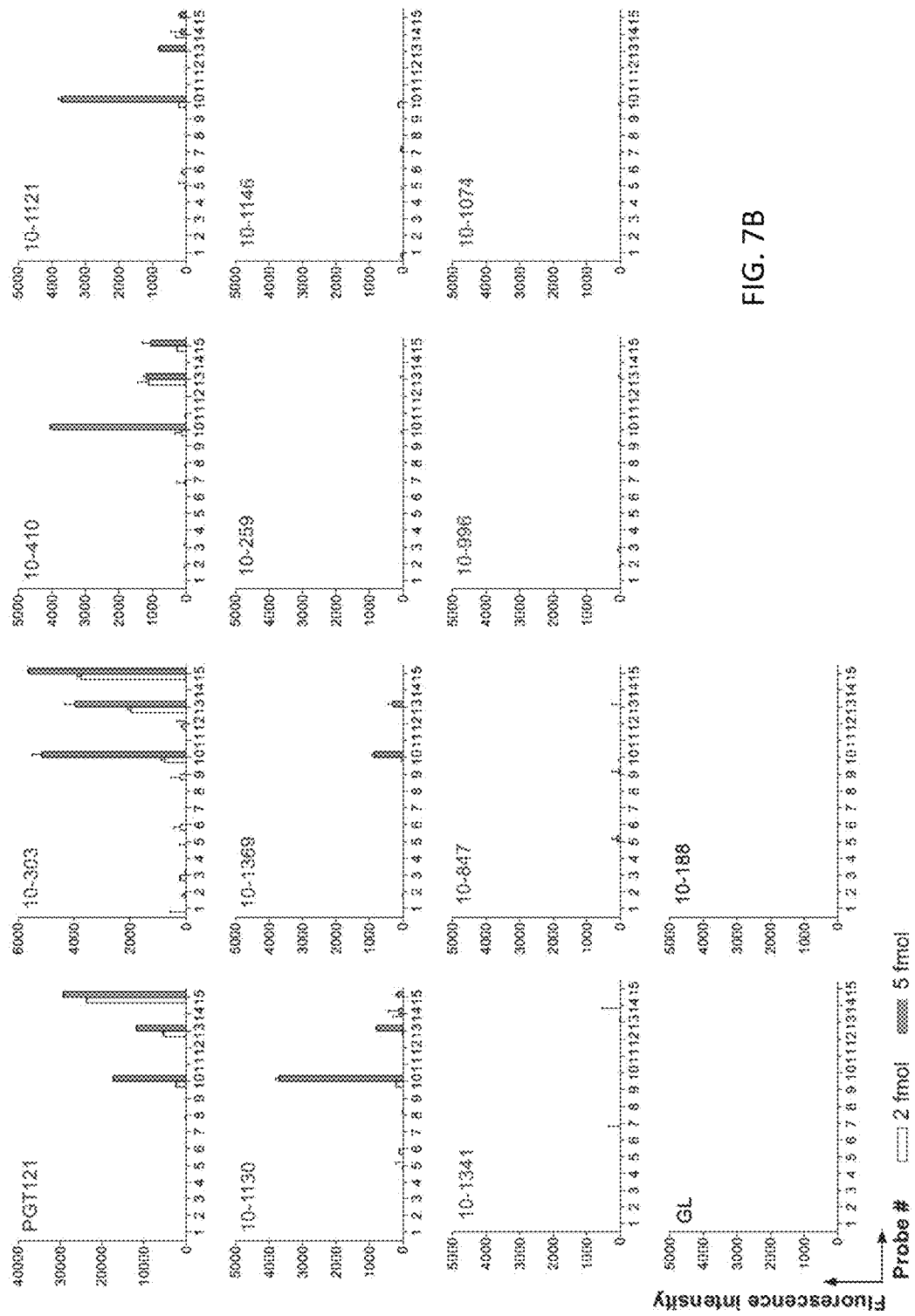

An N-glycan microarray revealed that six of seven tested PGT121-like antibodies showed detectable binding to complex-type mono- or bi-antennary N-glycans terminating with galactose or α2-6-linked sialic acid but no detectable binding to high-mannose type glycans, corroborating and extending previous reports of no binding of PGT121-123 to high-mannose N-glycans and no competition by $Man_4$ and $Man_9$ dendrons for gp120 binding (FIG. 7). In contrast, there was no detectable binding to protein-free glycans by 10-1074-like antibodies (FIG. 7). Although PGT121-like antibodies bound to protein-free complex-type, but not high-mannose, N-glycans, PGT121-like antibodies retained binding to YU-2 gp120 produced in cells treated with kifunensine ($gp120_{kif}$), a mannosidase inhibitor that results in exclusive attachment of high-mannose glycans to PNGSs (FIG. 8B). Most of the PGT121-like antibodies exhibited a small, but reproducible, decrease in binding to $gp120_{kif}$. By contrast, 10-1074-like antibodies retained full binding to $gp120_{kif}$ (FIG. 8B). These results are consistent with the hypothesis that high-mannose, as well as complex-type, N-glycans can be involved in the epitope of PGT121-like antibodies.

Epitope mapping experiments were performed with two representative members of each group (PGT121 and 10-1369 for the PGT121-like group; 10-1074 and 10-996 for the 10-1074-like group) by competition ELISA. All four antibodies showed cross-competition, but PGT121 more modestly inhibited the binding of 10-996 and 10-1074 to gp120 than vice-versa. To further map the targeted epitopes, we used anti-gp120 antibodies that recognize the crown of the V3 loop (FIG. 5), the CD4bs, the co-receptor binding site (CD4-induced; CD4i), a constellation of high-mannose N-glycans (2G12) (Journal of virology 76(14):7293-7305; Proc Natl Acad Sci USA 102(38):13372-13377)), or the V3 loop and N-linked glycans at positions 301 and 332 (PGT128). Anti-V3 crown antibodies inhibited the binding of PGT121 and 10-1369 but did not interfere with the binding of 10-996 and 10-1074. PGT128, and to a lesser extent 2G12, but not the CD4bs and CD4i antibodies, diminished the binding of all four antibodies to gp120.

Taken together, these data suggest that PGT121 clonal members recognize a site involving a protein determinant in the vicinity of the V3 loop and the $Asn332_{gp120}$-associated glycan. However, the clone segregates into two families, the PGT121-like and 10-1074-like groups, which differ in their affinities for gp120 and in the role of glycans in epitope formation.

EXAMPLE 4

Broad and Potent HIV Neutralization

To evaluate the neutralizing activity of the new PGT121 variants, we measured their ability to inhibit HIV infection of TZM-b1 cells using 10 viral strains including R1166.c1, which lacks the PNGS at gp120 position 332. All PGT121 variants, including the 10-1074-like antibodies, neutralized 9 pseudoviruses and none neutralized the R1166.c1 control (FIG. 1A and Table 4). Neutralizing activity correlated with affinity for the HIV spike, with the 10-1074 group showing slightly greater potencies than the PGT121 group (FIG. 1B and FIG. 4C). A representative germline version (GL) of the PGT121/10-1074 antibody clonotype failed to bind gp120/gp140 or neutralize any viruses in the panel, implying that somatic mutation is required for binding and neutralization. Pairing GL light chains with mutated 10-1074- or 10-996-group heavy chains failed to rescue binding or neutralization, suggesting that both mutated chains contribute to proper assembly of the antibody paratope.

Figures 1C, 1D:
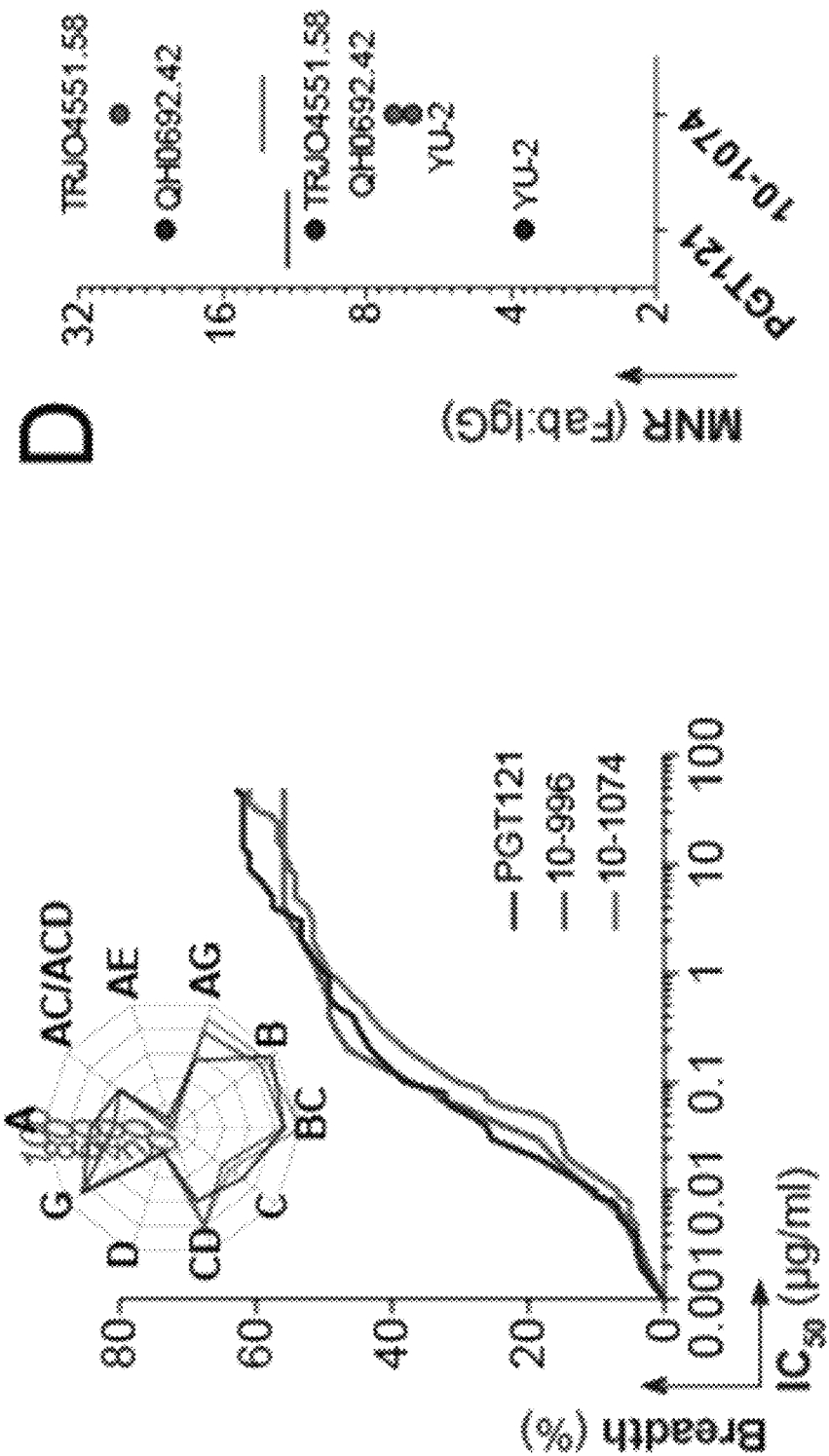
Figure 9A:
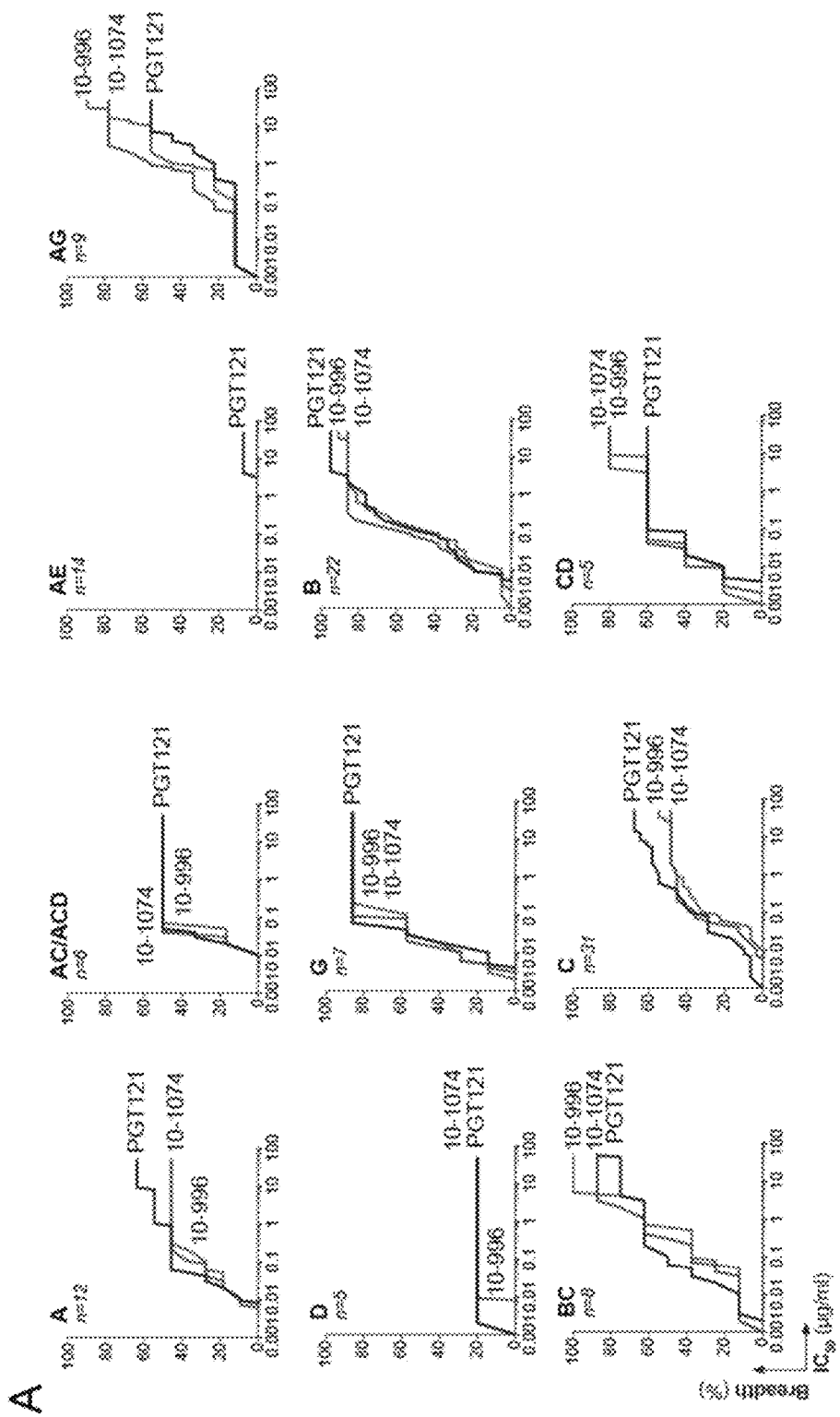
FIGS. 9A, 9B and 9C show: Neutralization activity of PGT121, 10-996 and 10-1074. (A) Graphs comparing the neutralization potencies of PGT121, 10-996 and 10-74 against viruses of the indicated HIV-1 clades (determined using the TZM-b1 assay and a panel of 119 pseudoviruses). The x axis shows the antibody concentration (μg/ml) required to achieve 50% neutralization ($IC_{50}$). The y axis shows the cumulative frequency of $IC_{50}$ values up to the concentration shown on the x axis. (B) Graph comparing the neutralization breadth and potencies of PGT121, 10-996 and 10-1074 antibodies against the extended panel of 119 viruses as determined by the TZM-b1 neutralization assay. The y axis shows the cumulative frequency of $IC_{80}$ values up to the concentration shown on the x axis. (C) Graphs show neutralization curves of the selected viruses by PGT121 and 10-1074. The dotted horizontal line indicates 50% neutralization, from which the $IC_{50}$ value can be derived from the antibody concentration on the x-axis. Experiments were performed in triplicate. Error bars indicate the SD of triplicate measurements.
Figure 9B:
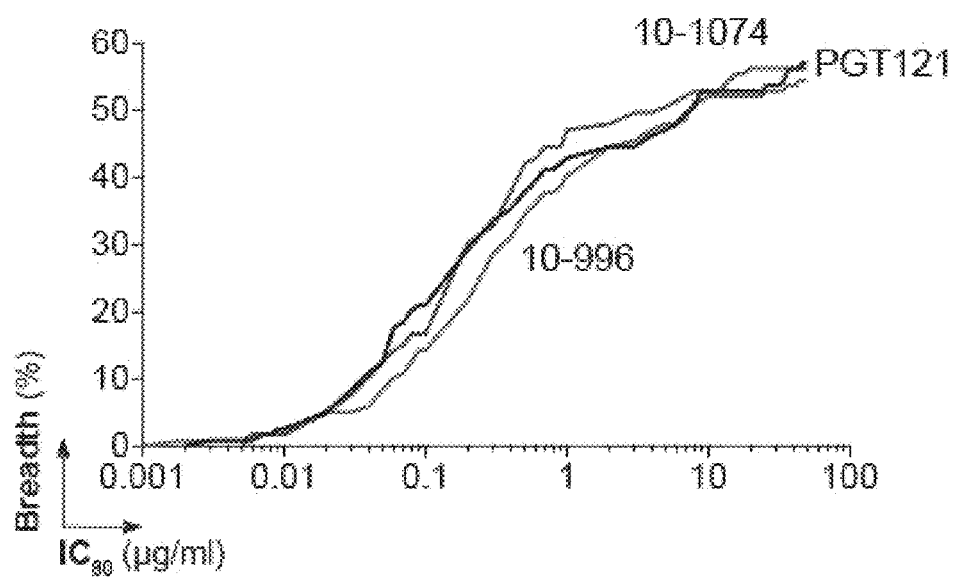
Figure 9C:
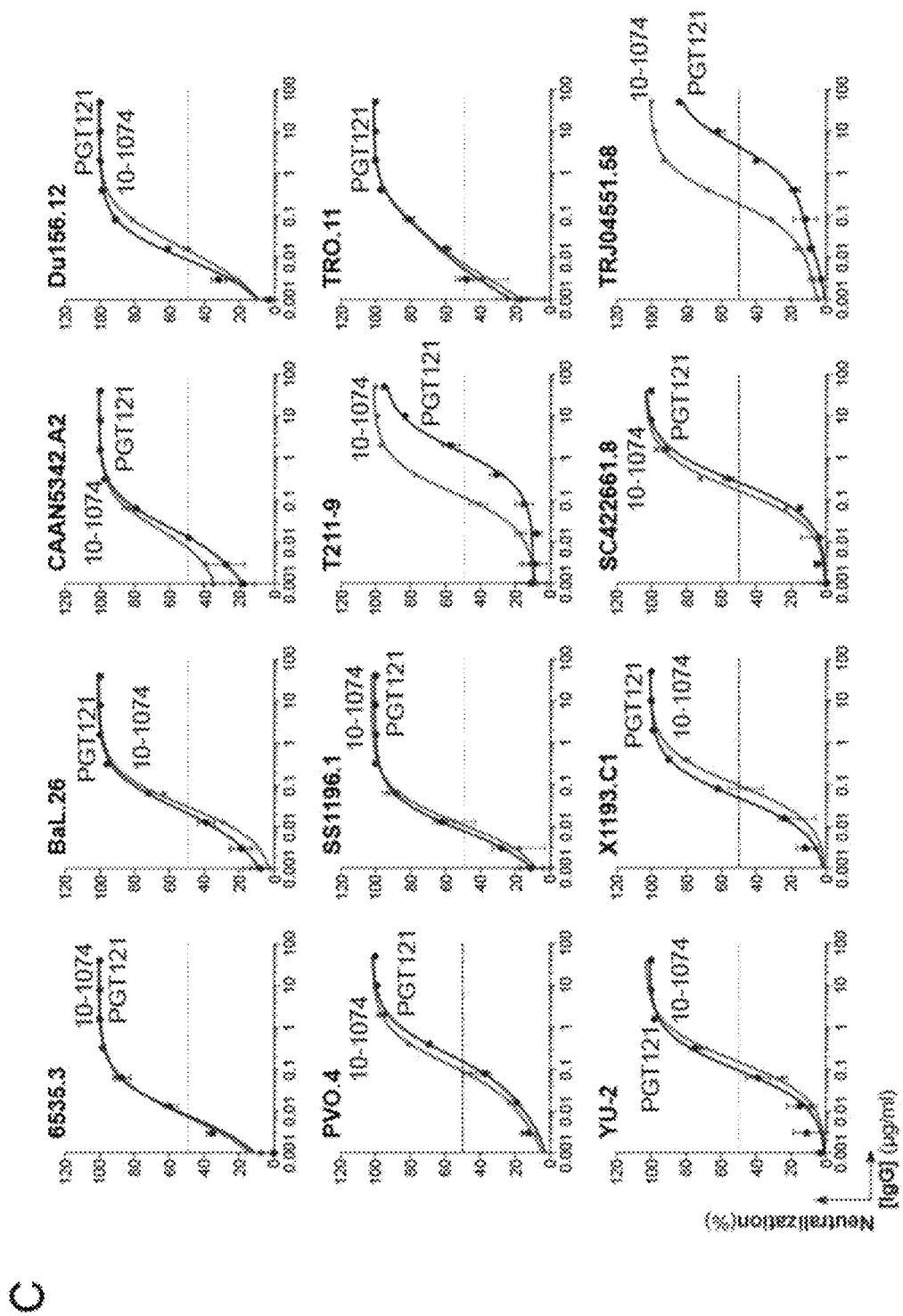

Next assays were carried out to compared the neutralization activities of PGT121 and two 10-1074-like antibodies (10-996 and 10-1074) against an extended panel of 119 difficult-to-neutralize pseudoviruses (classified as tier-2 and tier-3) (Tables 4 and 5). 10-996 and 10-1074 showed neutralization potencies and breadth similar to PGT121 (FIG. 1C, FIG. 9, and Tables 5 and 6). As anticipated, most viruses bearing amino acid changes at gp120 positions 332 and/or 334 (spanning the Asn332-X-Ser334/Thr334 PNGS) were resistant to neutralization (83.8% were resistant to PGT121, 100% were resistant to 10-1074 and 10-996). Mutation at this PNGS accounted for the majority of viruses resistant to neutralization (68.5% for 10-996, 72.5% for 10-1074 and 60.8% for PGT121) (Table 7). Comparable neutralization activities were observed for the IgG and Fab forms of PGT121 and 10-1074, suggesting that bivalency is not critical for their activity (FIG. 1D).

To evaluate the potential role of complex-type N-glycans on the HIV envelope in neutralization by PGT121 and 10-1074, we produced high-mannose-only virions in two different ways: by assembling pseudoviruses in cells treated with kifunensine, which results in $Man_9GlcNAc_2$ N-linked glycans, or by assembly in HEK 293S $GnTI^{-/-}$ cells, which results in $Man_5GlcNAc_2$ N-linked glycans. We found that PGT121 neutralized 2 of 3 kifunensine-derived PGT121-sensitive/10-1074-resistant strains equivalently to their counterparts produced in wildtype cells (FIG. 8C). Two PGT121-sensitive/10-1074-sensitive viral strains produced in $GnTI^{-/-}$ cells were equally as sensitive to PGT121 and 10-1074 as their counterparts produced in wildtype cells. Consistent with previous reports that complex-type N-glycans partially protect the CD4 binding site from antibody binding, the viruses produced in $GnTI^{-/-}$ cells were more sensitive to CD4-binding site antibodies (NIH45-46$^{G54W}$ and 3BNC60) (FIG. 8D).

EXAMPLE 5

Newly-Transmitted HIV-1

Figure 1E:
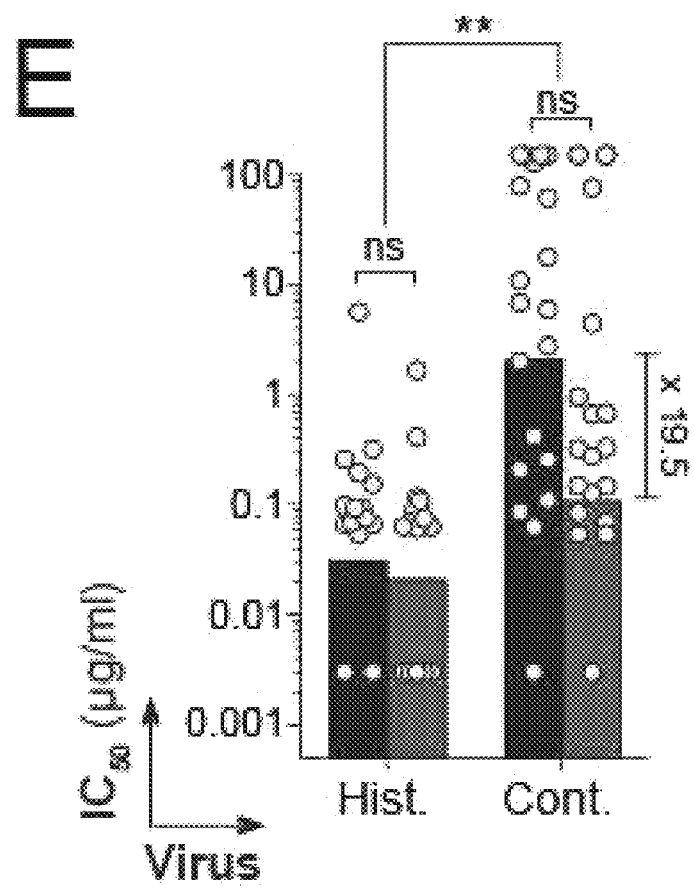
Figure 10:
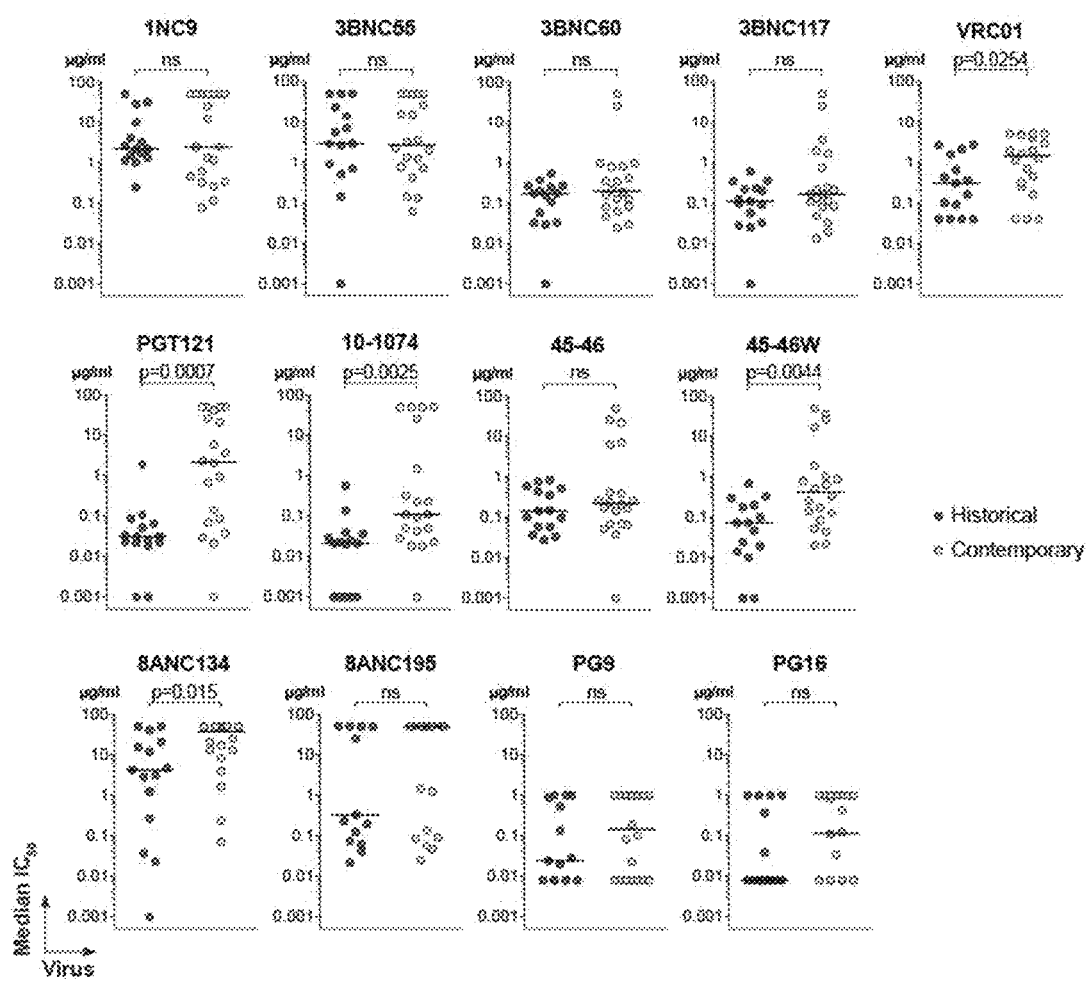
FIG. 10 depicts: Neutralization activity against historical vs contemporary clade B viruses. Dot plots comparing neutralization potencies against clade B viruses isolated from historical (Hist.) and contemporary (Cont.) seroconverters for the selected bNAbs. Horizontal bars represent the median IC$_{50}$ for all viruses per patient. Differences between groups were evaluated using Mann-Whitney test. ns, not significant.

We next examined the activity of PGT121 and 10-1074 against transmitted founder viruses by evaluating neutralization in a peripheral blood mononuclear cell (PBMC)-based assay using 95 clade B viruses isolated from a cohort of individuals who seroconverted between 1985 and 1989 (historical seroconverters, n=14) or between 2003 and 2006 (contemporary seroconverters, n=25) (51, 52). We compared PGT121 and 10-1074 with anti-CD4bs bNAbs and other bNAbs including VRC01, PG9/PG16, b12, 2G12, 4E10 and 2F5. Clustering analyses of neutralization activity showed segregation into two groups; the PGT121/10-1074 group contained the most active HIV neutralizers including the anti-CD4bs and PG9 antibodies (Table 8). Remarkably, 10-1074 showed exceptional neutralization potency on this clade B virus panel, exhibiting the greatest breadth at 0.1 µg/ml (67% of the 95 clade B viruses) of all bNAbs tested (Table 8). Although 10-1074 showed higher potency on contemporary clade B viruses than PGT121 (~20-fold difference), both antibodies were more effective against historical than contemporary viruses (FIG. 1E and FIG. 10).

EXAMPLE 6

Crystal Structures of PGT121, 10-1074 and GL

To investigate the structural determinants of the differences between PGT121-like and 1074-like antibodies, we solved crystal structures of the Fab fragments of PGT121, 10-1074 and a representative germline precursor (GL) at 3.0 Å, 1.9 Å and 2.4 Å resolution, respectively (Table 9). Superimposition of the heavy and light chain variable domains ($V_H$ and $V_L$) among the three Fabs showed conservation of the backbone structure, with differences limited to small displacements of the CDRH3 and CDRL3 loops of the affinity-matured Fabs relative to GL (Table 10).

An unusual feature shared by the antibodies is their long (25 residues) CDRH3 loop, which forms a two-stranded anti-parallel β-sheet extending the $V_H$ domain F and G strands. In each Fab, the tip of the extended CDRH3 loop primarily contains non-polar residues. A similar structural feature was observed for the CDRH3 of PGT145, a carbohydrate-sensitive antibody whose epitope involves the gp120 V1V2 loop. However, the extended two-stranded β-sheet of PGT145's CDRH3 contains mostly negatively-charged residues, including two sulfated tyrosines at the tip. Aligning $V_H$-$V_L$ of PGT121 and PGT145 (Table 10) shows that CDRH3$_{PGT145}$ extends past CDRH3$_{PGT121}$ and that its tip and $V_H$ domain are aligned, whereas the CDRH3s of PGT121, 10-1074 and GL tilt towards $V_L$. The tilting of CDRH3$_{PGT121}$/CDRH3$_{10-1074}$/CDRH3$_{GL}$ towards $V_L$ opens a cleft between CDRH2 and CDRH3, a feature not shared by related antibodies.

PGT121 and 10-1074 are highly divergent with respect to GL and each other (of 132 residues, PGT121$_{VH}$ differs from 10-1074$_{VH}$ and GL$_{VH}$ by 36 and 45 residues, respectively, and 10-1074$_{VH}$ and GL$_{VH}$ differ by 29). The majority of the PGT121/10-1074 differences are located in the CDR$_{VH}$ loops and CDRL3. Interestingly, six substitutions in CDRH3 (residues 100d, 100f, 100h, 100j, 100l, 100n) alternate such that every second residue is substituted, causing resurfacing of the cleft between CDRH2 and CDRH3 that results from CDRH3 tilting towards $V_L$. This region likely contributes to the different fine specificities of PGT121 and 10-1074. Five other solvent-exposed substitutions in heavy chain framework region 3 (FWR3$_{HC}$) (residues 64, 78, 80-82; strands D and E) are potential antigen contact sites given that framework regions in HIV antibodies can contact gp120. Other differences that may contribute to fine specificity differences include a negative patch on PGT121 in the vicinity of Asp56$_{HC}$ not present in 10-1074 or GL (Ser56$_{HC}$ in 10-1074 and GL) and positive patches on the CDRL1 and CDRL3 surface not found on the analogous surface of GL.

Somatic mutations common to PGT121 and 10-1074 may be involved in shared features of their epitopes. The heavy chains of PGT121 and 10-1074 share only three common mutations (of 36 PGT121-GL and 29 10-1074-GL differences). In contrast, PGT121 and 10-1074 share 18 common light chain mutations (of 37 PGT121-GL and 36 10-1074-GL differences), including an insertion in light chain FWR3 that causes bulging of the loop connecting strands D and E, and the substitution of Asp50$_{LC}$-Asp51$_{LC}$ in CDRL2$_{GL}$ to Asn50$_{LC}$-Asn51$_{LC}$ in both PGT121 and 10-1074, resulting in a less negatively-charged surface. The large number of common substitutions introduced into LC$_{PGT121}$ and LC$_{10-1074}$ (approximately 50% of LC substitutions) point to CDRL1, CDRL2 and FWR2$_{LC}$ as potential contact regions for epitopes shared by PGT121 and 10-1074.

Next, comparisons were made with the structure of PGT128, which recognizes Asn332$_{gp120}$- and Asn301$_{gp120}$-linked glycans and V3 and was solved as a complex with an outer domain/mini-V3 loop gp120 expressed in cells that cannot produce complex-type N-glycan-modified proteins. Unlike the CDRH3 loops of PGT121 and 10-1074, PGT128$_{CDRH3}$ is not tilted towards PGT128$_{VL}$, and CDRH3$_{PGT128}$ does not include a two-stranded β-sheet. In addition, CDRH3$_{PGT128}$ (18 residues) is shorter than the CDRH3s of PGT121 and 10-1074 (24 residues), whereas CDRH2$_{PGT128}$ contains a six-residue insertion not found in PGT121 or 10-1074. Due to these differences, CDRH2 is the most prominent feature in PGT128, whereas CDRH3 is most prominent in PGT121 and 10-1074. CDRH2$_{PGT128}$ and CDRL3$_{PGT128}$ together recognize Man$_{8/9}$ attached to Asn332$_{gp120}$, and CDRH3$_{PGT128}$ contacts the V3 loop base. This mode of gp120 recognition is not possible for PGT121 and 10-1074 because the structural characteristics of their CDRH2 and CDRH3 loops differ significantly from those of PGT128, consistent with the ability of PGT128, but not PGT121 and 10-1074 (FIG. 7), to recognize protein-free high-mannose glycans.

EXAMPLE 7

Crystal Structure of PGT121-Glycan Complex

A 2.4 Å resolution structure of PGT121 associated with a complex-type sialylated bi-antennary glycan was solved (Table 9) using crystals obtained under conditions including NA2, a complex-type asialyl bi-antennary glycan (FIG. 7). Surprisingly, the glycan bound to PGT121 in our crystal structure was not NA2, but rather a complex-type N-glycan from a neighboring PGT121 Fab in the crystal lattice; specifically the N-glycan attached to Asn105$_{HC}$. The glycan identity is evident because there was electron density for the glycosidic linkage to Asn105$_{HC}$ and for a terminal sialic acid on the Manα1-3Man antenna (the galactose and sialic acid moieties of Manα1-6Man antenna were unresolved). The composition of the bound glycan corresponds to a portion of the α2-6-sialylated A2(2-6) glycan that was bound by PGT121 in microarray experiments (FIG. 7) and to the expected sialyl linkage on complex-type N-glycans attached to PNGS on proteins expressed in HEK293T cells. Although the $V_H$-$V_L$ domains of this structure ("liganded" PGT121) superimpose with no significant differences onto the $V_H$-$V_L$ domains of the PGT121 structure with no bound N-glycan ("unliganded" PGT121) (Table 10), the elbow bend angle (angle between the $V_H$-$V_L$ and $C_H1$-$C_L$ pseudo-dyads) differs between the structures. This difference likely reflects flexibility that allows the Fab to adopt variable elbow bend angles depending upon crystal lattice forces.

Given that we observed binding of complex-type N-glycan in one crystal structure (the "liganded" PGT121 structure) but not in another structure (the "unliganded" PGT121 structure), we estimate that the affinity of PGT121 for complex-type N-glycan not attached to gp120 is in the range of the concentration of PGT121 in crystals (~10 mM). If we assume that the $K_D$ for binding isolated glycan is in the range of 1-10 mM, comparable to the 1.6 mM $K_D$ derived for PG9 binding to Man$_5$GlcNAc$_2$-Asn, then the $K_D$ for PGT121 binding of isolated glycan represents only a minor contribution to the affinity of PGT121 for gp120, which is in the nM range (FIG. 4A).

The glycan in the "liganded" PGT121 structure interacts exclusively with the $V_H$ domain and makes extensive contacts with residues in all three CDRs (buried surface area on PGT121$_{HC}$=600 Å$^2$). Contacts include 10 direct and 18 water-mediated hydrogen bonds (Table 11) with 9 amino acids anchoring the glycan between the N-acetylglucosamine moiety linked to the branch-point mannose and the terminal sialic acid on the 1-3-antenna. Several contacts with PGT121 are made by this sialic acid, including three direct hydrogen bonds with PGT121 residues Asp31$_{HC}$ and His97$_{HC}$ in addition to water-mediated hydrogen bonds with Asp31$_{HC}$. The sialic acid also contributes to a water-mediated intra-glycan hydrogen bond network. The direct contacts with sialic acid may explain the stronger binding of PGT121 to the sialylated A2(2-6) glycan than to the asialylated NA2 glycan in our glycan microarray analysis (FIG. 7). Extensive water-mediated protein contacts established by the N-acetylglucosamine and galactose moieties of the 1-3-antenna could explain the binding observed for asialylated mono- and bi-antennary glycans to PGT121 (FIG. 7).

Six of the residues contributing direct or likely amino acid side chain contacts to the glycan (Ser32$_{HC-CDRH1}$, Lys53$_{HC-CDRH2}$, Ser54$_{HC-CDRH2}$, Asn58$_{HC-CDRH2}$, His97$_{HC-CDRH3}$, Thr100l$_{HC-CDRH3}$) differ from those on 10-1074 (Tyr32$_{HC-CDRH1}$, Asp53$_{HC-CDRH2}$, Arg54$_{HC-CDRH2}$, Thr58$_{HC-CDRH2}$, Arg97$_{HC-CDRH3}$, Tyr100l$_{HC-CDRH3}$), and are highly conserved among PGT121-like, but not 10-1074-like, antibodies. The 10-1074 residues lack the corresponding functional groups to make the observed glycan contacts or have bulky side chains that would cause steric clashes. Four of these residues also differ from those on GL (Tyr32$_{HC-CDRH1}$, Tyr53$_{HC-CDRH2}$, Gln97$_{HC-CDRH3}$, Tyr1001$_{HC-CDRH3}$), suggesting that the lack of binding of 10-1074-like antibodies and GL to protein-free complex-type glycans in our glycan microarrays results from missing hydrogen bonds and/or steric clashes (e.g., His97$_{PGT121}$ versus Arg97$_{10-1074}$; Thr1001$_{PGT121}$ versus Tyr1001$_{10-1074}$). As the majority of sequence differences between PGT121 and 10-1074 cluster in the CDRH loops, specifically to the surface of the cleft between CDRH2 and CDRH3 where we observe the bound complex-type N-glycan, differential recognition of complex-type glycans on gp120 may account for some or all of the differences in their fine specificity observed.

EXAMPLE 8

Substitution of Glycan-Contacting Antibody Residues affects Neutralization

To evaluate the contributions of complex-type N-glycan contacting residues identified from the "liganded" PGT121 structure, we generated two mutant antibodies designed to exchange the complex-type glycan-contacting residues between PGT121 and 10-1074: a 10-1074 IgG with PGT121 residues (six substitutions in IgH Y32S, D53K, R54S, T58N, R97H, Y1001T) and a PGT121 IgG with reciprocal substitutions. The "glycomutant" antibodies (10-1074$_{GM}$ and PGT121$_{GM}$) exhibited near-wildtype apparent affinity for YU-2 gp120/gp140 as measured by SPR (FIG. 2A), demonstrating that the substitutions did not destroy binding to an envelope spike derived from a viral strain neutralized by both PGT121 and 10-1074 (FIG. 1A). The fact that PGT121 complex-type N-glycan contacting residues can be accommodated within the 10-1074 background without destroying binding to a gp120/gp140 bound by both wildtype antibodies implies overall similarity in antigen binding despite fine specificity differences.

Unlike wildtype PGT121, PGT121$_{GM}$ showed no glycan binding in microarray experiments, confirming that 10-1074 residues at the substituted positions are not compatible with protein-free glycan binding (FIG. 2B) and supporting the suggestion that residues contacting the glycan in the "liganded" PGT121 structure are involved in recognition of complex-type glycans in the microarrays. 10-1074$_{GM}$ also showed no binding to protein-free glycans (FIG. 2B), indicating the involvement of residues in addition to those substituted in creating the binding site for a protein-free complex-type N-glycan.

Figures 2A, 2B, 2C:
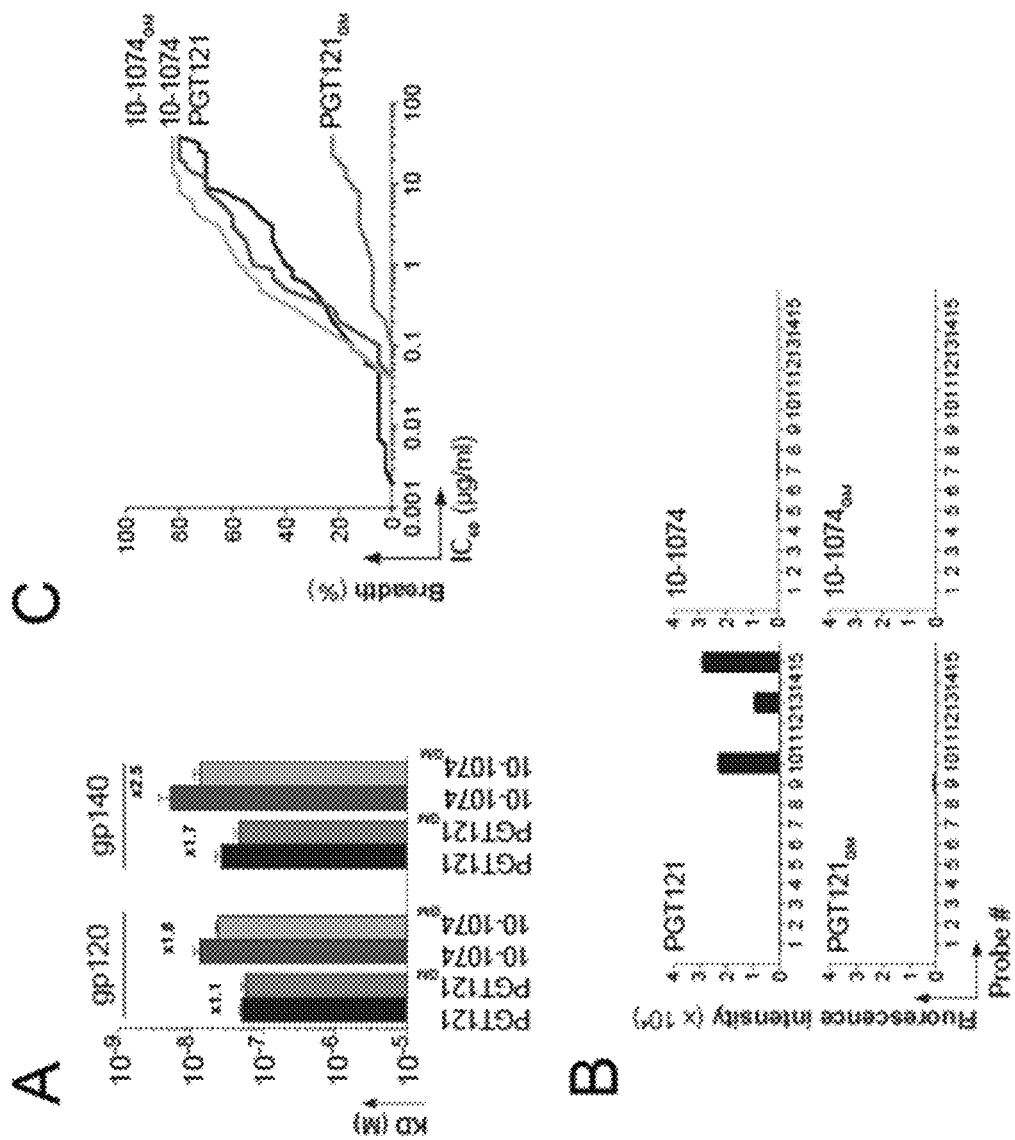
FIGS. 2A, 2B and 2C show: Binding and neutralization activities of $PGT121_{GM}$ and $10\text{-}1074_{GM}$ mutant antibodies. (A) Bar graphs comparing apparent $K_D$ values for the binding of 10-1074, PGT121, $PGT121_{GM}$ and $10\text{-}1074_{GM}$ antibodies to gp120 and gp140. Error bars indicate the SEM of $K_D$ values obtained from three independent experiments. Fold differences between $K_D$ values of "wildtype" vs "glycomutant" antibodies are indicated. (B) Bar graphs comparing binding of glycans (FIG. 7A) by PGT121 and 10-1074 with mutant antibodies ($PGT121_{GM}$ and $10\text{-}1074_{GM}$). Numerical scores of binding are measured as fluorescence intensity (means at duplicate spots) for probes arrayed at 5 fmol per spot. (C) Coverage graph comparing the neutralization breadth and potencies of PGT121, $PGT121_{GM}$, 10-1074 and $10\text{-}1074_{GM}$ antibodies in the TZM-b1 assay against a panel of 40 viruses.

Next, a TZM-b1-based assay was used to compare neutralization of the wildtype and "glycomutant" antibodies. We tested 40 viral strains including strains differentially resistant to PGT121 or 10-1074 and strains sensitive to both wildtype antibodies (FIG. 2C and Table 12). Consistent with the binding of PGT121$_{GM}$ and 10-1074$_{GM}$ to purified YU-2 envelope proteins, both mutants neutralized the YU-2 virus; however, 64% of the PGT121-sensitive strains were resistant to PGT121$_{GM}$ (FIG. 2C, and Table 12) suggesting that the glycan-contacting residues identified in the "liganded" PGT121 structure are relevant to the neutralization activity of PGT121. Conversely, 10-1074$_{GM}$ exhibited a higher average potency than wildtype 10-1074 against the 10-1074-sensitive strains (FIG. 2C and Table 12), including potency increases of >3-fold against four 10-1074-sensitive strains (WITO4160.33, ZM214M.PL15, Cell_H1, and 3817.v2.c59). In general, the PGT121 substitutions into 10-1074 did not confer sensitivity to 10-1074$_{GM}$ upon PGT121-sensitive/10-1074-resistant strains, however two of these strains (CNE19 and 62357_14_D3_4589) became sensitive to 10-1074$_{GM}$ (IC$_{50S}$=0.19 µg/ml and 40.8 µg/ml, respectively). Interestingly, these are the only PGT121-sensitive/10-1074-resistant strains that include an intact Asn33$_{gp120}$-linked PNGS. The other PGT121-sensitive/10-1074-resistant strains lack the Asn332$_{gp120}$-linked glycan and are resistant to PGT121$_{GM}$ and 10-1074$_{GM}$, implying that their sensitivity to wildtype PGT121 involve a nearby N-glycan and/or compensation by protein portions of the epitope. Although a dramatic gain of function was observed only for 10-1074$_{GM}$ against one strain (CNE19), this result, together with the general improvement observed for 10-1074$_{GM}$ against 10-1074-sensitive strains (FIG. 2C), is consistent with the interpretation that the crystallographically-identified glycan-contacting residues can transfer PGT121-like recognition properties to 10-1074 in some contexts and/or affect its potency in others. In addition, the loss of neutralization activity for PGT121$_{GM}$ against PGT121-sensitive strains demonstrates that neutralization activity of PGT121 involves residues identified as contacting complex-type N-glycan in the "liganded" PGT121 structure.

Results

PGT121 is a glycan-dependent bNAb that was originally identified in the serum of a clade A-infected donor in a functional screen yielding only two clonally-related members. gp140 trimers were used as "bait" for single cell sorting to isolate 29 new clonal variants of. The PGT121 clonal family includes distinct groups of closely-related antibodies; the PGT121- and 10-1074-groups. The results suggest that the epitopes of both groups involve the PNGS at Asn332$_{gp120}$ and the base of the V3 loop. The PGT121-like and 10-1074-like antibody groups differ in amino acid sequences, gp120/gp140 binding affinities, and neutralizing activities, with the 10-1074-like antibodies being completely dependent for neutralization upon an intact PNGS at Asn332$_{gp120}$, whereas PGT121-like antibodies were able to neutralize some viral strains lacking the Asn332$_{gp120}$ PNGS.

A notable difference between the two antibody groups is that the PGT121-like antibodies bound complex-type N-glycans in carbohydrate arrays, whereas the 10-1074-like antibodies showed no detectable binding to any of the protein-free N-glycans tested (FIG. 7). Protein-free glycan binding by anti-HIV antibodies is not always detectable; e.g., although PG9 recognizes a gp120-associated high-mannose glycan, no binding to protein-free glycans was detected in microarrays. Thus although a positive result in a glycan microarray implies involvement of a particular glycan in an antibody epitope, a negative result does not rule out glycan recognition. For example, although not detectable in the glycan microarray experiments, high-mannose glycans may be involved in the PGT121 epitope, consistent with binding and neutralization of high-mannose-only forms of gp120 protein and virions (FIG. 8).

The molecular basis for the differences between PGT121, 10-1074 and their GL progenitor was revealed in part by their crystal structures. The finding that the majority of light chain somatic mutations are shared between PGT121 and 10-1074, whereas mutations in the heavy chains differ, suggests that the light chain contacts shared portions of the gp120 epitope and the heavy chain recognizes distinct features. All three antibodies exhibit an extended CDRH3 with a non-polar tip that may allow accessing of cryptic epitopes. Differences in the antigen-binding site of the two mature Fabs were mainly localized to a cleft between CDRH2 and the extended CDRH3. Interestingly, the putative antigen-binding cleft between CDRH2 and CDRH3 was also found in a representative germline progenitor of PGT121 and 10-1074.

Structural information was obtained concerning glycan recognition by PGT121-like antibodies from a crystal structure in which a complex-type sialylated N-glycan attached to a $V_H$ domain residue interacted with the combining site of a neighboring PGT121 Fab. Several features of the "liganded" PGT121 structure suggest it is relevant for understanding the recognition of complex-type N-glycans on gp120 by PGT121-like antibodies. First, the glycan in the structure corresponds to the α2-6 sialylated glycan A2(2-6) PGT121 binds in microarrays (FIG. 7). Second, the glycan interacts with PGT121 using the cleft between CDRH3 and CDRH2 that was suggested by structural analyses to be involved in epitope recognition, potentially explaining the unusual tilting of CDRH3 towards $V_L$ in the PGT121 and 10-1074 structures. Third, most of the $V_H$ residues identified as interacting with the glycan differ between PGT121 and 10-1074, rationalizing different binding profiles in glycan microarrays and potentially explaining the different fine specificities revealed in protein binding experiments. Fourth, swapping crystallographically-identified glycan contact residues between PGT121 and 10-1074 in part transferred their properties: PGT121$_{GM}$, like 10-1074, did not bind to protein-free glycans, but both PGT121$_{GM}$ and 10-1074$_{GM}$ preserved near wildtype binding to purified YU-2 gp120/gp140. Although PGT121$_{GM}$ retained the ability to neutralize some viral strains that were neutralized by wildtype PGT121 and 10-1074, it failed to neutralize strains that are PGT121-sensitive/10-1074-resistant, demonstrating that the glycan-binding motif is essential for the neutralizing activity of PGT121 against 10-1074-resistant strains. For the reciprocal swap, the neutralization potency of 10-1074$_{GM}$ was increased or unaffected relative to 10-1074, and in one case, 10-1074$_{GM}$ potently neutralized a PGT121-sensitive/ 10-1074-resistant strain, consistent with transfer of the crystallographically-identified glycan motif and the hypothesis that the epitopes of PGT121- and 10-1074-like antibodies are related. In analyses of gp120 sequences from strains for which PGT121 neutralization data are available, other than a correlation with the PNGS at Asn332gp120 for viruses sensitive to PGT121-like and 10-1074-like antibodies, no clear pattern of PNGS usage emerges for the different categories of viral strains (PGT121-sensitive/10-1074-sensitive, PGT121-sensitive/10-1074-resistant, PGT121-resistant/10-1074-sensitive) except that the 10-1074-resistant strains generally lack the Asn332gp120-associated PNGS.

EXAMPLE 9

Passive Transfer of Anti-HIV-1 Neutralizing mAbs In-Vivo

Five isolated potent and broadly acting anti-HIV neutralizing monoclonal antibodies were administered to rhesus macaques and challenged them intrarectally 24 h later with either of two different SHIVs. By combining the results obtained from 60 challenged animals, the protective neutralization titer in plasma preventing virus acquisition in 50% of the exposed monkeys was approximately 1:100.

Animal Experiments

The macaques used in this study were negative for the MEC class I Mamu-A*01 allele.

Construction of the R5-tropic SHIVDH12-V3AD8

PCR mutagenesis, with primers corresponding to the 5' and 3' halves of the SHIVAD8EO (PNAS 109, 19769-19774 (2012)) gp120 V3 coding region (forward primer: AGAG-CATTTTATACAACAGGAGACATAATAGGAGA-TATAAGACAAGCACATTGCAA CATTAGTAAAG-TAAAATGGC (SEQ ID NO: 214) and reverse primer: TCCTGGTCCTATATGTATACTTTTCCTTGTATTGTT-GTTGGGTCTTGTACAATTAATTT CTACA-GTTTCATTC (SEQ ID NO: 215)), was employed to introduce these V3 sequences into the genetic background of the pSHIVDH12.CL7 molecular clone (J. of Virology 78, 5513-5519 (2004)), using Platinum PFX DNA polymerase (Invitrogen). Following gel purification, the PCR product was treated with T4 polynucleotide kinase (GibcoBRL) and blunt-end ligated to create pSHIVDH12.V3AD8, which was used to transform competent cells.

Viruses

Virus stocks were prepared by first transfecting 293T cells with the SHIVAD8EO or SHIVDH12-V3AD8 molecular clones using Lipofectamine 2000 (Invitrogen, Carlsbad, Calif.). Culture supernatants were collected 48 h later and aliquots stored at −80° C. until use. Concanavalin A-stimulated rhesus PBMCs (2×10$^6$ cells in 500 µl) were infected with transfected cell supernatants by spinoculation (J. of Virology 74, 10074-10080 (2000)) for 1 h, mixed with the same number/volume of activated PBMC, and cultures were maintained for at least 12 days with daily replacement of culture medium. Samples of supernatant medium were pooled around the times of peak RT production to prepare individual virus stocks.

Antibodies

Eleven monoclonal antibodies (VRC01, NIH45-46, 45-46G54W, 45-46m2, 3BNC117, 12A12, 1NC9, and 8ANC195, 10-1074, PGT121, and PGT126) were isolated and produced. DEN3, a dengue virus NS1-specific human IgG1 monoclonal antibody (PNAS 109, 18921-18925 (2012)), or control human IgG (NIH Nonhuman Primate Reagent Resource) were used as the negative control antibodies in this study. The monoclonal antibodies selected for pre-exposure passive transfer were administered intravenously 24 h before virus challenge.

Quantitation of plasma viral RNA levels.

Viral RNA levels in plasma were determined by real-time reverse transcription-PCR (ABI Prism 7900HT sequence detection system; Applied Biosystems).

Antibody concentrations in plasma.

The concentrations of administered monoclonal antibodies in monkey plasma were determined by enzyme-linked immunosorbent assay (ELISA) using recombinant HIV-1JRFL gp120 (Progenics Pharmaceuticals) or HIVIIIB (Advanced Biotechnology inc) (J. of Virology 75, 8340-8347 (2001)). Briefly, microtiter plates were coated with HIV-1 gp120 (2 µg/ml) and incubated overnight at 4° C. The plates were washed with PBS/0.05% Tween-20 and blocked with 1% (vol/vol) BSA. After blocking, serial dilution of antibodies or plasma samples were added to the plate and incubated for 1 h at room temperature. Binding was detected with a goat anti-human IgG F(ab)2 fragments coupled to alkaline phosphatase (Pierce) and visualized with SIGMA-FAST OPD (Sigma-Aldrich). The decay half-lives of neutralizing monoclonal antibodies were calculated by a single-exponential decay formula based on the plasma concentrations beginning on day 5 or day 7 post antibody administration (J. of Virology 84, 1302-1313 (2010)).

Neutralization assays.

The in vitro potency of each mAb and the neutralization activity present in plasma samples collected from rhesus macaques were assessed by two types of neutralization assays; 1) TZM-b1 entry assay with pseudotyped challenge virus (AIDS Res Hum Retroviruses 26, 89-98 (2010)) or 2) a 14 day PBMC replication assay with replication competent virus (J. of virology 76, 2123-2130 (2002)). For the TZM-b1 assay, serially diluted mAb or plasma samples were incubated with pseudotyped viruses, expressing env gene derived from SHIVAD8EO or SHIVDH12.V3AD8 and prepared by cotransfecting 293T cells with pNLenv1 and pCMV vectors expressing the respective envelope proteins (J. of Virology 84, 4769-4781 (2010)). The 50% neutralization inhibitory dose (IC50) titer was calculated as the dilution causing a 50% reduction in relative luminescence units (RLU) compared with levels in virus control wells after subtraction of cell control RLU (J. of Virology 84, 1439-1452 (2010)). The neutralization phenotype (tier levels) of the SHIVDH12.V3AD8 molecular clone was determined by TZM-b1 cell assay using plasma samples from a cohort study, which exhibit a wide range of neutralizing activities against subtype B HIV-1 isolates (J. of General Virology 91, 2794-2803 (2010)).

Determinations of animal protective titers and statistical analyses.

Calculation of the neutralizing titer in plasma against each R5 SHIV, resulting in the prevention of virus acquisition of 50 or 80% of the virus-challenged animals, was performed using the method of Reed and Muench (Am J Hyg 27, 493-497 (1938)). One significant outlier animal (DEW7) was omitted from the calculation. Probit regression was used to model the relationship between the titers in plasma required to confer sterilizing immunity in vivo using all 60 passively immunized monkeys (Cambridge University Press, Cambridge, England, ed. 3rd, 2007), with p-values from this model based on Likelihood ratio Tests. Plasma titers needed for different levels of in vivo protection (33%, 50%, 80%, 90%, and 95%) were determined from the probit model estimates and the method of bootstrapping was used to construct 90% confidence intervals. Results:

SHIVDH12-V3AD8, like SHIVAD8EO, possesses Tier 2 anti-HIV-1 neutralization sensitivity properties (Table 13). Rhesus macaques inoculated intravenously or intrarectally with SHIVDH12-V3AD8 exhibited peak viremia ranging from 105 to 107 viral RNA copes/ml of plasma at weeks 2 to 3 post infection (PI). In most SHIVDH12-V3AD8 infected animals, plasma viral loads decline to background levels between weeks 8 to 20 PI.

The neutralization sensitivity of SHIVAD8EO to 11 recently reported broadly reacting anti-HIV-1 mAbs was initially determined in the TZM-b1 assay system (FIGS. 11A and B). Eight of these antibodies, VRC01, NIH45-46 (23), 45-46G54W, 45-46m2, 3BNC117, 12A12, 1NC9, and 8ANC195 targeted the gp120 CD4 bs (Science 333, 1633-1637 (2011)) and three, 10-1074, PGT121, and PGT126 (Nature 477, 466-470 (2011)), were dependent on the presence of the HIV-1 gp120 N332 glycan. When tested against SHIVAD8EO, all three glycan-dependent mAbs exhibited greater potency than the CD4 bs mAbs (FIG. 11A). The IC50 values for the three mAbs targeting the gp120 N332 glycan ranged from 0.09 to 0.15 µg/ml. The CD4 bs mAbs exhibited a much broader range (0.14 to 6.34 µg/ml) of IC50 neutralizing activity with 3BNC117 being the most potent. A similar hierarchy (glycan-dependent>CD4 bs dependent) of neutralizing mAb potency was also observed with SHIVDH12-V3AD8, but the neutralizing activity was distributed across a much wider (>100 fold) range compared to the IC50 values observed for SHIVAD8EO (FIG. 11B). SHIVDH12-V3AD8 was somewhat more sensitive to the glycan targeting mAbs and more resistant to the CD4 bs neutralizing mAbs than SHIVAD8EO.

Based on the results shown in FIG. 11, five neutralizing mAbs were selected for a pre-exposure passive transfer study: VRC01, because it was the first CD4bs NAb of the newly isolated broadly acting NAbs to be characterized; the CD4 bs mAbs 45-46m2 and 3BNC117, both of which exhibited strong neutralizing activity against SHIVAD8EO and SHIVDH12-V3AD8; and the gp120 N332 glycan-dependent mAbs, PGT121 and 10-1074.

The protocol for passive transfer experiments was to administer decreasing amounts of neutralizing mAbs intravenously and challenge animals intrarectally 24 h later. The goal was to block virus acquisition, coupled with the knowledge that repeated administrations of humanized anti-HIV mAbs to individual macaques could reduce their potency and/or possibly induce anaphylactic responses, a SHIV challenge dose of sufficient size to establish an in vivo infection following a single inoculation was chosen. In this regard, we had previously conducted intrarectal titrations of SHIVAD8 in rhesus monkeys and reported that the inoculation of 1×103 TCID50, determined by endpoint dilution in rhesus macaque PBMC, was equivalent to administering approximately 3 animal infectious doses50 (AID50) (J. of virology 86, 8516-8526 (2012)). In fact, single intrarectal inoculations of 3 AID50 have resulted in the successful establishment of infection in 10 of 10 rhesus macaques with SHIVAD8EO or SHIVDH12-V3AD8.

As a control for the first passive transfer experiment, an anti-dengue virus NS1 IgG1 mAb was administered intravenously to animals, which were challenged with SHIVAD8EO 24 h later. Both monkeys (ML1 and MAA) rapidly became infected, generating peak levels of plasma viremia at week 2 PI. VRC01 was the first anti-HIV-1 neutralizing mAb tested for protection against virus acquisition and was administered to two macaques at a dose of 50 mg/kg. One (DEGF) of the two inoculated macaques was completely protected from the SHIVAD8EO challenge, with no evidence of plasma viremia or cell-associated viral DNA over a 45 week observation period. The other recipient of 50 mg/kg VRC01 (DEH3) became infected, but peak plasma viremia was delayed until week 5 PI. Two additional macaques administered lower amounts (20 mg/kg) of VRC01 were not protected from the SHIVAD8EO challenge. These results are summarized in Table 13.

Examined next, the protective properties of PGT121 against a SHIVAD8EO challenge. PGT121 was one of the most potent glycan targeting neutralizing mAbs measured in the TZM-b1 assay (FIG. 11). Based on the results obtained with VRC01, in vivo PGT121 mAb titration at 20 mg/kg was chosen to begin with. The two challenged monkeys (KNX and MK4) resisted the SHIVAD8EO challenge. When lower amounts (viz. 5 mg/kg, 1 mg/kg, or 0.2 mg/kg) of PGT121 were administered, 1 of 2, 2 of 2, and 0 of 2 animals, respectively, were protected (Table 13).

The capacity of VRC01 and PGT121 mAbs to block SHIVDH12-V3AD8 acquisition was similarly evaluated (Table 13). The results obtained with VRC01 were comparable to those observed with the SHIVAD8EO challenge: 1 of 2 recipients of 30 mg/kg was protected from the establishment of a SHIVDH12-V3AD8 infection. The PGT121 mAb was considerably more potent than VRC01 in preventing SHIVDH12-V3AD8 acquisition: 2 of 2 recipients of 0.2 mg/kg PGT121 resisted infection. PGT121 also appeared to be somewhat more effective in preventing SHIVDH12-V3AD8 versus SHIVAD8EO in vivo infections (Table 13). This result is consistent with the 8-fold difference in IC50 values for PGT121 for neutralizing the two SHIVs in in vitro assays (FIG. 11).

The results of passively transferring 10-1074, 3BNC117, or 45-46m2 neutralizing mAbs to rhesus monkeys, followed by a challenge with either SHIVAD8EO or SHIVDH12-V3AD8, are summarized in Table 13. The 10-1074 mAb potently blocked the in vivo acquisition of both SHIVs. The CD4bs 3BNC117 and 45-46m2 mAbs were selected for passive transfer to macaques based on their IC50 values against both SHIVs in the in vitro neutralization experiments shown in FIG. 11. 3BNC117 successfully blocked SHIVAD8EO infection in 2 of 2 monkeys at 5 mg/kg but not in 2 other animals given a dose of 1 mg/kg (Table 13). This was similar to the results observed when the same amounts of 3BNC117 were administered to macaques challenged with SHIVDH12-V3AD8: 1 of 2 became infected at 5 mg/kg; 1 of 2 became infected at 1 mg/kg.

Plasma samples collected at various times from passively transferred macaques were analyzed by HIV-1 gp120 ELISA to determine neutralizing mAb concentrations. In general, the plasma concentrations of each mAb at the time of challenge (24 h following antibody administration) correlated with the dose of antibody administered (Table 13).

Figure 12:
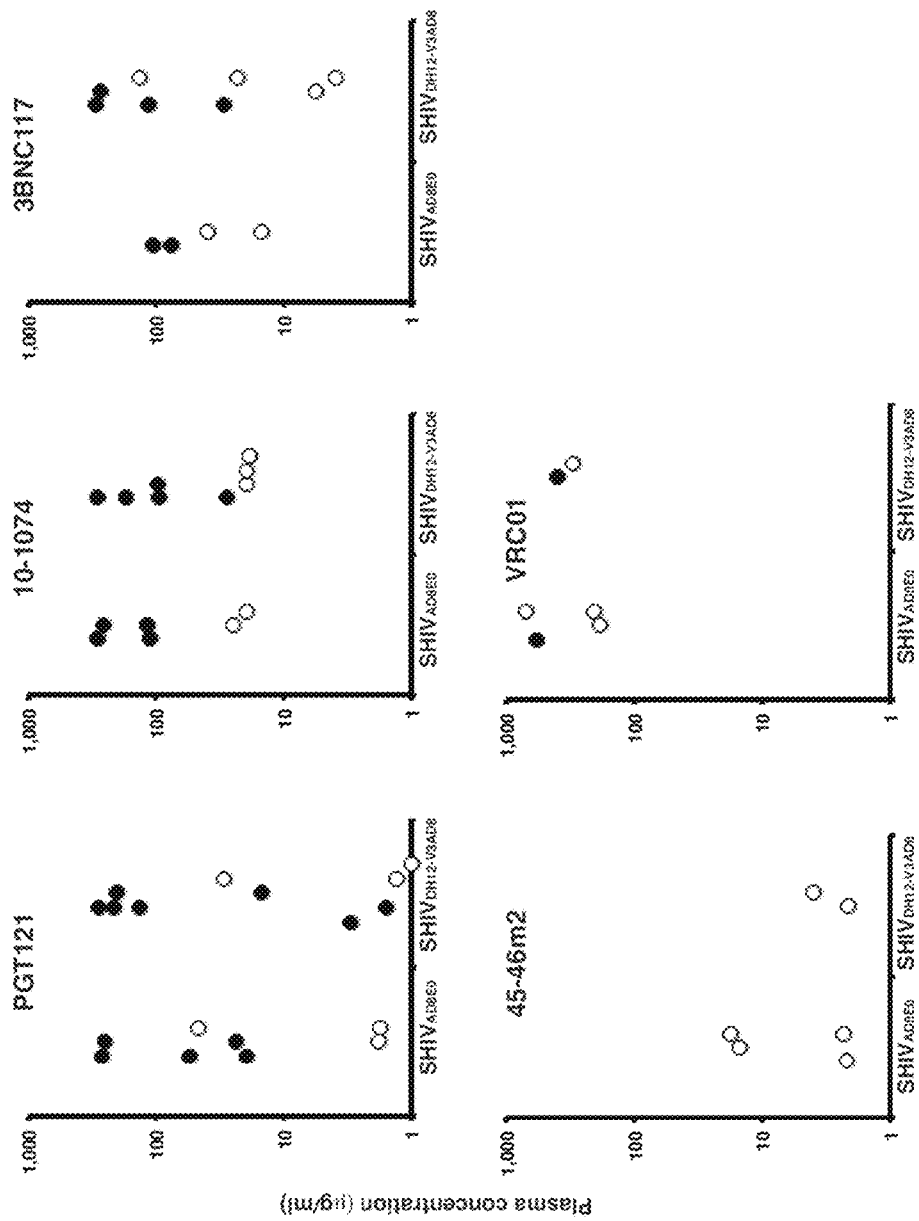
FIG. 12 depicts: The relationship of the plasma concentrations of passively administered neutralizing mAbs to virus acquisition following challenge of macaques with two different R5 SHIVs. Filled circles indicate protected (no acquisition) monkeys; open circles denote infected animals.

The relationships of plasma mAb concentrations to in vivo protection are shown in FIG. 12. Of the 5 neutralizing mAbs evaluated, PGT121 was clearly the most effective against both viruses, with SHIVDH12-V3AD8 exhibiting somewhat greater sensitivity to this mAb (2 of 2 monkeys protected at a plasma concentration of 0.2 µg/ml). In contrast, a plasma concentration of nearly 400 µg/ml of VRC01 was required to protect 1 of 2 animals against the same SHIVDH12-V3AD8 challenge virus (Table 13). The most potent CD4 bs mAb administered to macaques in this study, 3BNC117, was approximately 6 to 10-fold more effective than VRC01 in preventing the acquisition of either SHIV (FIG. 12, Table 13).

The calculated half lives of PGT121, 10-1074, 3BNC117, and VRC01 mAbs were quite similar: 3.5days, 3.5 days, 3.3 days, and 3.1 days, respectively. In contrast, the half-life of 45-46m2 was extremely short and could not be determined. Based on the plasma mAb concentrations in several macaques 24 h following the administration of 20 mg/kg of humanized neutralizing mAbs (viz. approximately 250 µg/ml [Table 13]), the two monkeys receiving 20 mg/kg of 45-46m2 had plasma mAb concentrations of only 15.0 and 17.6 µg/ml, a decay of more than 95% relative to other neutralizing mAbs in 24 h.

Neutralization titers were measured on plasma samples collected 24 h following mAb administration when the macaques were challenged with SHIVAD8EO or SHIVDH12-V3AD8. As shown in Table 13, good correlation was observed between anti-viral plasma neutralization titers and protection from SHIV infection. The administration of the two glycan-dependent mAbs (PGT121 and 10-1074) clearly resulted in the highest titers of anti-HIV-1 neutralizing activity at the time of virus challenge. The titers measured in recipients of the 45-46m2 mAb were at the limits of detection or undetectable due to its extremely short half-life in vivo.

The method described by Reed and Muench (Am J Hyg 27, 493-497 (1938)) was used to calculate the neutralization titers, measured in plasma, needed to prevent virus acquisition in 50% of challenged monkeys. These protective titers for the 28 monkeys, challenged with SHIVAD8EO, or the 32 monkeys, challenged with SHIVDH12-V3AD8, were separately deduced (Tables 15 and 16). The plasma neutralization titers required for protecting 50% of the SHIVAD8EO or SHIVDH12-V3AD8 challenged animals were calculated to be 1:115 and 1:96, respectively. Because these similar titers were obtained following: 1) SHIV challenges by identical routes and inoculum size and 2) the administration of the same ensemble of neutralizing mAbs, the neutralization data from all 60 animals were combined and subjected to probit regression to examine the relationship between plasma neutralization titers and in vivo protection. As a further check, when a term for the SHIV virus was included in the probit regression model on all 60 macaques, there was no evidence of a difference between the two SHIV viruses (p=0.16). When applied to the entire group of 60 macaques, probit regression estimated that plasma neutralization titers of 1:104 would prevent virus acquisition in 50% of animals. Probit analysis of the data also estimates that 50% plasma neutralization titers of 1:57 or 1:329 would protect 33% or 80%, respectively, of exposed animals.

EXAMPLE 10

Administration of Neutralizing mAbs to Chronically Infected HIV In-Vivo Models

Methods Summary: The neutralization activities of the broadly acting 3BNC11724 and 10-107423 neutralizing mAbs against SHIVAD8EO were initially determined in the TZM-b1 cell system against SHIVAD8EO. Their capacities to block virus acquisition or to control plasma viremia in chronically infected animals challenged with the R5-tropic SHIVAD8EO were assessed by monitoring plasma viral loads and cell-associated viral nucleic acids; levels of CD4+ T cell subsets were measured by flow cytometry. SGA analyses of circulating viral variants and the determination of antibody levels in plasma. Plasma concentration of NAbs was determined by measuring neutralizing activity against HIV-1 pseudovirus preparations only susceptible to either 10-1074 or 3BNC117.

Results:

Two groups of chronically infected macaques were assessed. The first group consisted of two clinically asymptomatic animals (DBZ3 and DC99A) that had been infected for 159 weeks and had sustained similar and significant declines of circulating CD4+ T cells (Table 17). The regimen for treating ongoing SHIV infections was to co-administer 101074 and 3BNC117, at a dose of 10 mg/kg. At the time of mAb administration, the plasma viral loads in macaques DBZ3 and DC99A were $1.08 \times 10^4$ and $7.6 \times 10^3$ RNA copies/ml, respectively. Both monkeys responded to combination anti-HIV-1 mAb treatment with immediate and rapid reductions of plasma viremia to undetectable levels within 7 to 10 days. Suppression of measurable SHIVAD8EO in the plasma of macaques DBZ3 and DC99A, following a single administration of the two mAbs, lasted 27 and 41 days, respectively. In each case, plasma viremia rebounded to pretreatment levels.

A second group of three animals (DBX3, DCF1, and DCM8), each of which were also infected with SHIVAD8EO for more than 3 years and were clinically symptomatic with intermittent diarrhea and or anorexia, were treated with the two neutralizing antibodies (Table 17). At the time of mAb administration, the level of circulating CD4+ T cells in macaque DCM8 was only 43 cells/µl and somewhat higher in animals DCF1 (105 cells/μl) and DBXE (158 cells/μl). Plasma viral loads exceeded 105 RNA copies/ml in animals DBXE and DCF1 and were significantly lower (1.59×103 RNA copies/ml) in monkey DCM8. The administration of the two mAbs to monkey DBXE resulted in a biphasic reduction of viremia from 2.0×105 RNA copies at day 0 to undetectable levels in plasma at day 20. This was followed, within a few days, by a resurgence of high levels of circulating virus in DBXE. Macaque DCM8, with more modest plasma virus loads and very low numbers of circulating CD4+ T cells, experienced a rapid decline of viremia to undetectable levels between days 6 and 20 following the initiation of mAb treatment. Finally, animal DCF1, previously reported to have generated broadly reacting anti-HIV-1 NAbs, exhibited a transient and a comparatively modest 27-fold reduction of plasma viremia by day 6 in response to combination mAb therapy, before the viral loads returned to high pretreatment levels.

PBMC associated viral RNA and DNA levels were also determined prior to and following antibody administration (Table 18). For each animal, mAb treatment resulted in reduced levels of cell associated viral RNA, correlating well with the plasma viral load measurements. No consistent pattern was observed for cell associated viral DNA levels as a result of antibody treatment. Administration of neutralizing mAbs to chronically SHIVAD8EO infected monkeys also had beneficial effects on circulating CD4+ T cell levels, particularly in animals with very high virus loads. The CD4+ T cell numbers in macaques DBXE and DCF1 increased 2 to 3 fold during the period of mAb mediated virus suppression, but gradually declined to pretreatment levels as viremia again became detectable.

Figure 13C:
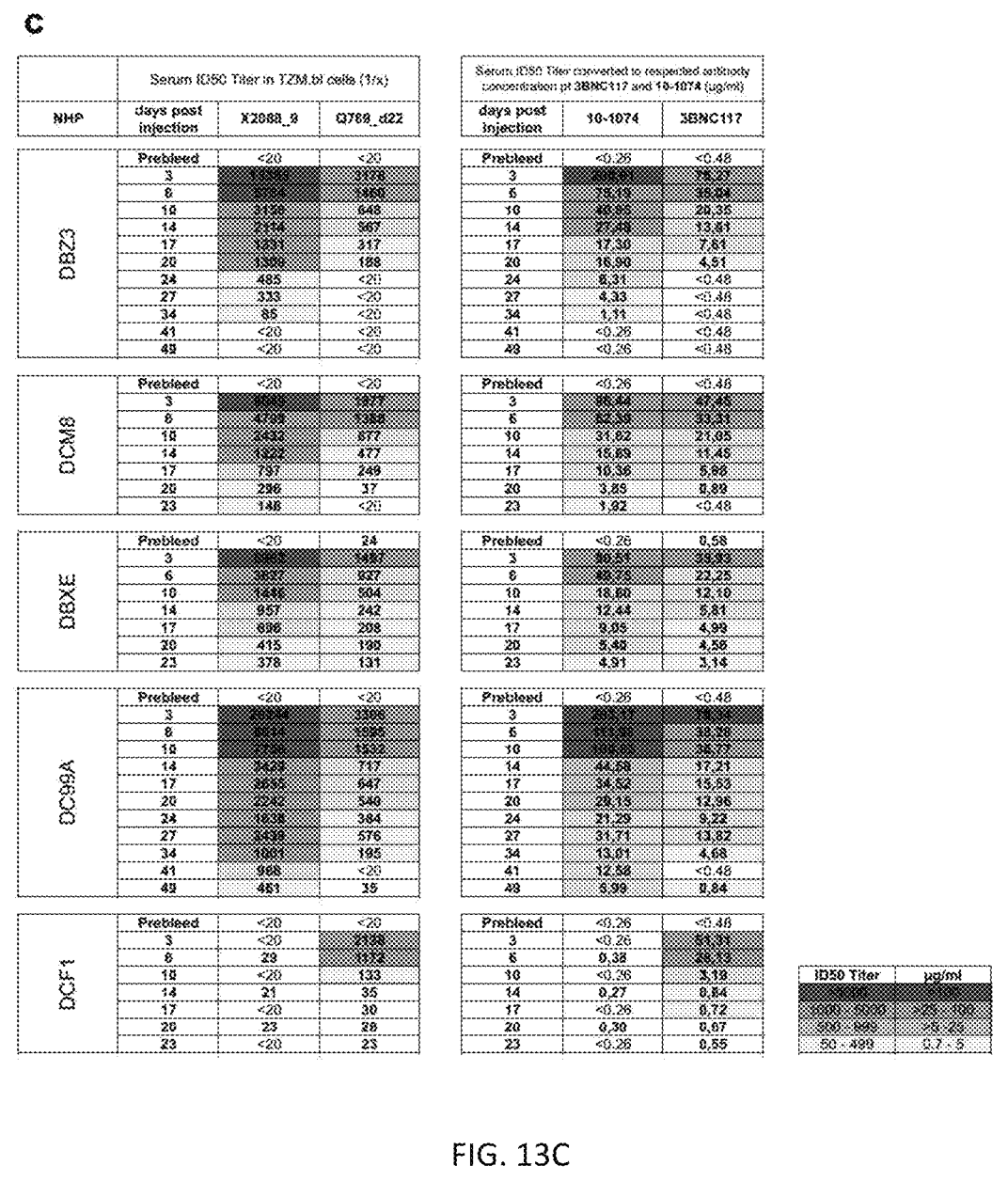

Plasma concentrations of each mAb were determined by measuring the plasma neutralizing activity against selected HIV-1 pseudovirus strains sensitive to one or the other, but not to both antibodies (FIG. 13A). In every treated animal, suppression of SHIVAD8EO viremia was maintained until a threshold plasma mAb concentration of approximately 1 to 3 μg/ml was reached (FIGS. 13B and 13C). This was even the case for macaque DCF1, for which a modest and transient reduction of plasma viral RNA levels was observed. Interestingly, the mAbs administered to clinically symptomatic macaques DCM8 and DCF1 had shortened half-lives or were undetectable. As noted earlier, macaque DCM8 had extremely low CD4+ T cell levels (43 cells/μl plasma) and macaque DCF1 had to be euthanized on day 56 post treatment initiation due to its deteriorating clinical condition. A necropsy of DCF1 revealed severe enteropathy, characterized by disseminated gastrointestinal cryptosporidiosis, pancreatitis, and cholangitis.

SGA analysis was used to determine whether amino acid substitutions had arisen in gp120 regions previously shown to affect the sensitivity to 10-1074 or 3BNC117 mAbs. In each case the rebound virus present in plasma following immunotherapy was unchanged. To further test the sensitivity of the re-emerging viruses, 10-1074 plus 3BNC117 combination therapy (10 mg/kg of each) was re-administered to the two clinically asymptomatic monkeys (DBZ3 and DC99A). The viral loads in each animal again rapidly fell, becoming undetectable at day 7 of the second immunotherapy cycle. Viremia was suppressed for 7 days in macaque DBZ3 and more than 21 days in monkey DC99A. Taken together, these results suggest that the re-emergence of virus following the first treatment cycle in these two animals represented insufficient mAb levels in vivo rather than antibody selected virus resistance.

TABLE 3

Repertoire of PGT121 and 10-1074 clonal variants

| pt10 mAB# | VH | DH | JH | CD43[1] | VHmut | Length[1] | (-) | (+) | Y | Lc | Vλ | Jλ | LCDR3[1] | Vλmut | FRW1_del | FRW3_Ins | Length[1] | (-) | (+) | Y |
|---|---|---|---|---|---|---|---|---|---|---|---|---|---|---|---|---|---|---|---|---|
| 10-160 | 4-59 | 3-3/16 | 6 | ARRGQRIYWVSFGEFFYYYSMDV | 49 | 24 | 2 | 3 | 4 | / | / | / | / | / | / | / | / | / | / | / |
| 10-186 | 4-59 | 3-3/16 | 6 | ARRGQRIYGVVSFGEFFYYYSMDV | 52 | 24 | 2 | 3 | 4 | λ | 3-21 | 3 | HMWDSRSGFSWS | 47 | 12 | 3 | 12 | 1 | 2 | 0 |
| 10-248 | 4-59 | 3-3/16 | 6 | ARRGQRIYGVVSSGEFFYYYSMDV | 46 | 24 | 2 | 3 | 4 | / | / | / | / | / | / | / | / | / | / | / |
| 10-295* | 4-59 | / | 6 | TKHGRRIYGIVAFNEWFTYFYMDV | 63 | 24 | 2 | 4 | 3 | λ | 3-21 | 3 | HIYDARGGTNWV | 58 | 21 | 3 | 12 | 1 | 2 | 1 |
| 10-266 | 4-59 | 3-3/16 | 6 | ARRGQRIYGVVSFGEFFYYYSMDV | 49 | 24 | 2 | 3 | 4 | λ | 3-21 | 3 | HMWDSRSGFSWS | 46 | 12 | 3 | 12 | 1 | 2 | 0 |
| 10-267 | 4-59 | / | 6 | AQQGKRIYGIVSFGELFYYYMDA | 58 | 24 | 2 | 2 | 5 | / | / | / | / | / | / | / | / | / | / | / |
| 10-303* | 4-59 | 3-3/9 | 6 | TLHGRRIYGIVAFNEWFTYFYMDV | 54 | 24 | 2 | 3 | 3 | λ | 3-21 | 3 | HIWDSRVPTKWV | 50 | 21 | 3 | 12 | 1 | 3 | 0 |
| 10-354 | 4-59 | 3-3/16 | 6 | ARRGQRIYGWSFGEFFYYYSMDV | 48 | 24 | 2 | 3 | 4 | / | / | / | / | / | / | / | / | / | / | / |
| 10-410* | 4-59 | 3-10/3 | 6 | ALHGKRIYGIVALGELFTYFYMDV | 63 | 24 | 2 | 3 | 3 | λ | 3-21 | 3 | HIWDSRRPTNWV | 44 | 21 | 3 | 12 | 1 | 3 | 0 |
| 10-416 | 4-59 | 3-3/16 | 6 | ARRGQRIYGVVSFGEFFYYYSMDV | 47 | 24 | 2 | 3 | 4 | λ | 3-21 | 3 | HMWDSRSGFSWS | 45 | 12 | 3 | 12 | 1 | 2 | 0 |
| 10-468 | 4-59 | 3-3/16 | 6 | ARRGQRIYGVVSFGEFFYYYSMDV | 47 | 24 | 2 | 3 | 4 | λ | 3-21 | 3 | HMWDSRSGFSWS | 46 | 12 | 3 | 12 | 1 | 2 | 0 |
| 10-543 | 4-59 | 3-10/3 | 6 | ALHGKRIYGIVALGELFTYFYMDV | 60 | 24 | 2 | 3 | 3 | / | / | / | / | / | / | / | / | / | / | / |
| 10-570 | 4-59 | 3-3/9 | 6 | ARRGQRIYGVVSFGEFFYYYSMDV | 42 | 24 | 2 | 3 | 4 | / | / | / | / | / | / | / | / | / | / | / |
| 10-621 | 4-59 | 3-3/9 | 6 | TLHGRRIYGIVAFNEWFTYFYMDV | 54 | 24 | 2 | 3 | 3 | / | / | / | / | / | / | / | / | / | / | / |
| 10-664 | 4-59 | 3-3/16 | 6 | ARRGQRIYGVVSFGEFFYYYSMDV | 47 | 24 | 2 | 3 | 4 | / | / | / | / | / | / | / | / | / | / | / |
| 10-720 | 4-59 | 3-3/16 | 6 | ARRGQRIYGVVSFGEFFYYYSMDV | 49 | 24 | 2 | 3 | 4 | / | / | / | / | / | / | / | / | / | / | / |
| 10-730 | 4-59 | 3-3/16 | 6 | ARRGQRIYGVVSFGEFFYYYSMDV | 48 | 24 | 2 | 3 | 4 | / | / | / | / | / | / | / | / | / | / | / |
| 10-814 | 4-59 | 3-10 | 6 | TQQGKRIYGVVSFGEFHYYYMDA | 43 | 24 | 2 | 3 | 4 | λ | 3-21 | 3 | HKWDSRSPLSWS | 52 | 15 | 3 | 12 | 1 | 3 | 0 |
| 10-847* | 4-59 | 3-3/16 | 6 | ARRGQRIYGVVSFGEFFYYYSMDV | 47 | 24 | 2 | 3 | 4 | λ | 3-21 | 3 | HMWDSRSGFSWS | 46 | 12 | 3 | 12 | 1 | 2 | 0 |
| 10-848 | 4-59 | 3-3/9 | 6 | TLHGRRIYGIVAFNEWFTYFYMDV | 55 | 24 | 2 | 3 | 3 | λ | 3-21 | 3 | HIWDSRVPTKWV | 46 | 21 | 3 | 12 | 1 | 3 | 0 |
| 10-996 | 4-59 | 3-3/10 | 6 | TQQGKRIYGVVSFGEFHYYYMDA | 41 | 24 | 2 | 3 | 4 | λ | 3-21 | 3 | HKWDSRSPLSWS | 50 | 15 | 3 | 12 | 1 | 2 | 0 |
| 10-1022 | 4-59 | 3-3 | 6 | ARRGQRIYGVVSFGEFFYYYSMDV | 51 | 24 | 2 | 3 | 4 | / | / | / | / | / | / | / | / | / | / | / |
| 10-1059 | 4-59 | 3-3/16 | 6 | TKHGRRIYGVVAFNEWFTYFYMDV | 59 | 24 | 2 | 4 | 3 | λ | 3-21 | 3 | HIYDARRPTNWV | 46 | 21 | 3 | 12 | 1 | 3 | 1 |

TABLE 3-continued

Repertoire of PGT121 and 10-1074 clonal variants

| pt10 mAB# | VH | DH | JH | CD43¹ | VHmut | Length¹ | (-) | (+) | Y | Lc Vλ | Jλ | LCDR3¹ | Vλmut | FRW1_del | FRW3_Ins | Length¹ | (-) | (+) | Y |
|---|---|---|---|---|---|---|---|---|---|---|---|---|---|---|---|---|---|---|---|
| 10-1074* | 4-59 | 3-3/16 | 6 | ARRGQRIYGVVSFGEFFYYYSMDV | 49 | 24 | 2 | 3 | 4 | λ | 3-21 | 3 | HMWDSRSGFSWS | 45 | 12 | 3 | 12 | 1 | 2 | 0 |
| 10-1121* | 4-59 | 3-10/3-3 | 6 | ALHGKRIYGIVALGELFTYFYMDV | 63 | 24 | 2 | 3 | 3 | λ | 3-21 | 3 | HIWDSRRPTNWV | 44 | 21 | 3 | 12 | 1 | 3 | 0 |
| 10-1130* | 4-59 | 3-10/3-3 | 6 | ALHGKRIYGIVALGELFTYFYMDV | 60 | 24 | 2 | 3 | 3 | λ | 3-21 | 3 | HIWDSRRPTNWV | 42 | 21 | 3 | 12 | 1 | 3 | 0 |
| 10-1141* | 4-59 | 3-10/3-3 | 6 | ALHGKRIYGIVALGELFTYFYMDV | 63 | 24 | 2 | 3 | 3 | λ | 3-21 | 3 | HIWDSRRPTNWV | 45 | 21 | 3 | 12 | 1 | 3 | 0 |
| 10-1145* | 4-59 | 3-10 | 6 | AQQGKRIYGIVSFGEFFYYYMDA | 58 | 24 | 2 | 2 | 5 | λ | 3-21 | 3 | HYWDSRSPISWV | 61 | 15 | 3 | 12 | 1 | 2 | 1 |
| 10-1151 | 4-59 | 3-3 | 6 | ARRGQRIYGVVSFGEFFYYYSMDV | 48 | 24 | 2 | 3 | 4 | λ | 3-21 | 3 | HMWDSRSGFSWS | 46 | 12 | 3 | 12 | 1 | 2 | 0 |
| 10-1167 | 4-59 | 3-3/16 | 6 | ARRGQRIYGVVSFGEFFYYYSMDV | 49 | 24 | 2 | 3 | 4 | / | / | 3 | / | / | / | 3 | / | / | / | / |
| 10-1223 | 4-59 | 3-3/16 | 6 | ARRGQRIYGVVSFGEFFYYYSMDV | 47 | 24 | 2 | 3 | 4 | λ | 3-21 | 3 | HMWDSRSGFSWS | 46 | 12 | 3 | 12 | 1 | 2 | 0 |
| 10-1232 | 4-59 | 3-10/3-3 | 6 | ALHGKRIYGIVALGELFTIFYMDV | 58 | 24 | 2 | 3 | 3 | λ | 3-21 | 3 | HIWDSRRPTNWV | 45 | 12 | 3 | 12 | 1 | 2 | 0 |
| 10-1263 | 4-59 | 3-3/16 | 6 | ARRGQRIYGVVSFGEFFYYYSMDV | 49 | 24 | 2 | 3 | 4 | λ | 3-21 | 3 | HMWDSRSGFSWS | 46 | 12 | 3 | 12 | 1 | 2 | 0 |
| 10-1294 | 4-59 | 3-3/16 | 6 | ARRGQRIYGVVSFGEFFYYYSMDV | 49 | 24 | 2 | 3 | 4 | λ | 3-21 | 3 | HMWDSRSGFSWS | 45 | 12 | 3 | 12 | 1 | 2 | 0 |
| 10-1341* | 4-59 | 3-3/16 | 6 | ARRGQRIYGVVSFGEFFYYYSMDV | 49 | 24 | 2 | 3 | 4 | λ | 3-21 | 3 | HMWDSRSGFSWS | 45 | 12 | 3 | 12 | 1 | 2 | 0 |
| 10-1342 | 4-59 | 3-3/16 | 6 | ARRGQRIYGVVSFGEFFYYYSMDV | 48 | 24 | 2 | 3 | 4 | λ | 3-21 | 3 | HMWDSRSGFSWS | 46 | 12 | 3 | 12 | 1 | 2 | 0 |
| 10-1369* | 4-59 | 3-3 | 6 | TKHGRRIYGVVAFGEWFTYFYMDV | 57 | 24 | 2 | 4 | 3 | λ | 3-21 | 3 | HIYDARRPTNWV | 43 | 21 | 3 | 12 | 1 | 3 | 1 |
| 10-1476 | 4-59 | 3-3/16 | 6 | ARRGQRIYGVVSFGEFFYYYSMDV | 47 | 24 | 2 | 3 | 4 | λ | 3-21 | 3 | HMWDSRSGFSWS | 46 | 12 | 3 | 12 | 1 | 2 | 0 |

VHmut and VλMut indicate the total number of mutations in the VH and VL Ig genes. (-) and (+) indicate the numbers of negatively and positively charged amino acids in the Ig complementary determining region (CDR3), respectively. Y indicated the number of Tyrosine residues in the IgH/L CDR3s. Based on Kabat nomenclature (IgBLAST). FRW1 del, number of deleted nucleotides in framework region 1 (FRW1) of the IgL. FRW3_ins, number of inserted nucleotides in framework region 3 (FRW3) of the IgL. Clonal members with identical IgH sequences are indicated and among them, IgL sequence identity that defines clones.
¹indicates the representative antibody variants that were produced and analyzed. 10-266 IgL was not cloned, and 10-1141 IgG was not produced.
*indicates the representative antibody variants that were produced and analyzed.

TABLE 4

In vitro TZM-bl neutralization assay on the basic pane

|  | 10-1369 | 10-259 | PGT121 | 10-303 | 10-410 | 10-1130 | 10-1121 | 10-1146 | 10-996 | 10-1341 | 10-847 | 10-1074 |
|---|---|---|---|---|---|---|---|---|---|---|---|---|
| $IC_{50}$ | | | | | | | | | | | | |
| BaL.26 | 0.069 | 0.021 | 0.021 | 0.045 | 0.016 | 0.013 | 0.046 | 0.064 | 0.045 | 0.032 | 0.022 | 0.033 |
| SS1196.1 | 0.033 | 0.012 | 0.008 | 0.015 | 0.008 | 0.008 | 0.029 | 0.027 | 0.007 | 0.011 | 0.006 | 0.010 |
| 6535.3 | 0.023 | 0.005 | 0.007 | 0.014 | 0.003 | 0.003 | 0.008 | 0.022 | 0.018 | 0.009 | 0.011 | 0.007 |
| QH0692.42 | 0.503 | 0.155 | 1.085 | 3.122 | 2.630 | 4.871 | 4.187 | 0.590 | 0.395 | 0.335 | 0.259 | 0.259 |
| TRJO4551.58 | 0.569 | 0.189 | 3.896 | 14.401 | 18.511 | 36.880 | 15.360 | 0.548 | 0.516 | 0.333 | 0.210 | 0.170 |
| SC422661.8 | 0.195 | 0.096 | 0.263 | 0.333 | 0.132 | 0.070 | 0.173 | 0.195 | 0.255 | 0.189 | 0.137 | 0.145 |
| PVO.4 | 0.225 | 0.175 | 0.147 | 0.670 | 0.494 | 0.385 | 0.570 | 0.310 | 0.211 | 0.236 | 0.172 | 0.178 |
| CAAN5342.A2 | 0.070 | 0.020 | 0.013 | 0.020 | 0.012 | 0.009 | 0.033 | 0.032 | 0.007 | 0.009 | 0.006 | 0.007 |
| YU-2 | 0.210 | 0.135 | 0.098 | 0.190 | 0.089 | 0.078 | 0.152 | 0.275 | 0.256 | 0.234 | 0.161 | 0.143 |
| R1166.c1 | >40 | >40 | >40 | >40 | >40 | >40 | >40 | >40 | >40 | >40 | >40 | >40 |
| MuLV | >40 | >40 | >40 | >40 | >40 | >40 | >40 | >40 | >40 | >40 | >40 | >40 |
| $IC_{80}$ | | | | | | | | | | | | |
| BaL.26 | 0.268 | 0.101 | 0.081 | 0.156 | 0.066 | 0.062 | 0.154 | 0.203 | 0.228 | 0.159 | 0.112 | 0.124 |
| SS1196.1 | 0.033 | 0.037 | 0.030 | 0.055 | 0.030 | 0.037 | 0.098 | 0.073 | 0.040 | 0.040 | 0.026 | 0.127 |
| 6535.3 | 0.060 | 0.022 | 0.041 | 0.053 | 0.021 | 0.013 | 0.033 | 0.078 | 0.085 | 0.038 | 0.044 | 0.044 |
| QH0692.42 | 1.714 | 0.551 | 14.976 | 18.122 | 12.071 | >40 | 21.943 | 1.993 | 1.404 | 1.100 | 0.908 | 0.861 |
| TRJO4551.58 | 3.818 | 0.965 | 26.930 | >40 | >40 | >40 | >23 | 2.604 | 4.265 | 1.226 | 0.768 | 0.693 |
| SC422661.8 | 0.940 | 0.333 | 0.714 | 1.156 | 0.449 | 0.264 | 0.741 | 0.663 | 0.845 | 0.501 | 0.386 | 0.392 |
| PVO.4 | 0.787 | 0.716 | 1.097 | 2.199 | 1.572 | 1.783 | 2.465 | 1.319 | 1.715 | 0.754 | 0.774 | 0.766 |
| CAAN5342.A2 | 0.186 | 0.063 | 0.056 | 0.092 | 0.055 | 0.045 | 0.095 | 0.088 | 0.060 | 0.054 | 0.035 | 0.044 |
| YU-2 | 0.738 | 0.382 | 0.356 | 0.502 | 0.243 | 0.313 | 0.340 | 0.750 | 0.891 | 0.766 | 0.537 | 0.398 |
| R1166.c1 | >40 | >40 | >40 | >40 | >40 | >40 | >23 | >40 | >40 | >40 | >40 | >40 |
| MuLV | >40 | >40 | >40 | >40 | >40 | >40 | >23 | >40 | >40 | >40 | >40 | >40 |

Numbers indicate antibody IgG concentrations in μg/ml to reach the $IC_{50}$ (top) and $IC_{80}$ (bottom) in the TZM-bl neutralization assay.
$IC_{50/80}$ values are indicated.
>indicates that the $IC_{50}$ for a given virus was not reached at the concentration tested.
Murine leukemia virus (MuLV) and R1166.c1 (clade AE) are negative controls.

TABLE 5

In vitro TZM-bl neutralization assay on the extended panel - IC50 values

| Virus ID | Clade | 10-996 | 10-1074 | PGT121 |
|---|---|---|---|---|
| 6535.3 | B | 0.017 | 0.014 | 0.008 |
| QH0692.42 | B | 0.396 | 0.191 | 1.041 |
| SC422661.8 | B | 0.173 | 0.091 | 0.101 |
| PVO.4 | B | 0.186 | 0.074 | 0.131 |
| TR0.11 | B | 0.012 | 0.008 | 0.005 |
| AC10.0.29 | B | 0.067 | 0.022 | 0.037 |
| RHPA4259.7 | B | 0.034 | 0.021 | 0.014 |
| THRO4156.18 | B | >50 | >50 | >50 |
| REJO4541.67 | B | >50 | >50 | 3.607 |
| TRJO4551.58 | B | 0.147 | 0.170 | 3.728 |
| WITO4160.33 | B | 0.538 | 0.185 | 0.459 |
| CAAN5342.A2 | B | 0.013 | 0.007 | 0.011 |
| YU-2 | B | 0.256 | 0.143 | 0.098 |
| WEAU_d15_410_787 | B(T/F) | 0.147 | 0.104 | 0.083 |
| 1006_11_C3_1601 | B(T/F) | 0.001 | 0.003 | 0.008 |
| 1054_07_TC4_1499 | B(T/F) | 0.260 | 0.129 | 0.115 |
| 1056_10_TA11_1826 | B(T/F) | 0.117 | 0.038 | 0.066 |
| 1012_11_TC21_3257 | B(T/F) | 0.018 | 0.008 | 0.008 |
| 6240_08_TA5_4622 | B(T/F) | 0.095 | 0.068 | 0.128 |
| 6244_13_B5_4576 | B(T/F) | 0.353 | 0.202 | 0.249 |
| 62357_14_D3_4589 | B(T/F) | 23.300 | >50 | 1.036 |
| SC05_8C11_2344 | B(T/F) | 0.069 | 0.052 | 0.093 |
| Du156.12 | C | 0.018 | 0.015 | 0.007 |
| Du172.17 | C | 0.173 | 0.121 | 0.115 |
| Du422.1 | C | 0.056 | 0.045 | 0.029 |
| ZM197M.PB7 | C | >50 | >50 | >50 |
| ZM214M.PL15 | C | 0.413 | 0.174 | 0.236 |
| ZM233M.PB6 | C | | 0.060 | 1.451 |
| ZM249M.PL1 | C | >50 | >50 | >50 |
| ZM53M.PB12 | C | >50 | >50 | <0.001 |
| ZM109F.PB4 | C | >50 | >50 | 7.894 |
| ZM135M.PL10a | C | 0.099 | 0.069 | 0.576 |
| CAP45.2.00.G3 | C | >50 | >50 | 0.086 |
| CAP210.2.00.E8 | C | 24.793 | >50 | 5.082 |
| HIV-001428-2.42 | C | 0.040 | 0.044 | 0.028 |
| HIV-0013095-2.11 | C | 31.531 | >50 | >50 |
| HIV-16055-2.3 | C | >50 | >50 | 0.444 |
| HIV-16845-2.22 | C | 1.325 | 1.169 | 12.685 |
| Ce1086_B2 | C(T/F) | >50 | >50 | <0.001 |
| Ce0393_C3 | C(T/F) | >50 | >50 | >50 |
| Ce1176_A3 | C(T/F) | 0.043 | 0.018 | 0.017 |
| Ce2010_F5 | C(T/F) | >50 | >50 | >50 |
| Ce0682_E4 | C(T/F) | >50 | >50 | >50 |
| Ce1172_H1 | C(T/F) | 0.058 | 0.047 | 0.023 |
| Ce2060_G9 | C(T/F) | >50 | >50 | >50 |
| Ce703010067_2A2 | C(T/F) | >50 | >50 | >50 |
| BF1266.431a | C(T/F) | >50 | >50 | >50 |
| 246F C1G | C(T/F) | 0.092 | 0.022 | 0.083 |
| 249M B10 | C(T/F) | >50 | >50 | >50 |
| ZM247v1(Rev-) | C(T/F) | 0.055 | 0.042 | 0.027 |
| 7030102001E5(Rev-) | C(T/F) | 0.013 | 0.006 | 0.010 |
| 1394C9G1(Rev-) | C(T/F) | 0.086 | 0.050 | 0.486 |
| Ce704809221_1B3 | C(T/F) | 0.243 | 0.139 | 0.098 |
| CNE19 | BC | 3.452 | 50.000 | 0.018 |
| CNE20 | BC | <0.001 | <0.001 | 0.002 |
| CNE21 | BC | 0.086 | 0.087 | 0.020 |
| CNE17 | BC | 4.040 | 2.686 | 45.289 |
| CNE30 | BC | 0.614 | 0.363 | 0.101 |
| CNE52 | BC | 4.525 | 1.226 | 3.741 |
| CNE53 | BC | 0.057 | 0.039 | 0.055 |
| CNE58 | BC | 0.570 | 0.267 | >50 |
| MS208.A1 | A | >50 | >50 | >50 |
| Q23.17 | A | 0.008 | 0.006 | 0.010 |
| Q451.e2 | A | >50 | >50 | >50 |
| Q259.d2.17 | A | >50 | >50 | 8.990 |
| Q769.d22 | A | >50 | >50 | >50 |
| Q842.d12 | A | >50 | >50 | 0.023 |
| 3415.v1.c1 | A | 35.876 | >50 | >50 |
| 3365.v2.c2 | A | 0.286 | 0.131 | 0.921 |
| 0260.v5.c36 | A | 0.160 | 0.099 | 0.054 |

TABLE 5-continued

In vitro TZM-bl neutralization assay on the extended panel - IC50 values

| Virus ID | Clade | 10-996 | 10-1074 | PGT121 |
|---|---|---|---|---|
| 191955_A11 | A (T/F) | >50 | >50 | >50 |
| 191084 B7-19 | A (T/F) | 0.057 | 0.032 | 0.042 |
| 9004SS_A3_4 | A (T/F) | 0.012 | 0.011 | 0.008 |
| T257-31 | CRF02_AG | >50 | >50 | >50 |
| 928-28 | CRF02_AG | 1.331 | 0.847 | >50 |
| 263-8 | CRF02_AG | 10.919 | 0.666 | 3.347 |
| T250-4 | CRF02_AG | <0.001 | <0.001 | 0.001 |
| T251-18 | CRF02_AG | 0.939 | 1.081 | >50 |
| T278-50 | CRF02_AG | 14.010 | 2.146 | >50 |
| T255-34 | CRF02_AG | 28.369 | >50 | 6.725 |
| 211-9 | CRF02_AG | 0.750 | 0.112 | 1.455 |
| 235-47 | CRF02_AG | 0.128 | 0.050 | 0.332 |
| 620345.c01 | CRF01_AE | >50 | >50 | >50 |
| CNE8 | CRF01_AE | >50 | >50 | >50 |
| C1080.c03 | CRF01_AE | >50 | >50 | >50 |
| R2184.c04 | CRF01_AE | >50 | >50 | >50 |
| R1166.c01 | CRF01_AE | >50 | >50 | >50 |
| C2101.c01 | CRF01_AE | >50 | >50 | >50 |
| C3347.c11 | CRF01_AE | >50 | >50 | >50 |
| C4118.c09 | CRF01_AE | >50 | >50 | >50 |
| CNE5 | CRF01_AE | >50 | >50 | >50 |
| BJOX009000.02.4 | CRF01_AE | >50 | >50 | 3.626 |
| BJOX015000.11.5 | CRF01_AE(T/F) | >50 | >50 | >50 |
| BJOX010000.06.2 | CRF01_AE(T/F) | >50 | >50 | >50 |
| BJOX025000.01.1 | CRF01_AE(T/F) | >50 | >50 | >50 |
| BJOX028000.10.3 | CRF01_AE(T/F) | >50 | >50 | >50 |
| X1193_c1 | G | 0.144 | 0.083 | 0.045 |
| P04S2_c2_11 | G | 0.022 | 0.012 | 0.020 |
| X1254_c3 | G | 0.121 | 0.089 | 0.056 |
| X2088_c9 | G | 0.002 | 0.003 | 0.011 |
| X2131_C1_85 | G | 0.019 | 0.016 | 0.015 |
| P1981_C5_3 | G | 0.005 | 0.005 | 0.004 |
| X1632_S2_B10 | G | >50 | >50 | >50 |
| 3016.v5.c45 | D | >50 | >50 | >50 |
| A07412M1.vrc12 | D | 0.008 | <0.001 | 0.001 |
| 231965.c01 | D | >50 | >50 | >50 |
| 231966.c02 | D | >50 | >50 | >50 |
| 191821_E6_1 | D(T/F) | >50 | >50 | >50 |
| 3817.v2.c59 | CD | 8.147 | 3.148 | >50 |
| 6480.v4.c25 | CD | 0.010 | 0.009 | 0.017 |
| 6952.v1.c20 | CD | 0.044 | 0.037 | 0.085 |
| 6811.v7.c18 | CD | 0.001 | 0.002 | 0.004 |
| 89-F1_2_25 | CD | >50 | >50 | >50 |
| 3301.v1.c24 | AC | 0.016 | 0.013 | 0.014 |
| 6041.v3.c23 | AC | >50 | >50 | >50 |
| 6540.v4.c1 | AC | >50 | >50 | >50 |
| 6545.v4.c1 | AC | >50 | >50 | >50 |
| 0815.v3.c3 | ACD | 0.061 | 0.030 | 0.022 |
| 3103.v3.c10 | ACD | 0.053 | 0.037 | 0.042 |

Numbers indicate antibody IgG concentrations in μg/ml to reach the IC$_{50}$ in the TZM-bl neutralization assay.
IC50 values indicate increasing neutralization sensitivity.
>indicates that the IC$_{50}$ for a given virus was not reached at the concentration tested.

TABLE 6

In vitro TZM-bl neutralization assay on the extended panel - IC80

| Virus ID | Clade | 10-996 | 10-1074 | PGT121 |
|---|---|---|---|---|
| 6535.3 | B | 0.046 | 0.026 | 0.021 |
| QH0692.42 | B | 1.854 | 0.929 | 8.545 |
| SC422661.8 | B | 0.627 | 0.418 | 0.460 |
| PVO.4 | B | 0.952 | 0.360 | 0.945 |
| TR0.11 | B | 0.081 | 0.057 | 0.051 |
| AC10.0.29 | B | 0.250 | 0.110 | 0.169 |
| RHPA4259.7 | B | 0.163 | 0.118 | 0.054 |
| THRO4156.18 | B | >50 | >50 | >50 |
| REJO4541.67 | B | >50 | >50 | >50 |
| TRJO4551.58 | B | 7.269 | 0.634 | 35.291 |
| WITO4160.33 | B | 6.484 | 2.112 | 6.007 |
| CAAN5342.A2 | B | 0.079 | 0.036 | 0.051 |
| YU-2 | B | 0.891 | 0.398 | 0.356 |
| WEAU_d15_410_787 | B (T/F) | 0.422 | 0.375 | 0.295 |
| 1006_11_C3_1601 | B (T/F) | 0.019 | 0.013 | 0.023 |
| 1054_07_TC4_1499 | B (T/F) | 0.901 | 0.583 | 0.696 |
| 1054_10_TA11_1826 | B (T/F) | 0.563 | 0.272 | 0.303 |
| 1012_11_TC21_3257 | B (T/F) | 0.111 | 0.059 | 0.038 |
| 6240_08_TA5_4622 | B (T/F) | 0.348 | 0.306 | 0.584 |
| 6244_13_B5_4576 | B (T/F) | 1.296 | 0.922 | 1.878 |
| 62357_14_D3_4589 | B (T/F) | >50 | >50 | 45.559 |
| SC05_8C11_2344 | B (T/F) | 0.174 | 0.123 | 0.275 |
| Du156.12 | C | 0.101 | 0.076 | 0.033 |
| Du172.17 | C | 0.607 | 0.430 | 0.890 |
| Du422.1 | C | 0.215 | 0.166 | 0.131 |
| ZM197M.PB7 | C | >50 | >50 | >50 |
| ZM214M.PL15 | C | 3.251 | 2.367 | 3.150 |
| ZM233M.PB6 | C | 4.524 | 0.349 | 8.977 |
| ZM249M.PL1 | C | >50 | >50 | >50 |
| ZM53M.PB12 | C | >50 | >50 | 0.002 |
| ZM109F.PB4 | C | >50 | >50 | >50 |
| ZM135M.PL10a | C | 0.553 | 0.367 | 5.885 |
| CAP45.2.00.G3 | C | >50 | >50 | 6.544 |
| CAP210.2.00.E8 | C | >50 | >50 | >50 |
| HIV-001428-2.42 | C | 0.204 | 0.281 | 0.156 |
| HIV-0013095-2.11 | C | >50 | >50 | >50 |
| HIV-16055-2.3 | C | >50 | >50 | 4.290 |
| HIV-16845-2.22 | C | 9.933 | 5.835 | >50 |
| Ce1086_B2 | C (T/F) | >50 | >50 | 0.006 |
| Ce0393_C3 | C (T/F) | >50 | >50 | >50 |
| Ce1176_A3 | C (T/F) | 0.151 | 0.070 | 0.058 |
| Ce2010_F5 | C (T/F) | >50 | >50 | >50 |
| Ce0682_E4 | C (T/F) | >50 | >50 | >50 |
| Ce1172_H1 | C (T/F) | 0.173 | 0.166 | 0.088 |
| Ce2060_G9 | C (T/F) | >50 | >50 | >50 |
| Ce703910054_2A2 | C (T/F) | >50 | >50 | >50 |
| BF1266.431a | C (T/F) | >50 | >50 | >50 |
| 246F C1G | C (T/F) | 0.270 | 0.111 | 0.287 |
| 249M B10 | C (T/F) | >50 | >50 | >50 |
| 2M247v1(Rev-) | C (T/F) | 0.252 | 0.186 | 0.126 |
| 7030102001E5(Rev-) | C (T/F) | 0.044 | 0.021 | 0.043 |
| 1394C9G1(Rev-1) | C (T/F) | 0.328 | 0.191 | 3.372 |
| Ce704809221_1B3 | C (T/F) | 1.208 | 0.696 | 0.492 |
| CNE19 | BC | >50 | >50 | 0.189 |
| CNE20 | BC | <0.001 | 0.005 | 0.008 |
| CNE21 | BC | 0.255 | 0.181 | 0.061 |
| CNE17 | BC | 24.701 | 13.297 | >50 |
| CNE30 | BC | 1.989 | 1.200 | 0.559 |
| CNE52 | BC | 43.834 | 13.147 | 32.935 |
| CNE53 | BC | 0.233 | 0.141 | 0.200 |
| CNE58 | BC | 2.220 | 0.968 | >50 |
| MS208.A1 | A | >50 | >50 | >50 |
| Q23.17 | A | 0.030 | 0.021 | 0.031 |
| Q451.e2 | A | >50 | >50 | >50 |
| Q769.d22 | A | >50 | >50 | >50 |
| Q259.d2.17 | A | >50 | >50 | >50 |
| Q842.d12 | A | >50 | >50 | 0.074 |
| 3415.v1.c1 | A | >50 | >50 | >50 |
| 3365.v2.c2 | A | 1.380 | 0.450 | 7.353 |
| 0260.v5.c36 | A | 0.436 | 0.160 | 0.152 |
| 191955_A11 | A (T/F) | >50 | >50 | >50 |
| 191084 B7-19 | A (T/F) | 0.144 | 0.128 | 0.128 |
| 9004SS_A3_4 | A (T/F) | 0.050 | 0.030 | 0.026 |
| T257-31 | CRF02_AG | >50 | >50 | >50 |
| 928-28 | CRF02_AG | 7.151 | 4.696 | >50 |
| 263-8 | CRF02_AG | >50 | 6.527 | 24.576 |
| T250-4 | CRF02_AG | 0.005 | 0.005 | 0.011 |
| T251-18 | CRF02_AG | 7.399 | 7.395 | >50 |
| T278-50 | CRF02_AG | >50 | 18.276 | >50 |
| T255-34 | CRF02_AG | >50 | >50 | >50 |
| 211-9 | CRF02_AG | 3.848 | 0.425 | 8.840 |
| 235-47 | CRF02_AG | 0.381 | 0.163 | 1.676 |
| 620345.c01 | CRF01_AE | >50 | >50 | >50 |
| CNE8 | CRF01_AE | >50 | >50 | >50 |
| C1080.c03 | CRF01_AE | >50 | >50 | >50 |
| R2184.c04 | CRF01_AE | >50 | >50 | >50 |
| R1166.c01 | CRF01_AE | >50 | >50 | >50 |
| C2101.c01 | CRF01_AE | >50 | >50 | >50 |
| C3347.c11 | CRF01_AE | >50 | >50 | >50 |

TABLE 6-continued

In vitro TZM-bl neutralization assay on the extended panel - IC80

| Virus ID | Clade | 10-996 | 10-1074 | PGT121 |
|---|---|---|---|---|
| C4118.c09 | CRF01_AE | >50 | >50 | >50 |
| CNE5 | CRF01_AE | >50 | >50 | >50 |
| BJOX009000.02.4 | CRF01_AE | >50 | >50 | 37.289 |
| BJOX015000.11.5 | CRF01_AE(T/F) | >50 | >50 | >50 |
| BJOX010000.06.2 | CRF01_AE(T/F) | >50 | >50 | >50 |
| BJOX025000.01.1 | CRF01_AE(T/F) | >50 | >50 | >50 |
| BJOX028000.10.3 | CRF01_AE(T/F) | >50 | >50 | >50 |
| X1193_c1 | G | 0.482 | 0.475 | 0.202 |
| P0402_c2_11 | G | 0.065 | 0.039 | 0.056 |
| X1254_c3 | G | 0.420 | 0.297 | 0.199 |
| X2088_c9 | G | 0.014 | 0.014 | 0.029 |
| X2131_C1_B5 | G | 0.085 | 0.064 | 0.058 |
| P1981_C5_3 | G | 0.018 | 0.017 | 0.015 |
| X1632_S2_B10 | G | >50 | >50 | >50 |
| 3016.v5.c45 | D | >50 | >50 | >50 |
| A07412M1.vrc12 | D | 0.070 | 0.048 | 0.406 |
| 231965.c01 | D | >50 | >50 | >50 |
| 231966.c02 | D | >50 | >50 | >50 |
| 191821_E6_1 | D(T/F) | >50 | >50 | >50 |
| 3817.v2.c59 | CD | 34.619 | 14.880 | >50 |
| 6480.v4.c25 | CD | 0.049 | 0.041 | 0.079 |
| 6952.v1.c20 | CD | 0.188 | 0.138 | 0.605 |
| 6811.v7.c.18 | CD | 0.011 | 0.010 | 0.017 |
| 89-F1_2_25 | CD | >50 | >50 | >50 |
| 3301.v1.c24 | AC | 0.054 | 0.042 | 0.043 |
| 6041.v3.c23 | AC | >50 | >50 | >50 |
| 6540.v4.c1 | AC | >50 | >50 | >50 |
| 6545.v4.c1 | AC | >50 | >50 | >50 |
| 0815.v3.c3 | ACD | 0.251 | 0.138 | 0.105 |
| 3103.v3.c10 | ACD | 0.150 | 0.101 | 0.110 |

Numbers indicate antibody IgG concentrations in µg/ml to reach the $IC_{80}$ in the TZM-bl enuralization assay.
$IC_{80}$ values indicate neutralization sensitivity.
>indicates tahtthe $IC_{80}$ for a given virus was not reached at the concentration tested.

Figure 14:
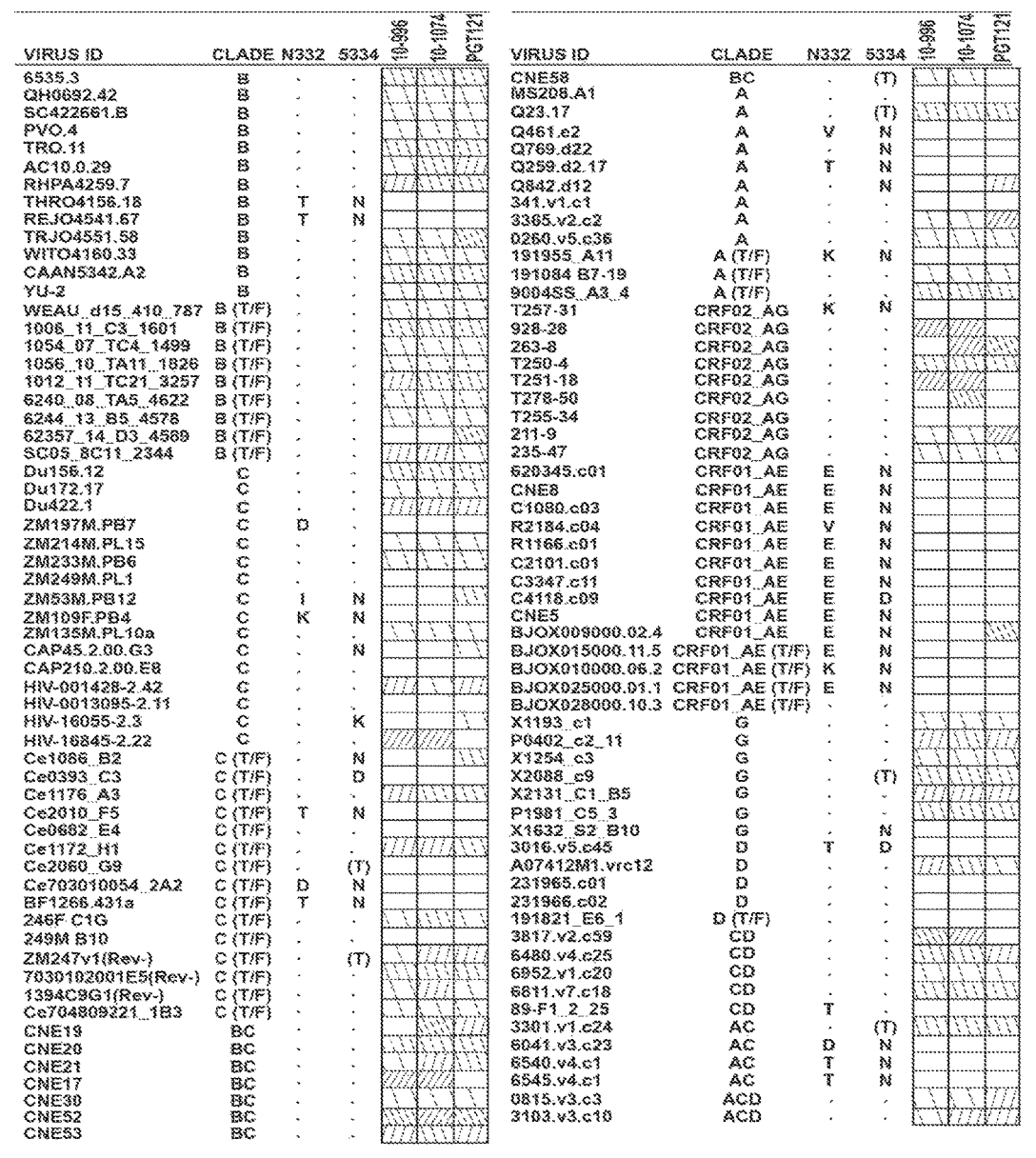

Table 7 Neutralization sensitivity according to N332 PNGS (shown in FIG. 14).

TABLE 8

In vitro PBMC-based neutralization assay

| | Virus ID | 3BNC55 | 3BNC60 | 3BNC117 | 3BNC134 | 1NC9 | 45-46 | 3BNC195 | 12A12 | 4E10 | b12 |
|---|---|---|---|---|---|---|---|---|---|---|---|
| CONTEMPORARY HISTORICAL | P035.6.EA | 1.918 | 0.023 | <0.0032 | 0.034 | 0.451 | 0.037 | >50 | 0.110 | 1.043 | 11.865 |
| | P035.6.H11 | 0.550 | 0.029 | 0.022 | 0.239 | 0.031 | 0.053 | >50 | 0.130 | 2.941 | 10.758 |
| | P035.6.D10 | >50 | >50 | 0.019 | >50 | 0.248 | <0.0032 | >50 | <0.0032 | 0.792 | >12.5 |
| | P151.37.C7 | 0.084 | 0.038 | 0.053 | 0.128 | 0.018 | 0.016 | 0.133 | 0.402 | 2.941 | 1.882 |
| | P151.37.F1 | 1.297 | 0.125 | 0.161 | 1.633 | 1.288 | 0.203 | 0.136 | 18.043 | 0.860 | >12.5 |
| | P151.37.F10 | 3.770 | 0.311 | 0.249 | 4.661 | >50 | 0.375 | >50 | 18.883 | 9.314 | 0.452 |
| | P153.10.2.A9 | 15.804 | 0.763 | 0.861 | 17.208 | 46.735 | 0.069 | 0.201 | >50 | 12.269 | 7.988 |
| | P153.10.2.D8 | 20.568 | 1.020 | 0.206 | 23.124 | >50 | 0.030 | >50 | 2.478 | 0.861 | >12.5 |
| | P153.10.2.E10 | 1.226 | 0.546 | 0.211 | 2.105 | >50 | 0.108 | >50 | 10.686 | 0.792 | 9.212 |
| | P186.12.1.D10 | 0.061 | 0.061 | 0.105 | >50 | 0.075 | 0.165 | 0.091 | 7.288 | >25 | 9.333 |
| | P186.12.1.F4 | >50 | >50 | >50 | >50 | >50 | >50 | >50 | >50 | 4.903 | 11.075 |
| | P186.12.1.G2 | 1.890 | <0.0032 | <0.0032 | >50 | 0.046 | 0.017 | >50 | 0.068 | 15.711 | 10.763 |
| | P195.31.A6 | 0.032 | 0.138 | <0.0032 | 0.171 | 0.228 | 0.052 | 0.099 | 0.206 | 2.934 | 0.498 |
| | P195.31.A10 | 0.252 | 0.024 | 0.025 | >50 | 0.953 | 0.050 | 0.071 | >50 | 1.248 | 9.896 |
| | P195.31F11 | 0.569 | 0.084 | 0.137 | >50 | >50 | 0.076 | >50 | 33.131 | 2.301 | >12.5 |
| | P019.1.D2 | 0.949 | 0.164 | 0.027 | >50 | >50 | 0.057 | >50 | 14.612 | >25 | 0.432 |
| | P019.1.D8 | 3.122 | 0.738 | 0.635 | >50 | >50 | 5.767 | >50 | >50 | 2.443 | >12.5 |
| | P019.1.G7 | 6.034 | 3.636 | 4.570 | >50 | >50 | 6.962 | >50 | 20.092 | 1.073 | >12.5 |
| | P175.10.D7 | 2.539 | 0.936 | 3.588 | >50 | 42.695 | 17.723 | >50 | 35.805 | 1.187 | 1.369 |
| | P175.10.D12 | 0.708 | 0.410 | 0.067 | >50 | 0.317 | 0.175 | 1.233 | 10.648 | 0.953 | >12.5 |
| | P175.10.G10 | 2.508 | 0.563 | 0.621 | >50 | 33.008 | 8.364 | 22.413 | 18.554 | 1.147 | >12.5 |
| | P013.18.A9 | 0.125 | 0.102 | 0.079 | >50 | 0.198 | 0.018 | 0.426 | 0.205 | 0.786 | >12.5 |
| | P154.44.C8 | >50 | 0.683 | 1.042 | >50 | >50 | 16.440 | 0.925 | >50 | >25 | >12.5 |
| | P154.44.G8 | >50 | 1.220 | 2.172 | >50 | >50 | 25.616 | 1.969 | >50 | 4.450 | >12.5 |
| | P183.50.2.H3 | 2.197 | 0.116 | 0.1212 | 12.049 | 4.079 | 0.161 | >50 | 0.476 | 3.890 | 5.923 |
| | P183.3.2.B9 | 0.076 | 0.025 | <0.0032 | 0.053 | 0.326 | 0.142 | >50 | 0.472 | 1.722 | 1.230 |
| | P001.35.F5 | 0.418 | 0.046 | 0.047 | 8.133 | 0.329 | 0.133 | >50 | 0.197 | >0.39 | >12.5 |
| | P001.35.H4 | 2.180 | 0.333 | 1.919 | >50 | >50 | 6.118 | >50 | >50 | 0.830 | >12.5 |
| | P002.39.CB | 15.016 | 0.117 | 0.172 | 2.192 | 12.154 | 0.546 | >50 | >50 | 1.955 | >12.5 |
| | P002.39.FB | >50 | 28.891 | >50 | 13.090 | >50 | 0.404 | >50 | >50 | 0.864 | >12.5 |
| | P002.39.H10 | 1.472 | 0.785 | 0.726 | 14.160 | 1.147 | 0.017 | >50 | >50 | 1.530 | >12.5 |
| | P034.6.D6 | 37.003 | 0.161 | 0.126 | 11.339 | 1.137 | 0.235 | >50 | 0.802 | 1.164 | 11.122 |
| | P034.6.G10 | 48.877 | 0.348 | 0.237 | 22.481 | 1.428 | 0.017 | >50 | 0.186 | 0.820 | 8.598 |
| | P034.6.H5 | >50 | 0.417 | 0.267 | 20.730 | 0.820 | 0.245 | >50 | 0.866 | 0.391 | >12.5 |
| | P101.20.1.F1 | >50 | >50 | >50 | >50 | >50 | 0.565 | >50 | 0.634 | 3.999 | >12.5 |
| | P101.20.1.HB | >50 | >50 | >50 | >50 | >50 | 0.090 | >50 | 0.474 | 1.902 | >12.5 |
| | P127.46.A6 | >50 | >50 | >50 | >50 | >50 | 0.386 | >50 | 0.666 | 1.211 | 6.780 |
| | P127.46.D1 | 1.242 | 0.024 | 0.043 | 5.403 | 2.558 | 0.169 | >50 | 0.227 | 1.092 | >12.5 |
| | P127.46.D2 | 1.125 | 0.173 | 0.221 | >50 | 2.231 | 0.279 | >50 | 0.494 | 1.613 | <0.195 |
| | P174.28.E11 | 2.399 | 0.483 | 0.716 | >50 | 13.061 | 0.894 | >50 | 2.104 | 2.113 | 8.149 |
| | P177.25.1.G9 | 0.980 | 0.191 | 0.189 | >50 | 1.826 | 0.261 | >50 | 0.130 | 1.665 | >12.5 |
| | P177.25.2.B4 | 1.179 | 0.080 | 0.041 | 23.609 | 0.384 | 0.150 | >50 | 0.028 | 3.729 | >12.5 |
| | P177.25.2.D1 | >50 | 1.949 | 1.359 | >50 | 46.825 | 11.454 | >50 | 7.681 | 1.140 | 7.770 |
| | P180.14.A6 | 1.389 | 0.098 | 0.058 | 0.017 | >50 | 0.024 | >50 | 0.022 | 1.162 | >12.5 |
| | P180.14.G6 | 45.246 | 0.116 | 0.122 | 2.449 | 13.361 | 0.169 | 0.220 | 0.093 | 4.009 | >12.5 |
| | P180.14.G7 | 23.444 | 0.052 | 0.035 | 0.022 | 1.450 | 0.024 | 0.703 | 0.729 | 15.759 | >12.5 |
| | P197.25.1.D2 | >50 | 0.285 | 0.194 | 1.480 | 1.137 | 0.016 | 0.028 | 0.072 | 1.492 | >12.5 |
| | P197.25.1.D7 | >50 | 0.782 | 0.019 | 0.052 | 7.058 | 0.051 | 0.016 | 2.601 | 0.948 | >12.5 |

TABLE 8-continued

In vitro PBMC-based neutralization assay

| | | | | | | | | | | |
|---|---|---|---|---|---|---|---|---|---|---|
| P197.25.1.H1 | >50 | 0.017 | 0.019 | <0.0032 | <0.0032 | 0.029 | <0.0032 | 0.754 | 2.515 | >12.5 |
| P405.18.D3 | 0.068 | <0.0032 | 0.029 | 0.095 | 0.048 | 0.022 | 0.022 | 0.031 | 0.924 | 0.471 |
| P405.18.F10 | 0.936 | 0.063 | 0.084 | 5.646 | 0.432 | 0.094 | 0.126 | 0.469 | 1.350 | 0.716 |
| P405.18.H5 | 4.726 | 0.219 | 0.782 | 1.100 | 19.220 | 0.027 | 0.450 | 43.684 | 1.328 | 0.497 |
| P405.19.A8 | 0.291 | 0.021 | <0.0032 | 0.116 | 0.278 | 0.059 | 0.110 | 0.034 | 2.012 | 1.116 |
| P405.19.B12 | 0.889 | 0.057 | 0.098 | 0.264 | 1.103 | 0.033 | 0.233 | 0.157 | 0.807 | 0.656 |
| P405.19.F11 | 0.689 | 0.018 | 0.109 | 2.892 | 2.131 | 0.037 | >50 | 5.279 | 0.818 | 0.413 |
| 1140.6F5 | 0.328 | 0.029 | <0.0032 | 5.219 | 6.915 | 0.284 | >50 | 13.917 | 21.480 | >25 |
| 1170.6G9 | 0.748 | 0.116 | 0.114 | 4.222 | 0.096 | 0.147 | >50 | 0.220 | 6.710 | 3.270 |
| P116.2 | 5.406 | 0.493 | 0.422 | 40.937 | 5.647 | 0.142 | >50 | 17.250 | 16.580 | 17.370 |
| P116.3.F6 | 22.297 | 0.235 | 0.255 | 0.495 | 0.728 | 0.158 | >50 | 15.152 | 9.520 | 13.540 |
| P116.3.G9 | 1.054 | 0.071 | 0.018 | 0.435 | 3.157 | 1.385 | 0.540 | 24.689 | 5.750 | 0.650 |
| P116.4.11 | 2.594 | 0.149 | 0.353 | 17.822 | 6.646 | 0.703 | 0.329 | 26.982 | 13.790 | 3.120 |
| 1234.3A9 | 2.623 | 0.226 | 0.032 | 15.504 | 3.944 | 0.815 | 0.062 | 40.940 | 24.600 | >25 |
| 1234.3D9 | 0.563 | 0.102 | 0.057 | 4.784 | 0.539 | 0.087 | 0.178 | 48.779 | 15.780 | >25 |
| 658.8A6 | 4.860 | 0.355 | 0.386 | >50 | 2.057 | 0.379 | 0.196 | 31.416 | >25 | >25 |
| 658.8D2 | 2.832 | 0.264 | 0.201 | 40.617 | 1.651 | 0.347 | 0.197 | 3.291 | >25 | 2.000 |
| 658.8F8 | <0.0032 | <0.0032 | <0.0032 | >0.0032 | 0.994 | 0.142 | >50 | 0.018 | >25 | >25 |
| 526.17-2C11 | <0.0032 | 0.032 | 0.040 | 0.028 | 0.048 | 0.123 | >50 | 0.049 | ND | ND |
| 526.17-2G1 | 0.429 | 0.141 | 0.025 | <0.0032 | 5.002 | 0.962 | >50 | 0.353 | ND | ND |
| 526.17-2G3 | 2.825 | 0.170 | 0.120 | 4.692 | 0.687 | 0.110 | >50 | 0.928 | ND | ND |
| 424.9F4 | 0.065 | 0.091 | 0.016 | 0.589 | 2.534 | 0.508 | >50 | 2.757 | ND | ND |
| 424.9H1 | 17.101 | 1.386 | 1.114 | 19.990 | 4.508 | 0.590 | >50 | 4.982 | ND | ND |
| 139.19A6 | >50 | 1.059 | 1.091 | 3.132 | >50 | 0.090 | >50 | 0.520 | ND | ND |
| 139.19.C10 | >50 | 0.118 | 0.089 | 5.745 | >50 | 0.019 | >50 | 0.093 | ND | ND |
| 139.19.F2 | >50 | 0.241 | 0.226 | 0.755 | 11.125 | 0.038 | >50 | 0.525 | ND | ND |
| 208.9.C6 | 17.496 | 0.375 | 0.587 | 25.217 | 1.510 | 0.587 | 0.123 | >50 | ND | ND |
| 208.9.F12 | 5.263 | 0.265 | 0.314 | 11.871 | 4.460 | 0.414 | 0.234 | >50 | ND | ND |
| 208.9.G10 | 6.842 | 0.151 | 0.351 | 2.896 | 2.099 | 0.832 | 0.093 | >50 | ND | ND |
| 1031.12.6C4 | 0.701 | 0.024 | 0.089 | 0.321 | 9.717 | 0.057 | >50 | >50 | 17.730 | 1.180 |
| 1031.12.7D5 | 0.140 | <0.0032 | <0.0032 | 0.023 | 19.210 | 0.231 | >50 | >50 | 13.770 | 0.960 |
| 1031.12.9D9 | <0.0032 | <0.0032 | <0.0032 | <0.0032 | 0.071 | 0.030 | >50 | >50 | 18.220 | 3.540 |
| 1.7.1A7 | 0.280 | 0.116 | 0.189 | >50 | 6.800 | 0.176 | 0.061 | 0.743 | >25 | >25 |
| 1.7.1D2 | 10.695 | 0.939 | 0.998 | >50 | >50 | 0.669 | 0.062 | 10.213 | >25 | 11.920 |
| 1.7.1G10 | >50 | 0.199 | 0.185 | 0.871 | 1.506 | 0.745 | 0.266 | 0.307 | >25 | >25 |
| 233.7.1B2 | >50 | 0.100 | 0.212 | >50 | <0.0032 | 0.158 | <0.0032 | 0.057 | 15.000 | >25 |
| 233.7.1C3 | >50 | 0.973 | 1.771 | >50 | >50 | >50 | 0.041 | 0.132 | 10.700 | 8.030 |
| 233.7.1C11 | >50 | 0.241 | 0.226 | 0.755 | 11.125 | 0.036 | >50 | 0.525 | 13.370 | 18.480 |
| 458.5.12B1 | 17.496 | 0.375 | 0.587 | 25.217 | 1.510 | 0.587 | 0.123 | >50 | 0.880 | 9.990 |
| 458.5.12E1 | 5.263 | 0.265 | 0.314 | 11.871 | 4.460 | 0.414 | 0.234 | >50 | 2.110 | 1.850 |
| 458.5.12G9 | 6.84 | 0.151 | 0.351 | 2.896 | 2.099 | 0.832 | 0.093 | >50 | 9.440 | 4.910 |
| 172.7C6 | 0.701 | 0.024 | 0.089 | 0.321 | 9.717 | 0.057 | >50 | >50 | ND | ND |
| 172.7F11 | 0.140 | 0.001 | 0.001 | 0.023 | 19.210 | 0.231 | >50 | >50 | ND | ND |
| 172.7G5 | 0.001 | 0.001 | 0.001 | 0.001 | 0.071 | 0.030 | >50 | >50 | ND | ND |
| 1161.9G11 | 0.260 | 0.116 | 0.189 | >50 | 6.800 | 0.176 | 0.061 | 0.743 | ND | ND |
| 1161.9C1 | 10.695 | 0.939 | 0.998 | >50 | >50 | 0.669 | 0.062 | 10.213 | ND | ND |
| 537.8.A11 | >50 | 0.199 | 0.185 | 0.871 | 1.508 | 0.745 | 0.268 | 0.307 | ND | ND |
| 537.8.E6 | >50 | 0.100 | 0.212 | >50 | 0.001 | 0.158 | 0.001 | 0.057 | ND | ND |
| 537.8.E10 | >50 | 0.973 | 1.771 | >50 | >50 | >50 | 0.041 | 0.132 | ND | ND |

| | | Virus ID | 2G12 | 2F5 | PG9 | PG16 | VRC01 | 45-46 54W | PGT121 | 10-1074 |
|---|---|---|---|---|---|---|---|---|---|---|
| CONTEMPORARY HISTORICAL | | P035.6.EA | <0.39 | 3.480 | >1 | >1 | <0.078 | 0.032 | 15.471 | 0.059 |
| | | P035.6.H11 | <0.39 | 2.115 | >1 | >1 | 0.160 | 0.018 | 0.667 | 0.413 |
| | | P035.6.D10 | <0.39 | 1.900 | >1 | >1 | 0.390 | 0.020 | 0.174 | 0.110 |
| | | P151.37.C7 | >25 | 3.350 | <0.016 | <0.016 | <0.078 | 0.109 | >50 | >50 |
| | | P151.37.F1 | >25 | 1.372 | <0.016 | <0.016 | 0.250 | 0.472 | >50 | >50 |
| | | P151.37.F10 | >25 | <0.39 | <0.016 | <0.016 | 1.160 | 0.172 | >50 | >50 |
| | | P153.10.2.A9 | 0.825 | 0.918 | >1 | 0.431 | >5 | 34.912 | 42.623 | 1.466 |
| | | P153.10.2.D8 | 3.562 | 24.193 | >1 | 0.853 | 0.890 | 0.325 | 1.603 | 0.620 |
| | | P153.10.2.E10 | <0.39 | 22.382 | >1 | <0.016 | >5 | >50 | >50 | >50 |
| | | P186.12.1.D10 | >25 | 2.492 | >1 | >1 | >5 | 22.865 | 0.021 | 0.212 |
| | | P186.12.1.F4 | >25 | 15.277 | >1 | >1 | 3.320 | 15.929 | 0.026 | 0.094 |
| | | P186.12.1.G2 | 21.986 | 3.181 | >1 | >1 | >5 | 16.385 | 0.018 | 0.108 |
| | | P195.31.A6 | >25 | 3.884 | >1 | >1 | 0.890 | >50 | >50 | >50 |
| | | P195.31.A10 | >25 | <0.39 | >1 | >1 | 4.800 | >50 | >50 | >50 |
| | | P195.31F11 | >25 | 2.306 | >1 | >1 | 1.930 | >50 | >50 | >50 |
| | | P019.1.D2 | <0.39 | <0.39 | <0.016 | <0.016 | 0.220 | 0.051 | >50 | 0.191 |
| | | P019.1.D8 | 9.371 | <0.39 | <0.016 | <0.016 | <0.078 | 0.043 | >50 | 0.528 |
| | | P019.1.G7 | 6.764 | <0.39 | 0.050 | 0.034 | <0.078 | <0.0032 | >50 | 0.318 |
| | | P175.10.D7 | <0.39 | >25 | >1 | 0.110 | 1.100 | 0.022 | 0.068 | 0.097 |
| | | P175.10.D12 | <0.39 | >25 | >1 | 0.150 | 0.170 | 0.032 | 0.085 | 0.241 |
| | | P175.10.G10 | 2.183 | 1.300 | 0.720 | 0.032 | 1.660 | 0.017 | 0.069 | 0.220 |
| | | P013.18.A9 | >25 | 2.763 | >1 | >1 | >5 | 0.083 | 5.844 | >50 |
| | | P154.44.C8 | >25 | >25 | <0.016 | 0.600 | >5 | >50 | >50 | >50 |
| | | P154.44.G8 | >25 | >25 | <0.016 | >1 | 0.790 | 0.536 | 1.996 | 0.521 |
| | | P183.50.2.H3 | 6.688 | 1.527 | >1 | >1 | 1.031 | 0.195 | 2.106 | 0.185 |
| | | P183.3.2.B9 | 2.132 | 1.073 | >1 | >1 | 0.340 | 0.056 | 5.073 | 0.266 |

TABLE 8-continued

In vitro PBMC-based neutralization assay

| | | | | | | | | |
|---|---|---|---|---|---|---|---|---|
| P001.35.F5 | >25 | >25 | <0.016 | <0.016 | >5 | 0.946 | 1.873 | 0.046 |
| P001.35.H4 | >25 | >25 | <0.016 | <0.016 | 4.300 | 0.051 | 2.648 | 0.052 |
| P002.39.CB | 2.216 | >25 | <0.016 | <0.016 | <0.078 | 0.450 | 1.129 | 0.024 |
| P002.39.FB | <0.39 | 17.778 | <0.016 | <0.016 | 1.610 | 0.625 | 22.125 | 0.049 |
| P002.39.H10 | <0.39 | 1.500 | <0.016 | 0.048 | 3.030 | 0.917 | 1.985 | 0.042 |
| P034.6.D6 | 0.844 | 0.873 | <0.016 | 0.122 | <0.078 | 0.859 | 0.027 | <0.0032 |
| P034.6.G10 | <0.39 | 1.257 | >1 | >1 | >5 | >50 | >50 | 0.028 |
| P034.6.H5 | >25 | 1.163 | 0.017 | 0.021 | 0.310 | 0.127 | 0.037 | 0.018 |
| P101.20.1.F1 | >25 | 2.721 | >1 | >1 | 2.420 | 0.676 | <0.0032 | <0.0032 |
| P101.20.1.HB | >25 | 1.719 | >1 | >1 | 1.470 | 0.861 | <0.0032 | <0.0032 |
| P127.46.A6 | 2.345 | 1.671 | 0.079 | <0.016 | <0.078 | 0.143 | >50 | >50 |
| P127.46.D1 | <0.39 | 0.921 | 0.101 | 0.150 | 0.230 | 0.203 | >50 | >50 |
| P127.46.D2 | >25 | 1.126 | 0.378 | <0.016 | <0.078 | 0.023 | >50 | >50 |
| P174.28.E11 | 0.974 | 1.674 | 0.023 | <0.016 | 3.910 | 1.863 | 0.085 | 0.050 |
| P177.25.1.G9 | >25 | 5.854 | >1 | >1 | <0.078 | 0.325 | 0.128 | 0.034 |
| P177.25.2.B4 | >25 | 1.241 | >1 | >1 | 0.450 | 0.530 | 0.029 | 0.023 |
| P177.25.2.D1 | >25 | 1.232 | >1 | >1 | 3.630 | 0.066 | 0.017 | 0.018 |
| P180.14.A6 | 17.668 | >25 | 0.038 | <0.016 | 1.000 | 2.094 | 0.139 | 0.028 |
| P180.14.G6 | 2.988 | >25 | <0.016 | <0.016 | 2.380 | 0.306 | 0.174 | 0.020 |
| P180.14.G7 | 2.400 | >25 | <0.016 | <0.016 | 1.240 | 1.012 | 0.028 | 0.038 |
| P197.25.1.D2 | >12.5 | 1.224 | <0.016 | <0.016 | 0.090 | 0.025 | 14.287 | 0.095 |
| P197.25.1.D7 | 1.232 | 1.291 | <0.016 | <0.016 | <0.078 | 0.052 | 20.337 | 0.057 |
| P197.25.1.H1 | 1.079 | 2.088 | <0.016 | <0.016 | <0.078 | 0.072 | 23.417 | 0.092 |
| P405.18.D3 | <0.39 | 1.137 | >1 | >1 | >5 | 0.254 | 0.071 | 0.018 |
| P405.18.F10 | <0.39 | 0.804 | ND | ND | >5 | >50 | 5.680 | >50 |
| P405.18.H5 | 0.986 | 0.815 | 0.141 | <0.016 | >5 | >50 | 4.760 | 0.187 |
| P405.19.A8 | 0.814 | 0.878 | >1 | 0.044 | 0.470 | 0.031 | 0.917 | <0.0032 |
| P405.19.B12 | 0.986 | 1.029 | 0.190 | <0.016 | >5 | <0.0032 | <0.0032 | <0.0032 |
| P405.19.F11 | <0.39 | 3.630 | 0.190 | 0.034 | >5 | ND | ND | ND |
| 1140.6F5 | >25 | 3.790 | <0.016 | <0.016 | <0.078 | <0.0032 | 0.017 | 0.019 |
| 1170.6G9 | >25 | 1.520 | <0.016 | <0.016 | <0.078 | 0.019 | 0.112 | 0.024 |
| P116.2 | >25 | 4.170 | <0.016 | <0.016 | <0.078 | <0.0032 | 0.017 | <0.0032 |
| P116.3.F6 | >25 | 3.080 | <0.016 | <0.016 | <0.078 | 0.020 | 0.019 | <0.0032 |
| P116.3.G9 | >25 | 3.460 | <0.016 | <0.016 | <0.078 | <0.0032 | 0.033 | <0.0032 |
| P116.4.11 | >25 | 7.860 | <0.016 | <0.016 | <0.078 | <0.0032 | <0.0032 | <0.0032 |
| 1234.3A9 | >25 | >25 | <0.016 | <0.016 | <0.078 | <0.0032 | 0.022 | <0.0032 |
| 1234.3D9 | >25 | 8.550 | <0.016 | <0.016 | <0.078 | 0.028 | 0.022 | <0.0032 |
| 658.8A6 | >25 | >25 | 0.142 | 0.032 | <0.078 | <0.0032 | 0.151 | 0.049 |
| 658.8D2 | >25 | 17.210 | 0.135 | <0.016 | <0.078 | <0.0032 | 0.051 | 0.029 |
| 658.8F8 | >25 | >25 | 0.039 | <0.016 | <0.078 | <0.0032 | 0.026 | 0.017 |
| 526.17-2C11 | ND | ND | <0.016 | <0.016 | 0.199 | 0.046 | <0.0032 | <0.0032 |
| 526.17-2G1 | ND | ND | 0.059 | <0.016 | 0.840 | 0.074 | <0.0032 | 0.018 |
| 526.17-2G3 | ND | ND | <0.016 | <0.016 | 0.354 | <0.0032 | 0.087 | <0.0032 |
| 424.9F4 | ND | ND | <0.016 | <0.016 | 0.310 | 0.028 | 0.032 | 0.019 |
| 424.9H1 | ND | ND | 0.039 | <0.016 | >5 | 0.369 | 3.731 | 1.087 |
| 139.19A6 | ND | ND | <0.016 | <0.016 | 0.557 | 0.127 | 0.068 | 0.017 |
| 139.19.C10 | ND | ND | <0.016 | <0.016 | 1.549 | 0.688 | 0.118 | 0.039 |
| 139.19.F2 | ND | ND | <0.016 | <0.016 | >5 | 0.669 | 0.106 | 0.039 |
| 208.9.C6 | ND | ND | 0.063 | 0.248 | 0.303 | 0.100 | 0.125 | 0.137 |
| 208.9.F12 | ND | ND | >1 | >1 | 0.714 | 0.128 | 0.086 | 0.151 |
| 208.9.G10 | ND | ND | 0.882 | >1 | 0.289 | 0.083 | <0.0032 | 0.023 |
| 1031.12.6C4 | >25 | 6.280 | >1 | >1 | 0.160 | 0.040 | <0.0032 | <0.0032 |
| 1031.12.7D5 | >25 | 8.500 | >1 | >1 | 0.120 | 0.072 | <0.0032 | <0.0032 |
| 1031.12.9D9 | >25 | 10.770 | >1 | >1 | 0.200 | 0.102 | <0.0032 | <0.0032 |
| 1.7.1A7 | >25 | >25 | <0.016 | <0.016 | 0.640 | ND | ND | ND |
| 1.7.1D2 | >25 | >25 | <0.016 | <0.016 | 0.700 | 0.300 | 0.045 | 0.048 |
| 1.7.1G10 | >25 | >25 | <0.016 | <0.016 | <0.078 | 0.282 | 0.017 | <0.0032 |
| 233.7.1B2 | 0.140 | 5.030 | 0.019 | <0.016 | 0.160 | 0.019 | 0.030 | <0.0032 |
| 233.7.1C3 | 0.330 | 5.900 | 0.526 | >1 | <0.078 | 0.027 | <0.0032 | <0.0032 |
| 233.7.1C11 | 0.870 | 5.460 | >1 | 0.370 | 0.090 | 0.024 | 0.023 | 0.038 |
| 458.5.12B1 | >25 | 3.820 | 0.028 | 0.311 | 1.370 | 0.035 | 0.018 | 0.018 |
| 458.5.12E1 | 22.620 | 1.660 | <0.016 | <0.016 | <0.078 | 0.072 | 0.201 | 0.020 |
| 458.5.12G9 | >25 | 2.350 | >1 | 0.039 | 0.100 | 0.223 | 0.022 | 0.023 |
| 172.7C6 | ND | ND | 0.020 | <0.016 | 0.431 | 0.019 | 0.025 | 0.027 |
| 172.7F11 | ND | ND | 0.017 | <0.016 | 0.424 | 0.021 | 0.020 | 0.025 |
| 172.7G5 | ND | ND | 0.048 | <0.016 | <0.078 | <0.0032 | 0.035 | <0.0032 |
| 1161.9G11 | ND | ND | >1 | >1 | 0.378 | 0.021 | <0.0032 | 0.020 |
| 1161.9C1 | ND | ND | >1 | >1 | >5 | 0.618 | 0.065 | 0.051 |
| 537.8.A11 | ND | ND | >1 | >1 | 3.459 | 0.270 | 0.031 | 0.021 |
| 537.8.E6 | ND | ND | >1 | >1 | 0.331 | 0.065 | 0.086 | 0.027 |
| 537.8.E10 | ND | ND | >1 | >1 | 2.071 | 0.174 | 0.025 | 0.017 |

Numbers indicate antibody IgG concentrations in µg/ml to reach the $IC_{50}$ in the PBMC-based neutralization assay.
$IC_{50}$ values indicate an increasing neutralization sensitivity.
>indicates that the $IC_{50}$ for a given virus was not reached at the concetration tested.
ND, not determined.

TABLE 9

Data collection and refinement statistics (molecular replacement)

| | PGT121 Fab "unliganded" | 10-1074 Fab | GL Fab | PGT121 Fab "liganded" |
|---|---|---|---|---|
| Data collection | | | | |
| Space group | $P2_12_12_1$ | $P2_1$ | $P2_1$ | $P2_12_12_1$ |
| Cell dimensions | | | | |
| a, b, c (Å) | 56.75, 74.67, 114.917 | 61.38, 40.26, 84.46 | 54.93, 344.74, 55.23 | 67.79, 67.79, 94.11 |
| α, β, γ (°) | 90.00, 90.00, 90.00 | 90.00, 95.39, 90.00 | 90.00, 91.95, 90.00 | 90.00, 90.00, 90.00 |
| Resolution (Å) | 2.78-35.5 (2.78-2.93) | 1.80-36.31 (1.80-1.91) | 2.42-38.60 (2.42-2.55) | 2.33-38.66 (2.33-2.47) |
| $R_{merge}$ | 0.099 (0.293) | 0.075 (0.558) | 0.072 (0.482) | 0.161 (0.603) |
| I/σ$_i$ | 8.8 (3.1) | 8.7 (1.8) | 11.0 (1.9) | 8.7 (2.9) |
| Completeness (%) | 96.7 (84.8) | 93.49 (98.0) | 95.5 (80.1) | 92.2 (98.9) |
| Redundancy | 3.2 (2.7) | 2.7 (2.8) | 3.1 (2.6) | 5.3 (5.8) |
| Refinement | | | | |
| Resolution (Å) | 3.0 | 1.9 | 2.42 | 2.4 |
| No. reflections | 10,076 | 31,363 | 74,237 | 16,831 |
| $R_{work}/R_{free}$ | 0.216/0.264 | 0.187/0.223 | 0.194/0.237 | 0.201/0.249 |
| No. atoms | | | | |
| Protein | 3,276 | 3,346 | 12,881 | 3,127 |
| Ligand/ion | 0 | 0 | 0 | 129 |
| Water | 0 | 300 | 527 | 203 |
| B-factors | | | | |
| Protein | 32.78 | 29.17 | 44.67 | 31.48 |
| Ligand/ion | — | — | — | 45.1 |
| Water | — | 37.37 | 40.27 | 36.78 |
| R.m.s. deviations | | | | |
| Bond lengths (Å) | 0.005 | 0.007 | 0.005 | 0.006 |
| Bond angles (°) | 0.971 | 1.234 | 0.951 | 0.949 |

*Data for each structure were acquired from a single crystal.
*Values in parentheses are for the highest-resolution shell.

TABLE 10

RMSD values for Cα alignments of Fabs

| Fab1/Fab2 | $RMSD_{VH}$ (Å) | # residues | $RMSD_{VL}$ (Å) | # residues | $RMSD_{VH+VL}$ (Å) | # residues |
|---|---|---|---|---|---|---|
| PGT121/PGT128 | 1.159 | 116/130 | 1.63 | 95/100 | 1.462 | 207/235 |
| PGT121/PGT145 | 2.93 | 124/130 | 1.91 | 94/105 | 1.75 | 206/235 |
| PGT121/10-1074 | 0.74 | 128/130 | 1.2 | 102/105 | 1.26 | 226/235 |
| PGT121/GL | 1.33 | 129/130 | 1.37 | 94/105 | 1.6 | 225/235 |
| 10-1074/GL | 1.38 | 130/130 | 1.35 | 92/105 | 1.39 | 220/235 |
| PGT121/PGT121$_{liganded}$ | 0.79 | 125/128 | 0.5 | 100/100 | 0.78 | 225/228 |

TABLE 11

Contacts between PGT121 Fab and bound glycan

| Glycan atom | Protein atom | Water | Distance (Å) |
|---|---|---|---|
| GlcNAc$^6$-O3 | Asn$^{58}$-Nδ2 | | 2.91 |
| GlcNAc$^6$-O7 | Asn$^{58}$-Oδ1 | | 2.94 |
| GlcNAc$^6$-O6 | | H$_2$O$^{471}$ | 3.15 |
| GlcNAc$^6$-O4 | | H$_2$O$^{477}$ | 3.05 |
| GlcNAc$^6$-O3 | | H$_2$O$^{481}$ | 2.94 |
| Man$^1$-O4 | | H$_2$O$^{410}$ | 3.02 |
| Man$^1$-O4 | | H$_2$O$^{420}$ | 2.66 |
| Man$^1$-O3 | | H$_2$O$^{410}$ | 3.35 |
| Man$^1$-O2 | | H$_2$O$^{477}$ | 3.14 |
| Man$^1$-O5 | | H$_2$O$^{477}$ | 2.62 |
| Man$^2$-O6 | Thr$^{100}$-Oγ1 | | 3.34 |
| Man$^2$-O2 | | H$_2$O$^{410}$ | 3.41 |
| Man$^2$-O5 | | H$_2$O$^{446}$ | 2.95 |
| Man$^2$-O6 | | H$_2$O$^{446}$ | 3.26 |
| GlcNAc$^7$-N2 | Tyr$^{33}$-OH | | 2.72 |
| GlcNAc$^7$-O5 | | H$_2$O$^{410}$ | 3.38 |
| GlcNAc$^7$-O7 | | H$_2$O$^{411}$ | 3.00 |
| GlcNAc$^7$-O3 | His$^{97}$-Nδ2 | | 3.60* |
| GlcNAc$^7$-O7 | His$^{97}$-Nε2 | | 3.70* |
| Gal$^8$-O3 | Lys$^{53}$-Nζ | | 2.97 |
| Gal$^8$-O4 | | H$_2$O$^{480}$ | 3.47 |
| Gal$^8$-O4 | | H$_2$O$^{435}$ | 2.76 |
| Gal$^8$-O5 | | H$_2$O$^{435}$ | 3.17 |
| Sia$^{10}$-O8 | Asp$^{31}$-O | | 2.72 |
| Sia$^{10}$-O10 | His$^{97}$-N | | 3.18 |
| Sia$^{10}$-O10 | His$^{97}$-O | | 3.19 |
| Sia$^{10}$-O9 | | H$_2$O$^{480}$ | 3.19 |
| Sia$^{10}$-O8 | Ser$^{32}$-Oγ | | 3.70* |
| Man$^3$-O3 | Asn$^{58}$-Oδ1 | | 2.58 |
| Man$^3$-O6 | | H$_2$O$^{477}$ | 3.35 |
| GlcNAc$^4$-O5 | Thr$^{57}$-O | | 3.33 |
| GlcNAc$^4$-N2 | | H$_2$O$^{479}$ | 3.2 |
| Fuc$^9$-O2 | | H$_2$O$^{471}$ | 2.57 |
| | Asp$^{31}$-O | H$_2$O$^{435}$ | 3.09 |

TABLE 11-continued

Contacts between PGT121 Fab and bound glycan

| Glycan atom | Protein atom | Water | Distance (Å) |
|---|---|---|---|
| | Asp$^{31}$-O$\delta$1 | H$_2$O$^{480}$ | 3.32 |
| | Tyr$^{50}$-OH | H$_2$O$^{481}$ | 2.8 |
| | His$^{52}$-N$\epsilon$2 | H$_2$O$^{435}$ | 3.16 |
| | Ser$^{54}$-O$\gamma$ | H$_2$O$^{410}$ | 3.2 |
| | Ser$^{54}$-O | H$_2$O$^{420}$ | 3.16 |
| | Gly$^{55}$-O | H$_2$O$^{479}$ | 2.85 |
| | Asp$^{56}$-O$\delta$1 | H$_2$O$^{481}$ | 3.49 |
| | Asp$^{56}$-O$\delta$2 | H$_2$O$^{448}$ | 3.07 |
| | Asn$^{58}$-N$\delta$2 | H$_2$O$^{481}$ | 3.15 |
| | Arg$^{99}$-N$\epsilon$ | H$_2$O$^{411}$ | 2.58 |
| | Thr$^{100I}$-O$\gamma$1 | H$_2$O$^{411}$ | 2.94 |

Hydrogen bond criteria: bond distance <3.5 Å, O—H—O/N—H—O angle >90°
*Contacts are close to hydrogen bond distance cutoff and are included as possible interactions

TABLE 12

In vitro neutralization activity of PGT121GM and 10-1074GM

| Virus ID | Clade | PGT121 | PGT121GM | 10-1074 | 10-1074GM |
|---|---|---|---|---|---|
| Q842.d12 | A | 0.074 | >50 | >50 | >50 |
| 3365.v2.c2 | A | 7.353 | >50 | 0.450 | 0.467 |
| 0260.v5.c36 | A | 0.152 | >50 | 0.160 | 0.618 |
| YU.2 | B | 0.356 | 1.355 | 0.398 | 0.262 |
| TRO.11 | B | 0.051 | 0.258 | 0.057 | 0.049 |
| TRJO4551.58 | B | 35.291 | >50 | 0.634 | 0.721 |
| QH0692.42 | B | 8.545 | >50 | 0.929 | 0.376 |
| PVO.4 | B | 0.945 | 47.564 | 0.360 | 0.138 |
| RHPA4259.7 | B | 0.054 | 20.801 | 0.118 | 0.087 |
| WITO4160.33 | B | 6.007 | >50 | 2.112 | 0.406 |
| 1054_07_TC4_1499 | B (T/F) | 0.696 | >50 | 0.563 | 0.193 |
| 6244_13_B5_4576 | B (T/F) | 1.878 | 46.680 | 0.922 | 0.394 |
| 62357_14_D3_4589 | B (T/F) | 45.559 | >50 | >50 | 40.782 |
| CNE19 | BC | 0.189 | 48.092 | 50 | 0.379 |
| CNE17 | BC | >50 | >50 | 13.297 | 4.816 |
| CNE58 | BC | >50 | >50 | 0.968 | 1.158 |
| CNE30 | BC | 0.559 | 8.401 | 1.200 | 1.045 |
| CNE52 | BC | 32.935 | >50 | 13.147 | 6.664 |
| ZM233M.PB6 | C | 8.977 | >50 | 0.349 | 0.232 |
| ZM53M.PB12 | C | 0.002 | >50 | >50 | >50 |
| CAP45.2.00.G3 | C | 6.544 | >50 | >50 | >50 |
| HIV-16055-2.3 | C | 4.290 | >50 | >50 | >50 |
| HIV-16845-2.22 | C | >50 | >50 | 5.835 | 2.678 |
| ZM214M.PL15 | C | 3.150 | >50 | 2.367 | 0.200 |
| ZM135M.PL10a | C | 5.885 | >50 | 0.367 | 0.184 |
| Ce1086_B2 | C (T/F) | 0.006 | >50 | >50 | >50 |
| Ce1172_H1 | C (T/F) | 0.088 | 0.180 | 0.166 | 0.054 |
| 1394C9G1(Rev-) | C (T/F) | 3.372 | 2.120 | 0.191 | 0.075 |
| 3817.v2.c59 | CD | >50 | >50 | 14.880 | 3.423 |
| 6952.v1.c20 | CD | 0.605 | >50 | 0.138 | 0.134 |
| BJOX009000.02.4 | CRF01_AE | 37.289 | >50 | >50 | >50 |
| 211-9 | CRF02_AG | 8.840 | >50 | 0.425 | 0.976 |
| 928-28 | CRF02_AG | >50 | >50 | 4.696 | 3.121 |
| T251-18 | CRF02_AG | >50 | >50 | 7.395 | 3.459 |
| T278-50 | CRF02_AG | >50 | >50 | 18.276 | 12.017 |
| 263-8 | CRF02_AG | 24.576 | >50 | 6.527 | 7.779 |
| 235-47 | CRF02_AG | 1.676 | >50 | 0.163 | 0.069 |
| A07412m1.vrv12 | D | 0.406 | 16.947 | 0.048 | 0.044 |
| X1193_c1 | G | 0.202 | 11.859 | 0.475 | 0.195 |
| X1254_c3 | G | 0.199 | 0.222 | 0.297 | 0.112 |

Numbers indicate antibody IgG concentrations in μg/ml to reach the IC$_{50}$ in the TZM-bl neutralization assay.
IC$_{50}$ values indicate an increasing neutralization sensitivity.
>indicates that the IC$_{50}$ for a given virus was not reached at the concentration tested.

TABLE 13

SHIV$_{AD8EO}$

| Animal ID | Abs | Dosage | PROTECTED | Abs conc (μg/ml) at Day 0 | Titer (TZM-bl) at Day 0 |
|---|---|---|---|---|---|
| RHDEGF | VRC01 | 50 mg/Kg | Yes | 586.9 | 1:162 |
| RHDEH3 | | | No | 711.0 | 1:176 |
| RHDE1L | | 20 mg/Kg | No | 206.5 | 1:65 |
| RHJBN | | | No | 188.1 | 1:68 |
| RHKNX | PGT121 | 20 mg/Kg | Yes | 267.9 | 1:2495 |
| RHMK4 | | | Yes | 253.6 | 1:2773 |

TABLE 13-continued

| Animal ID | Abs | dosage | PROTECTED | Abs conc (µg/ml) at Day 0 | Titer (TZM-bl) at Day 0 |
|---|---|---|---|---|---|
| RHDE9J | | 5 mg/Kg | Yes | 55.7 | 1:563 |
| RHPNR | | | No | 47.2 | 1:618 |
| RHDCGI | | 1 mg/Kg | Yes | 24.0 | 1:116 |
| RHKNE | | | Yes | 19.7 | 1:55 |
| RHK44 | | 0.2 mg/Kg | No | 1.8 | <1:20 |
| RHK49 | | | No | 1.8 | 1:17 |
| RHDEEM | 10-1074 | 20 mg/Kg | Yes | 289.8 | 1:2004 |
| RHKIL | | | Yes | 257.7 | 1:2075 |
| RHME1 | | 5 mg/Kg | Yes | 112.9 | 1:633 |
| RHPNV | | | Yes | 117.5 | 1:384 |
| RHPID | | 1 mg/Kg | No | 19.9 | 1:56 |
| RHDCHX | | | No | 24.8 | 1:53 |
| RHPZE | 3BNC117 | 5 mg/Kg | Yes | 105.4 | 1:272 |
| RHPM5 | | | Yes | 76.1 | 1:372 |
| RHKMH | | 1 mg/Kg | No | 39.6 | 1:55 |
| RHMJ5 | | | No | 15.1 | 1:75 |
| RHPLD | 45-46m2 | 20 mg/Kg | No | 15.0 | 1:27 |
| RHMA9 | | | No | 17.6 | <1:20 |
| RHMC6 | | 5 mg/Kg | No | 2.3 | <1:20 |
| RHDE0CA | | | No | 2.2 | <1:20 |
| RHML1 | DEN3 | 20 mg/Kg | No | ND | <1:20 |
| RHMAA | | | No | ND | <1:20 |

SHIV$_{DH12-V3AD8}$

| Animal ID | Abs | dosage | PROTECTED | Abs conc (µg/ml) at Day 0 | Titer (TZM-bl) at Day 0 |
|---|---|---|---|---|---|
| RHDEJ3 | VRC01 | 30 mg/Kg | Yes | 395.8 | 1:52 |
| RHKZ1 | | | No | 306.0 | 1:70 |
| RHKZA | PGT121 | 20 mg/Kg | Yes | 215.1 | 1:13120 |
| RHDECT | | | Yes | 200.7 | 1:13805 |
| RHKTL | | | Yes | 282.7 | 1:12669 |
| RHPZ9 | | | Yes | 133.1 | 1:12055 |
| RHK2Z | | 1 mg/Kg | Yes | 15.1 | 1:422 |
| RHMT8 | | | No | 29.3 | 1:539 |
| RHDEEB | | 0.2 mg/Kg | Yes | 3.1 | 1:159 |
| RHDEP2 | | | Yes | 1.6 | 1:101 |
| RHMFD | | 0.05 mg/Kg | No | 1.0 | <1:20 |
| RHKIA | | | No | 1.3 | <1:20 |
| RHKIM | 10-1074 | 20 mg/Kg | Yes | 290.3 | 1:1972 |
| RHKWM | | | Yes | 173.3 | 1:2282 |
| RHMJW | | 5 mg/Kg | Yes | 96.6 | 1:420 |
| RHMJT | | | Yes | 95.3 | 1:376 |
| RHDENI | | 1 mg/Kg | Yes | 28.4 | 1:106 |
| RHJHZ | | | No | 18.6 | 1:136 |
| RHHE8 | | 0.2 mg/Kg | No | 19.4 | 1:39 |
| RHKCZ | | | No | 19.7 | 1:35 |
| RHMFBA | 3BNC117 | 20 mg/Kg | Yes | 294.9 | 1:143 |
| RHMER | | | Yes | 272.7 | 1:142 |
| RHKIV | | 5 mg/Kg | Yes | 114.6 | 1:80 |
| RHKPI | | | No | 133.1 | 1:90 |
| RHDE9D | | 1 mg/Kg | No | 23.3 | 1:20 |
| RHDEW7 | | | Yes | 29.6 | 1:18 |
| RHMEV | | 0.2 mg/Kg | No | 3.9 | <1:20 |
| RHMF9 | | | No | 5.7 | <1:20 |
| RHKZMA | 45-46m2 | 5 mg/Kg | No | 2.1 | ND |
| RHKNP | | | No | 4.0 | ND |
| RHJII | hu-IgG | 100 mg/Kg | No | ND | ND |
| RHJK1 | | | No | ND | ND |

TABLE 14

| | IC$_{50}$ in TZM-bl cells[1] | | | | | | | HIVIG (µg/ml) | Tier Phenotype |
|---|---|---|---|---|---|---|---|---|---|
| Sample ID | S321 | C500 | B520 | G435 | T520b | M263 | M600c | | |
| R5 SHIV$_{DH12-V3AD8}$ | 321 | 289 | 77 | 172 | 168 | 429 | 134 | 132 | 2 |
| R5 SHIV$_{AD8-EO}$ | 48 | 36 | 39 | 31 | 41 | 44 | 48 | 1768 | 2 |
| X4 SHIV$_{DH12-CL7}$ | 110 | 94 | 50 | 65 | 109 | 115 | 65 | 530 | 2 |
| HIV-1$_{CAAN5342.A2}$ | 84 | <20 | 27 | <20 | <20 | 77 | 185 | 638 | 2 |
| HIV-1$_{MN.3}$ | 13944 | 9152 | 822 | 8432 | 3968 | 43722 | 1709 | 1.81 | 1 |

[1]Values are the serum dilution at which relative luminescence units (RLUs) were reduced 50% compared to virus control wells (no test sample).

TABLE 15

| | SHIVAD8EO | | | | | |
|---|---|---|---|---|---|---|
| Endpoint neutralization | Animal number | | Accumulated value | | Protected | |
| titer in plasma | Protected | Infected | Protected[a] | Infected[b] | Ratio | % |
| 2773 | 1 | 0 | 12 | 0 | 12/12 | 100% |
| 2495 | 1 | 0 | 11 | 0 | 11/11 | 100% |
| 2075 | 1 | 0 | 10 | 0 | 10/10 | 100% |
| 2004 | 1 | 0 | 9 | 0 | 9/9 | 100% |
| 633 | 1 | 0 | 8 | 0 | 8/8 | 100% |
| 618 | 0 | 1 | 7 | 1 | 7/8 | 88% |
| 563 | 1 | 0 | 7 | 1 | 7/8 | 88% |
| 384 | 1 | 0 | 6 | 1 | 6/7 | 86% |
| 372 | 1 | 0 | 5 | 1 | 5/6 | 83% |
| 272 | 1 | 0 | 4 | 1 | 4/5 | 80% |
| 176 | 0 | 1 | 3 | 2 | 3/5 | 60% |
| 162 | 1 | 0 | 3 | 2 | 3/5 | 60% |
| 115 | 1 | 0 | 2 | 2 | 2/4 | 50%[c] |
| 75 | 0 | 1 | 1 | 3 | 1/4 | 25% |
| 68 | 0 | 1 | 1 | 4 | 1/5 | 20% |
| 65 | 0 | 1 | 1 | 5 | 1/6 | 17% |
| 56 | 0 | 1 | 1 | 6 | 1/7 | 14% |
| 55 | 1 | 0 | 1 | 6 | 1/7 | 14% |
| 55 | 0 | 1 | 0 | 7 | 0/7 | 0% |
| 53 | 0 | 1 | 0 | 8 | 0/8 | 0% |
| 27 | 0 | 1 | 0 | 9 | 0/9 | 0% |
| 20 | 0 | 1 | 0 | 10 | 0/10 | 0% |
| 20 | 0 | 1 | 0 | 11 | 0/11 | 0% |
| 20 | 0 | 1 | 0 | 12 | 0/12 | 0% |
| 20 | 0 | 1 | 0 | 13 | 0/13 | 0% |
| 17 | 0 | 1 | 0 | 14 | 0/14 | 0% |

[a]Sum from the bottom.
[b]Sum from the top.
[c]Endpoint protection titer (50% protective titer) was calculated to be 1:115

TABLE 16

| | SHIVDH12-V3AD8 | | | | | |
|---|---|---|---|---|---|---|
| Endpoint neutralization | Animal number | | Accumulated value | | Protected | |
| titer in plasma | Protected | Infected | Protected[a] | Infected[b] | Ratio | % |
| 13805 | 1 | 0 | 16 | 0 | 16/16 | 100% |
| 13120 | 1 | 0 | 15 | 0 | 15/15 | 100% |
| 12669 | 1 | 0 | 14 | 0 | 14/14 | 100% |
| 12055 | 1 | 0 | 13 | 0 | 13/13 | 100% |
| 2282 | 1 | 0 | 12 | 0 | 12/12 | 100% |
| 1972 | 1 | 0 | 11 | 0 | 11/11 | 100% |
| 539 | 0 | 1 | 10 | 1 | 10/11 | 91% |
| 422 | 1 | 0 | 10 | 1 | 10/11 | 91% |
| 420 | 1 | 0 | 9 | 1 | 8/10 | 90% |
| 376 | 1 | 0 | 8 | 1 | 8/9 | 89% |
| 159 | 1 | 0 | 7 | 1 | 7/8 | 88% |
| 143 | 1 | 0 | 6 | 1 | 6/7 | 86% |
| 142 | 1 | 0 | 5 | 1 | 5/6 | 83% |
| 136 | 0 | 1 | 4 | 2 | 4/6 | 67% |
| 108 | 1 | 0 | 4 | 2 | 4/6 | 67% |
| 101 | 1 | 0 | 3 | 2 | 3/5 | 60%[c] |
| 90 | 0 | 1 | 2 | 3 | 2/5 | 40%[c] |
| 80 | 1 | 0 | 2 | 3 | 2/5 | 40% |
| 70 | 0 | 1 | 1 | 4 | 1/5 | 20% |
| 52 | 1 | 0 | 1 | 4 | 1/5 | 20% |
| 39 | 0 | 1 | 0 | 5 | 0/5 | 0% |
| 35 | 0 | 1 | 0 | 6 | 0/6 | 0% |
| 20 | 0 | 1 | 0 | 7 | 0/7 | 0% |
| 20 | 0 | 1 | 0 | 8 | 0/8 | 0% |
| 20 | 0 | 1 | 0 | 9 | 0/9 | 0% |
| 20 | 0 | 1 | 0 | 10 | 0/10 | 0% |
| 20 | 0 | 1 | 0 | 11 | 0/11 | 0% |
| 20 | 0 | 1 | 0 | 12 | 0/12 | 0% |
| 20 | 0 | 1 | 0 | 13 | 0/13 | 0% |

[a]Sum from the bottom.
[b]Sum from the top.
[c]Endpoint protection titer (50% protective titer) was calculated to be 1:95.5

TABLE 17

| Animal | Weeks Post infection | Pre-infection CD4+ T Cells cells/μl | Pre mAb Treatment CD4+ T cells cells/μl | Pre mAb Treatment Viral Load RNA Copies/ml | Clinical Status |
|---|---|---|---|---|---|
| DBZ3 | 159 | 650 | 118 | 1.08E+04 | Asymptomatic |
| DC99A | 159 | 623 | 165 | 7.60E+03 | Asymptomatic |
| DBXE | 163 | 1585 | 158 | 1.96E+05 | Intermittent diarrhea |
| DCF1 | 157 | 1203 | 105 | 1.44E+05 | Intermittent diarrhea |
| DCM8 | 163 | 608 | 43 | 1.59E+03 | Intermittent diarrhea |

TABLE 18

| Animal | Treatment Time (Days) | SIV Gag RNA Copies per $10^8$ Cell Eq | SIV Gag DNA Copies per $10^8$ Cell Eq |
|---|---|---|---|
| DBZ3 | 0 | 9,000 | 6,700 |
| DBZ3 | 10 | 360 | 7,600 |
| DBZ3 | 20 | 2,400 | 14,000 |
| DC99A | 0 | 31,000 | 1,400 |
| DC99A | 14 | 18,000 | 5,600 |
| DC99A | 20 | 8,100 | 2,700 |
| DBXE | 0 | 470,000 | 71,000 |
| DBXE | 14 | 17,000 | 33,000 |
| DBXE | 17 | 11,400 | 22,000 |
| DCM8 | 0 | 110,000 | 8,600 |
| DCM8 | 14 | 1,700 | 1,600 |
| DCM8 | 20 | 22,000 | 6,800 |
| DCF1 | 0 | 240,000 | 15,400 |
| DCF1 | 14 | 190,000 | 11,000 |
| DCF1 | 20 | 1,100,000 | 14,000 |

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

The invention claimed is:

1. An isolated anti-HIV antibody, or antigen binding portion thereof, comprising (i) a heavy chain region that comprises CDRH 1, CDRH 2, CDRH 3 and (ii) a light chain region that comprises CDRL 1, CDRL 2 and CDRL 3, wherein said CDRH 1, CDRH 2, CDRH 3, CDRL 1, CDRL 2, and CDRL 3 comprise the sequences of SEQ ID NOs: 39-44, respectively.

2. The isolated anti-HIV antibody of claim 1, or antigen binding portion thereof, wherein the heavy chain region comprises the sequence of SEQ ID NO: 3.

3. The isolated anti-HIV antibody of claim 1, or antigen binding portion thereof, wherein the light chain region comprises the sequence of SEQ ID NO: 4.

4. The isolated anti-HIV antibody of claim 3, or antigen binding portion thereof, wherein the heavy chain region and the light chain region comprise the respective sequences of SEQ ID NOs: 3-4.

5. The isolated anti-HIV antibody of claim 1, or antigen binding portion thereof, wherein the antibody is 10-259.

6. The isolated anti-HIV antibody of claim 1, or antigen binding portion thereof, wherein the antibody is a human antibody, a humanized antibody, or a chimeric antibody.

7. A pharmaceutical composition comprising (i) at least one anti-HIV antibody of claim 1, or antigen binding portion thereof, and (ii) a pharmaceutically acceptable carrier.

8. A method of preventing or treating an HIV infection or an HIV-related disease comprising the steps of:
   identifying a patient in need of such prevention or treatment, and
   administering to said patient a first therapeutic agent comprising a therapeutically effective amount of at least one anti-HIV antibody of claim 1, or antigen binding portion thereof.

9. A method for making an anti-HIV antibody or a fragment thereof, comprising obtaining a cultured cell comprising one or more nucleic acid sequences encoding the heavy chain variable region and the light chain variable region of the anti-HIV antibody of claim 1, or antigen binding portion thereof;
   culturing the cell in a medium under conditions permitting expression of the heavy chain variable region and the light chain variable region and assembling of an antibody or fragment thereof, and
   purifying the antibody or fragment from the cultured cell or the medium of the cell.

10. A kit comprising
   a pharmaceutically acceptable dose unit of a pharmaceutically effective amount of at least one isolated anti-HIV antibody according to claim 1, and
   a pharmaceutically acceptable dose unit of a pharmaceutically effective amount of an anti-HIV agent,
   wherein the two pharmaceutically acceptable dose units can optionally take the form of a single pharmaceutically acceptable dose unit.

11. A method of reducing HIV-1viremia in a subject, comprising administering to the subject an effective amount of the antibody of claim 1, or antigen binding portion thereof.

12. A method of inhibiting HIV-1viremia in a subject, comprising administering to the subject an effective amount of the antibody of claim 1, or antigen binding portion thereof.

* * * * *